US012558336B2

(12) United States Patent
Mahajan et al.

(10) Patent No.: US 12,558,336 B2
(45) Date of Patent: Feb. 24, 2026

(54) METABOLIC RESCUE OF RETINAL DEGENERATION

(71) Applicant: The Board of Trustees of the Leland Stanford Junior University, Stanford, CA (US)

(72) Inventors: Vinit Mahajan, Palo Alto, CA (US); Katherine J. Wert, Dallas, TX (US); Gabriel Velez, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1009 days.

(21) Appl. No.: 17/763,083

(22) PCT Filed: Sep. 24, 2020

(86) PCT No.: PCT/US2020/052535
§ 371 (c)(1),
(2) Date: Mar. 23, 2022

(87) PCT Pub. No.: WO2021/062022
PCT Pub. Date: Apr. 1, 2021

(65) Prior Publication Data
US 2023/0034053 A1 Feb. 2, 2023

Related U.S. Application Data

(60) Provisional application No. 62/905,683, filed on Sep. 25, 2019.

(51) Int. Cl.
| | |
|---|---|
| *A61K 31/215* | (2006.01) |
| *A61K 31/047* | (2006.01) |
| *A61K 31/07* | (2006.01) |
| *A61K 31/202* | (2006.01) |
| *A61K 31/23* | (2006.01) |
| *A61K 31/455* | (2006.01) |
| *A61K 31/525* | (2006.01) |
| *G01N 33/68* | (2006.01) |

(52) U.S. Cl.
CPC .......... *A61K 31/215* (2013.01); *A61K 31/047* (2013.01); *A61K 31/07* (2013.01); *A61K 31/202* (2013.01); *A61K 31/23* (2013.01); *A61K 31/455* (2013.01); *A61K 31/525* (2013.01); *G01N 33/6893* (2013.01); *G01N 2800/164* (2013.01); *G01N 2800/52* (2013.01)

(58) Field of Classification Search
CPC ..................................................... A61K 31/215
See application file for complete search history.

(56) References Cited

U.S. PATENT DOCUMENTS

| | | | |
|---|---|---|---|
| 8,324,270 B2 | 12/2012 | Maeda et al. | |
| 2009/0005437 A1* | 1/2009 | Gottlieb ................. | A61P 43/00 |
| | | | 435/375 |
| 2014/0199277 A1 | 7/2014 | Cosma et al. | |

OTHER PUBLICATIONS

Hamel, Retinitis pigmentosa, Orphanet Journal of Rare Diseases vol. 1, Article No. 40 (2006).*
Wert et al., Metabolite therapy guided by liquid biopsy proteomics delays retinal neurodegeneration, EBioMedicine, vol. 52, Feb. 2020, 102636.*
Wert et al. (2019) "Metabolite therapy guided by liquid biopsy proteomics delays retinal neurodegeneration", bioRxiv preprint, 1-40.

* cited by examiner

Primary Examiner — Svetlana M Ivanova
(74) *Attorney, Agent, or Firm* — Jenny L. Buchbinder; Bozicevic, Field & Francis LLP

(57) ABSTRACT

Methods are provided for treating and diagnosing diseases and disorders associated with retinal degeneration, such as retinitis pigmentosa. Dietary supplementation with specific metabolites and vitamins can prolong vision and provide a neuroprotective effect. In particular, dietary supplementation with a-ketoglutarate, or a derivative thereof, significantly prolongs photoreceptor cell survival and visual function. In addition, dietary supplementation with B vitamins and a ketogenic diet also improves photoreceptor cell survival and delays disease progression in some cases. Additionally, compositions, methods, and kits are provided for diagnosing a subject with retinitis pigmentosa based on expression levels of vitreous biomarkers.

4 Claims, 28 Drawing Sheets p.R102C/p.S303C (II:5)

p.R102C/p.S303C (II:5)

p.R102C/p.S303C (II:5)

p.R102C/p.S303C (II:4)

p.R102C/p.S303C (II:4)

p.R102C/p.S303C (II:4)

Wild-Type P12

$Pde6a^{D670G}$p11

GCL

INL

ONL

RPE

Control

Early-Stage
Disease $Pde6a^{D670G}$p30

$Pde6a^{D670G}$p72

GCL

INL

ONL

RPE

Mid-Stage
Disease

Late-Stage
Disease

Cellular Compartment

Biological process

FIG. 5D

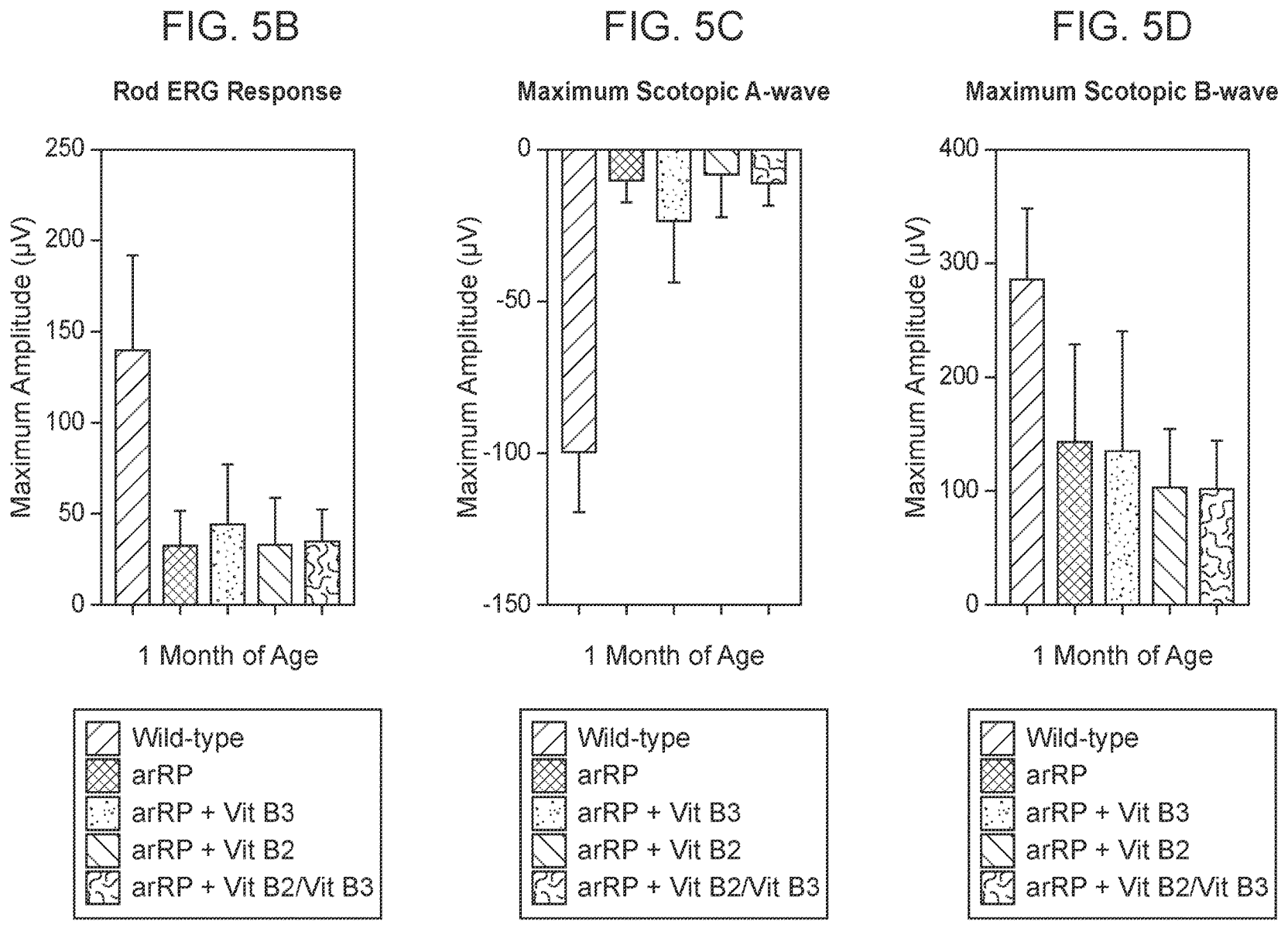

Maximum Scotopic B-wave

1 Month of Age

Wild-type
arRP
arRP + Vit B3
arRP + Vit B2
arRP + Vit B2/Vit B3

FIG. 5C

Maximum Scotopic A-wave

1 Month of Age

Wild-type
arRP
arRP + Vit B3
arRP + Vit B2
arRP + Vit B2/Vit B3

FIG. 5B

Rod ERG Response

1 Month of Age

Wild-type
arRP
arRP + Vit B3
arRP + Vit B2
arRP + Vit B2/Vit B3

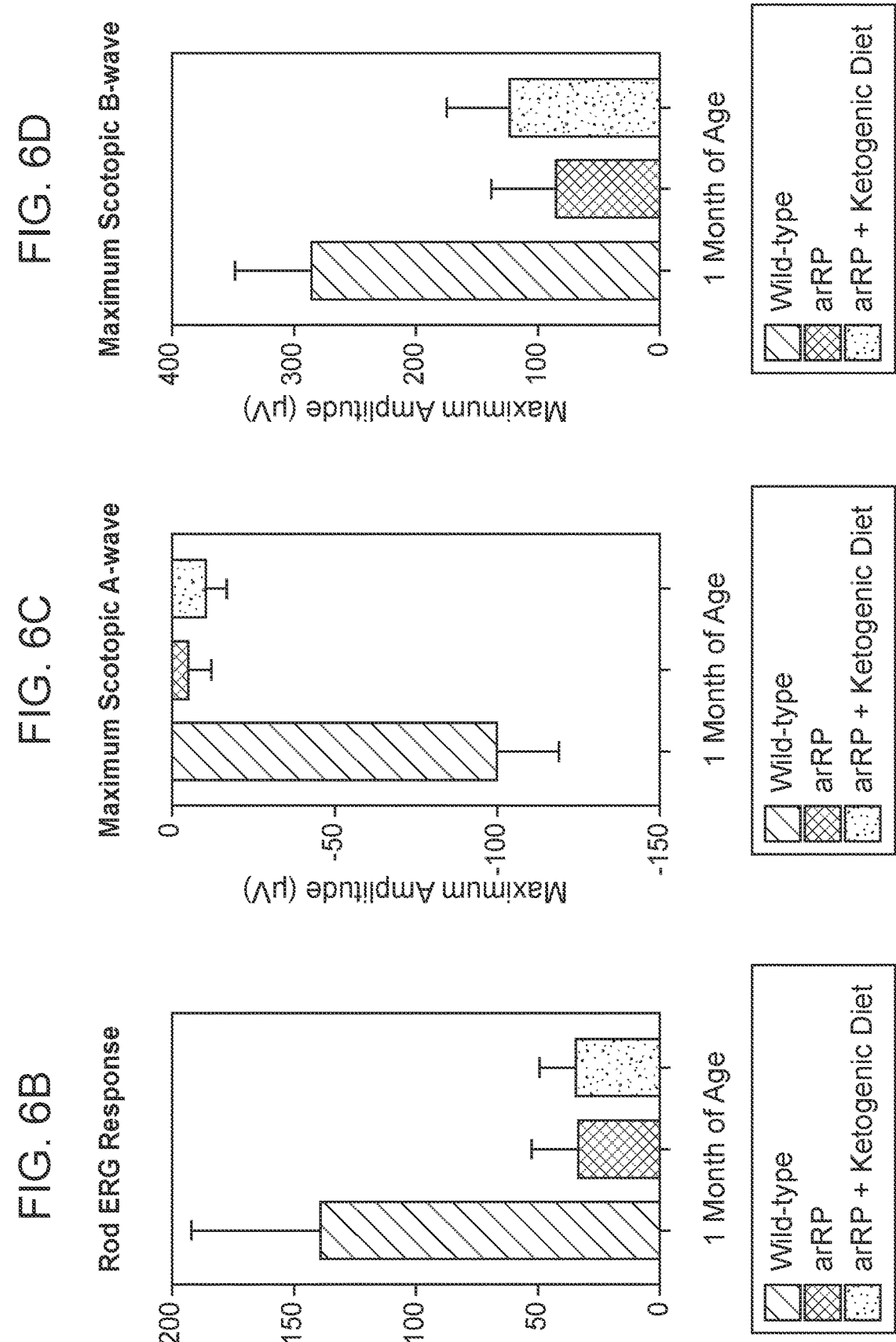

2 Month of Age

1 Month of Age

FIG. 7D

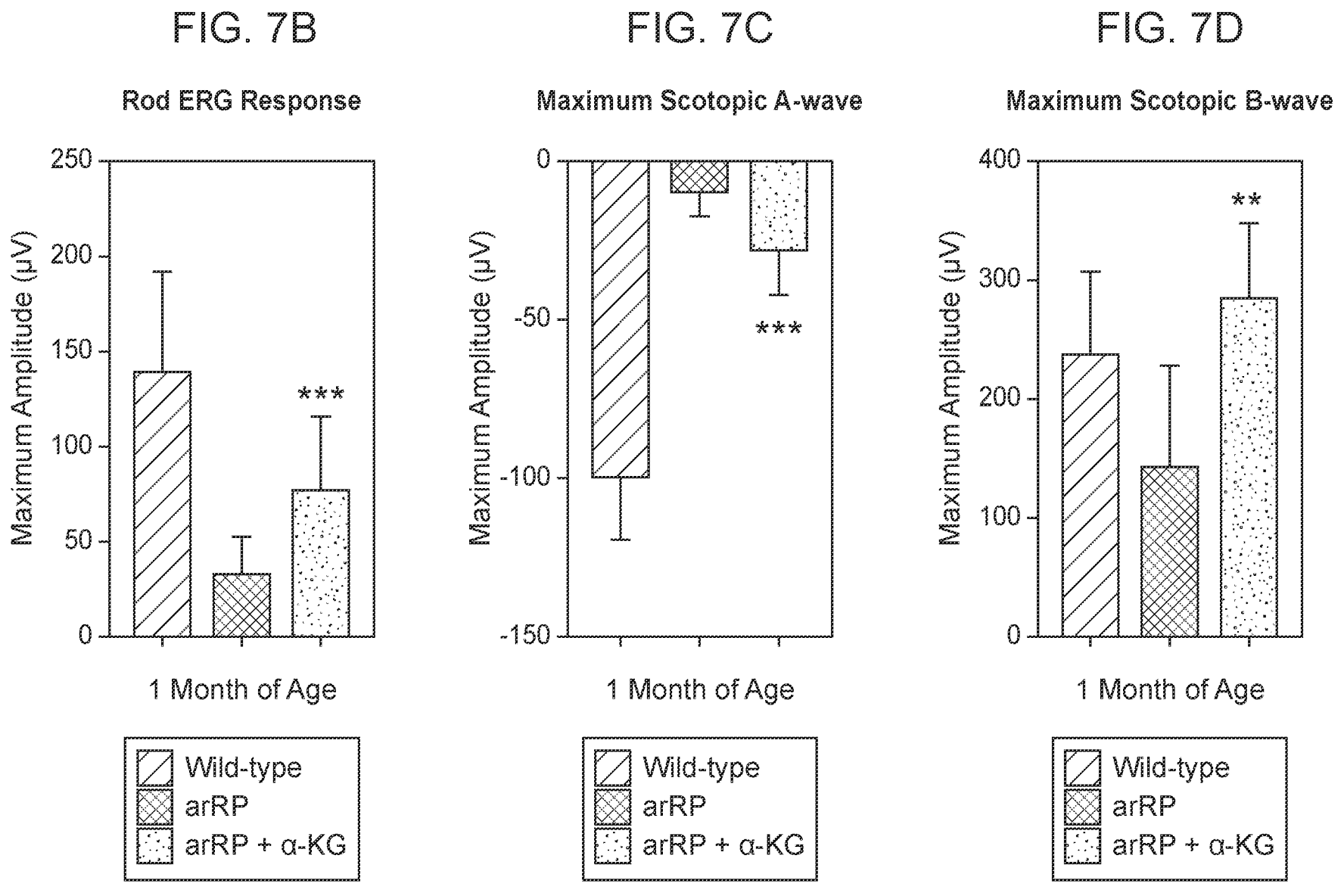

Maximum Scotopic B-wave

Maximum Amplitude (µV)

1 Month of Age

Wild-type
arRP
arRP + α-KG

FIG. 7C

Maximum Scotopic A-wave

Maximum Amplitude (µV)

1 Month of Age

Wild-type
arRP
arRP + α-KG

FIG. 7B

Rod ERG Response

Maximum Amplitude (µV)

1 Month of Age

Wild-type
arRP
arRP + α-KG

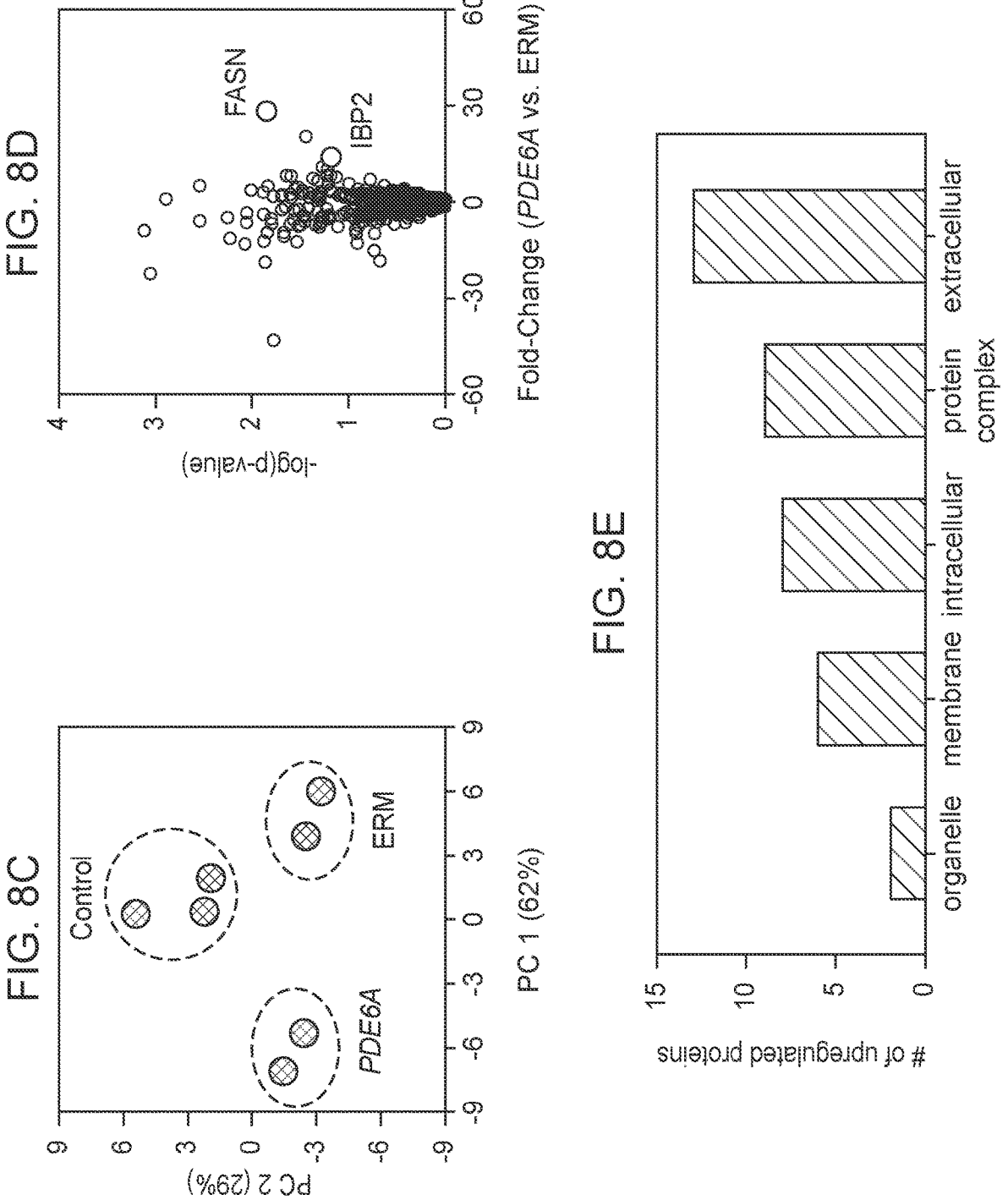

Ontology: Control 90 Retina (545 Proteins)

FIG. 10 (Cont.)

Ontology: PDE6 P15 Retina (164 Proteins)

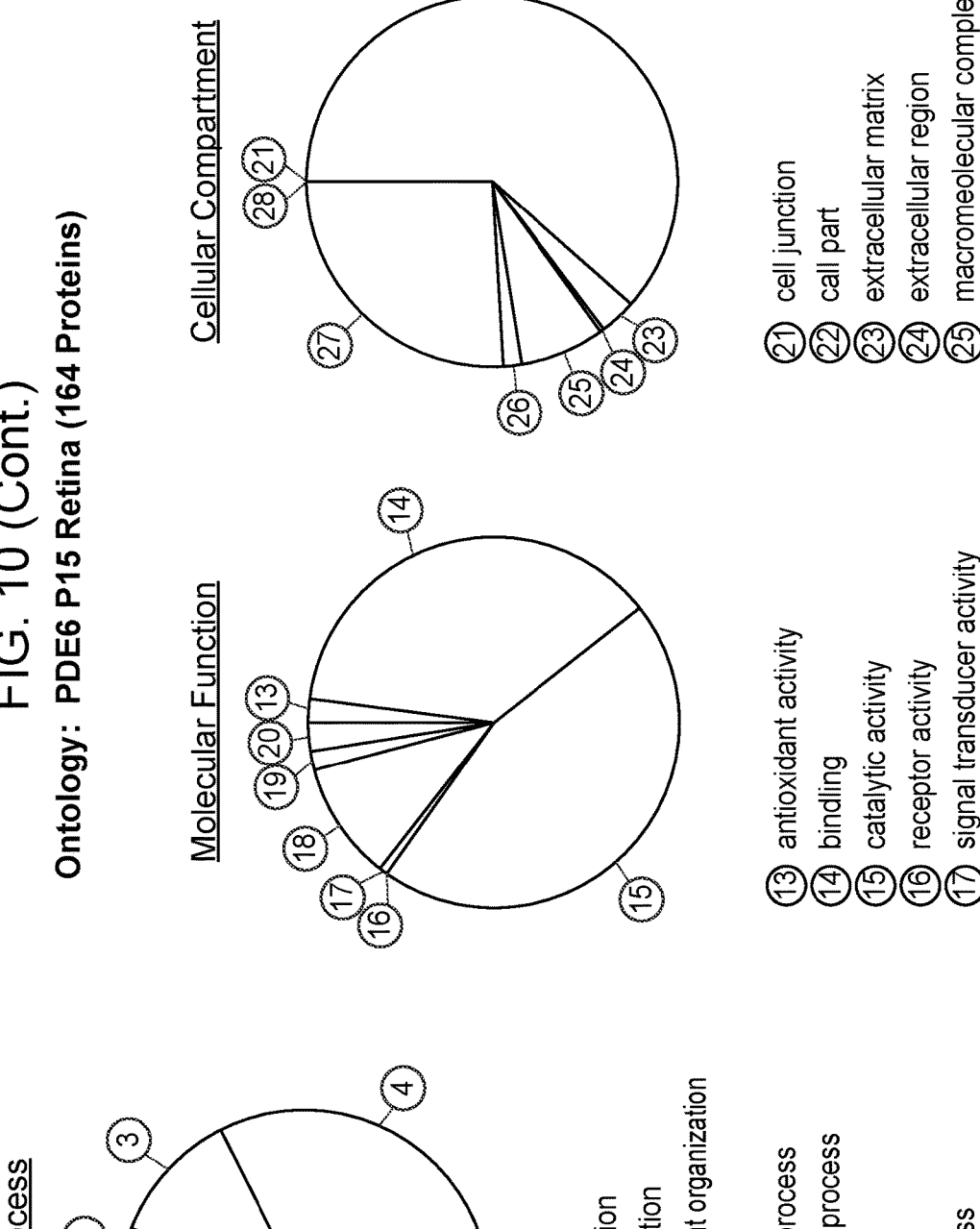

Cellular Compartment

㉑ cell junction
㉒ call part
㉓ extracellular matrix
㉔ extracellular region
㉕ macromeolecular complex
㉖ membrane
㉗ organelle
㉘ synapse Molecular Function ⑬ antioxidant activity
⑭ binding
⑮ catalytic activity
⑯ receptor activity
⑰ signal transducer activity
⑱ structural molecule activity
⑲ translation regulator activity
⑳ transporter activity Biological Process ① biological adhesion
② biological regulation
③ cellular component organization
④ cellular process
⑤ developmental process
⑥ immune system process
⑦ localization
⑧ locomotion
⑨ metabolic process
⑩ multicellular organismal process
⑪ reproduction
⑫ response to stimulus

FIG. 10 (Cont.)

Ontology: PDE6 P28 Retina (419 Proteins)

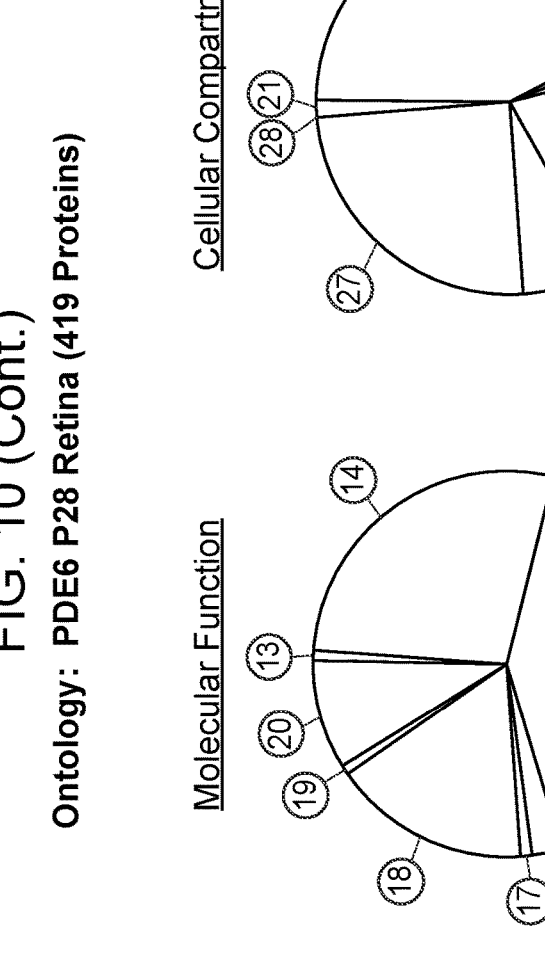

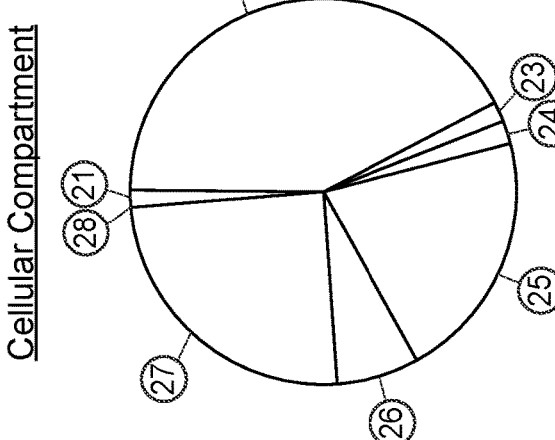

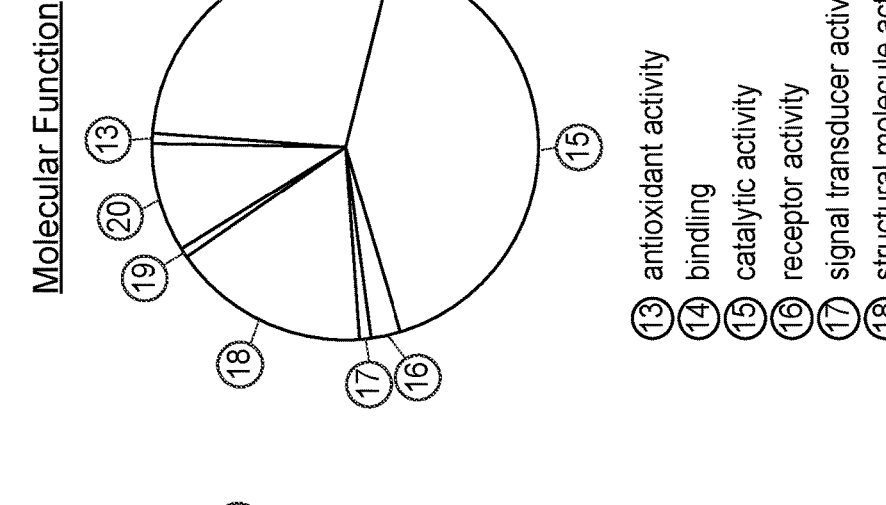

Cellular Compartment

(21) cell junction
(22) call part
(23) extracellular matrix
(24) extracellular region
(25) macromeolecular complex
(26) membrane
(27) organelle
(28) synapse Molecular Function

(13) antioxidant activity
(14) bindling
(15) catalytic activity
(16) receptor activity
(17) signal transducer activity
(18) structural molecule activity
(19) translation regulator activity
(20) transporter activity Biological Process (1) biological adhesion
(2) biological regulation
(3) cellular component organization
(4) cellular process
(5) developmental process
(6) immune system process
(7) localization
(8) locomotion
(9) metabolic process
(10) multicellular organismal process
(11) reproduction
(12) response to stimulus

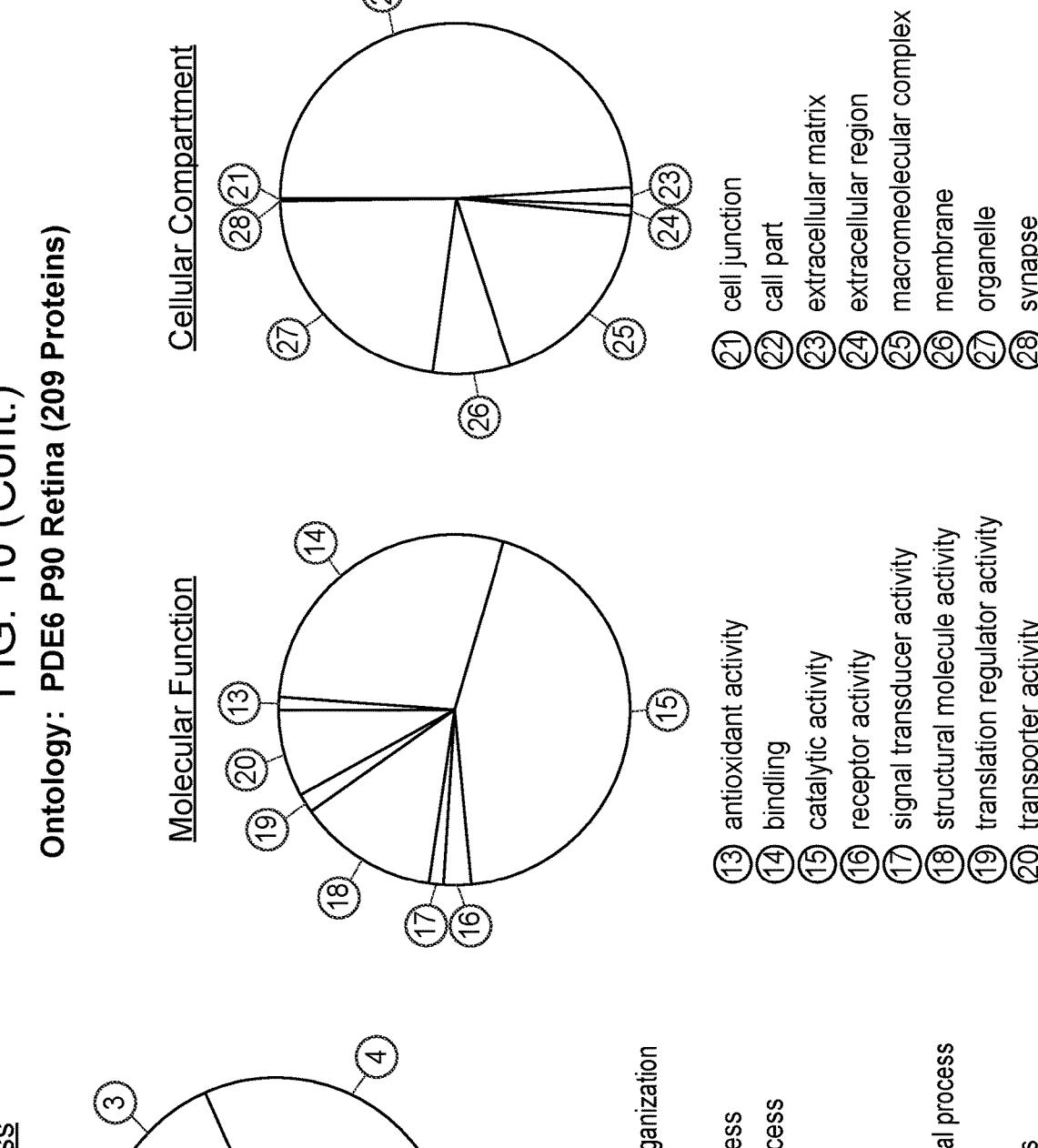

FIG. 10 (Cont.)

Ontology: PDE6 P90 Retina (209 Proteins)

Cellular Compartment

㉑ cell junction
㉒ call part
㉓ extracellular matrix
㉔ extracellular region
㉕ macromeolecular complex
㉖ membrane
㉗ organelle
㉘ synapse Molecular Function ⑬ antioxidant activity
⑭ bindling
⑮ catalytic activity
⑯ receptor activity
⑰ signal transducer activity
⑱ structural molecule activity
⑲ translation regulator activity
⑳ transporter activity Biological Process ① biological adhesion
② biological regulation
③ cellular component organization
④ cellular process
⑤ developmental process
⑥ immune system process
⑦ localization
⑧ locomotion
⑨ metabolic process
⑩ multicellular organismal process
⑪ reproduction
⑫ response to stimulus

FIG. 11

Ontology: Control 90 Retina (100 Proteins)

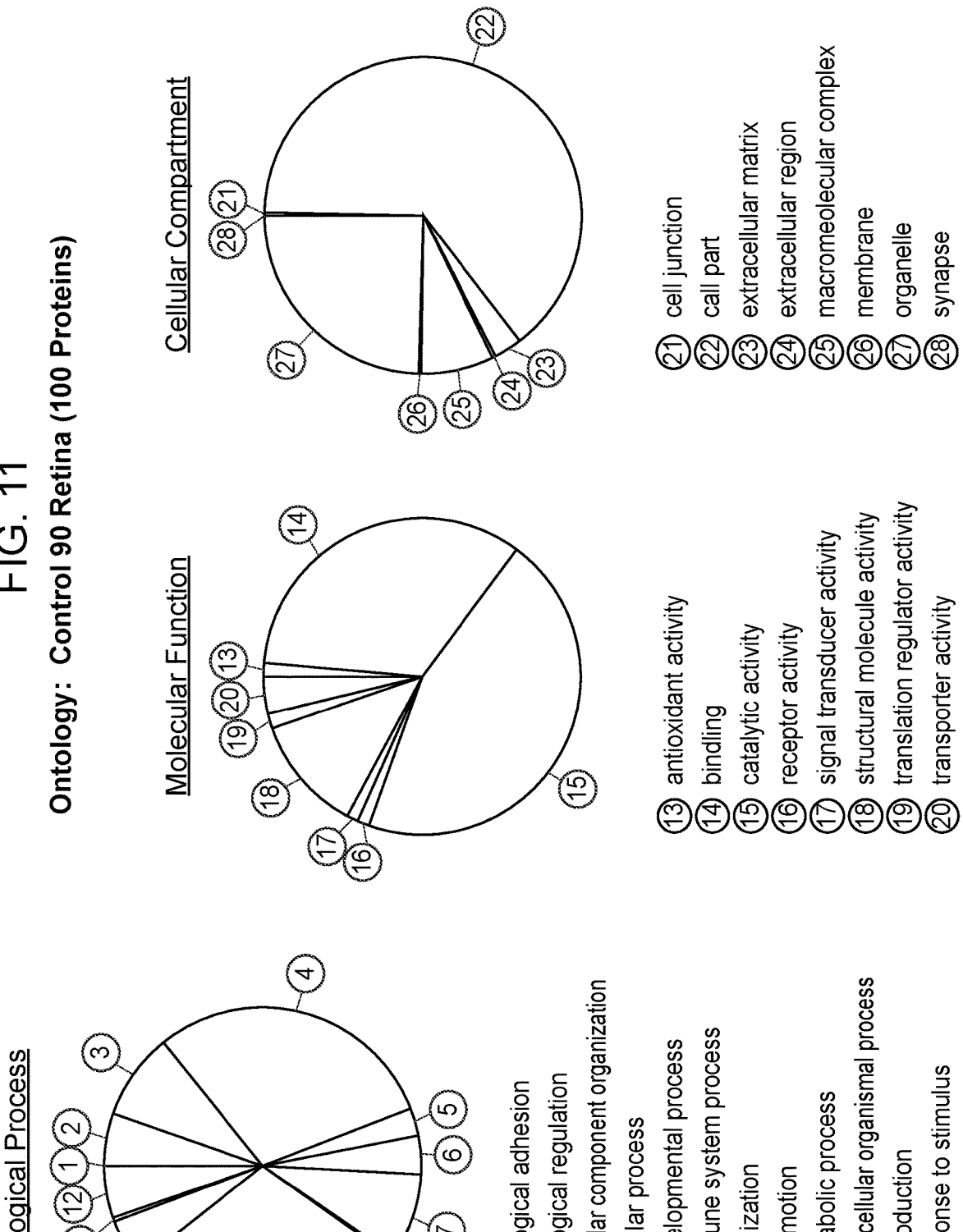

Cellular Compartment

㉑ cell junction
㉒ call part
㉓ extracellular matrix
㉔ extracellular region
㉕ macromeolecular complex
㉖ membrane
㉗ organelle
㉘ synapse

Molecular Function

⑬ antioxidant activity
⑭ bindling
⑮ catalytic activity
⑯ receptor activity
⑰ signal transducer activity
⑱ structural molecule activity
⑲ translation regulator activity
⑳ transporter activity

Biological Process

① biological adhesion
② biological regulation
③ cellular component organization
④ cellular process
⑤ developmental process
⑥ immune system process
⑦ localization
⑧ locomotion
⑨ metabolic process
⑩ multicellular organismal process
⑪ reproduction
⑫ response to stimulus

FIG. 11 (Cont.)

Ontology: PDE6 P15 Retina (568 Proteins)

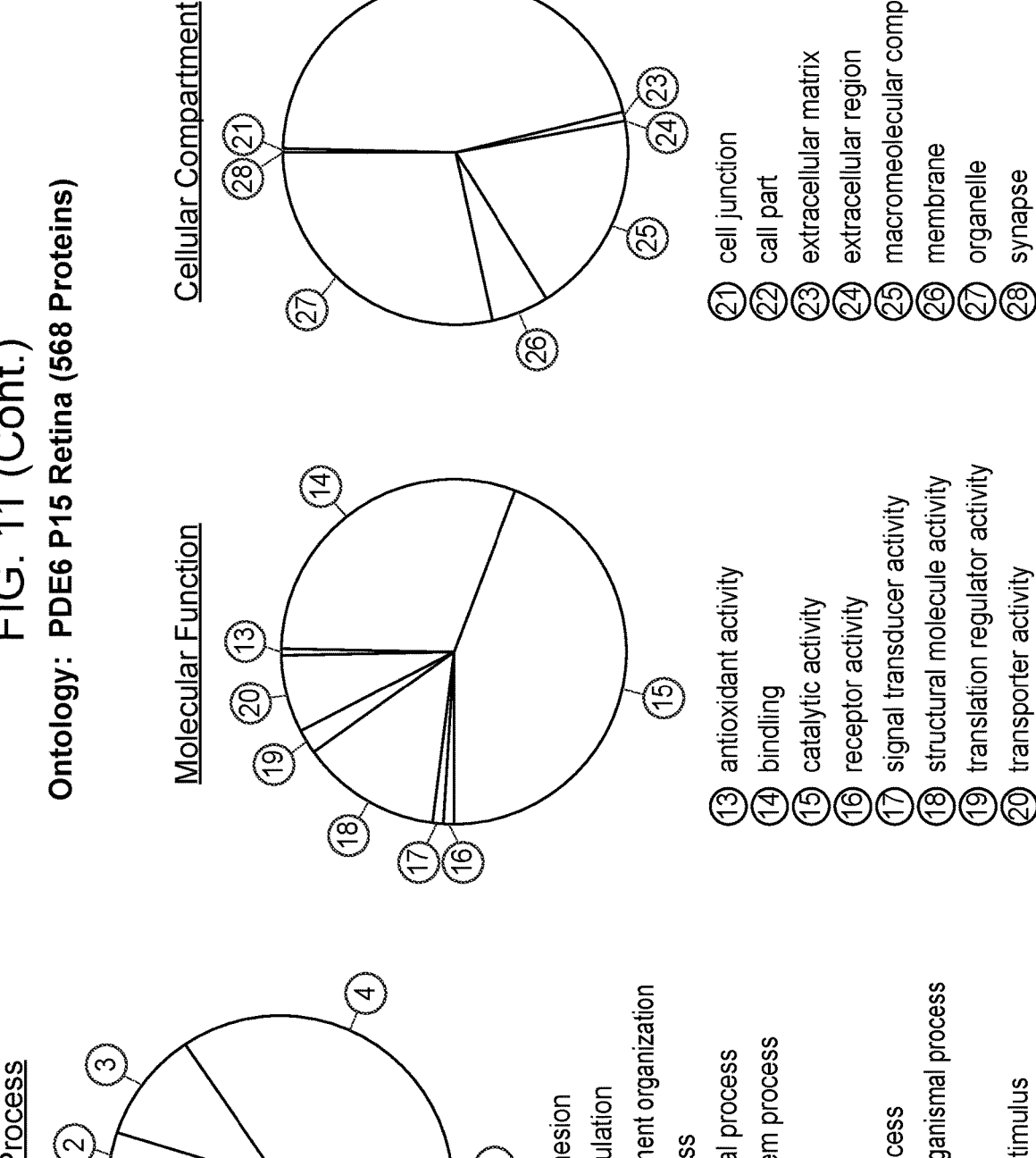

Cellular Compartment

㉑ cell junction
㉒ call part
㉓ extracellular matrix
㉔ extracellular region
㉕ macromeolecular complex
㉖ membrane
㉗ organelle
㉘ synapse

Molecular Function

⑬ antioxidant activity
⑭ bindling
⑮ catalytic activity
⑯ receptor activity
⑰ signal transducer activity
⑱ structural molecule activity
⑲ translation regulator activity
⑳ transporter activity

Biological Process

① biological adhesion
② biological regulation
③ cellular component organization
④ cellular process
⑤ developmental process
⑥ immune system process
⑦ localization
⑧ locomotion
⑨ metabolic process
⑩ multicellular organismal process
⑪ reproduction
⑫ response to stimulus

FIG. 11 (Cont.)

Ontology: PDE6 P28 Retina (40 Proteins)

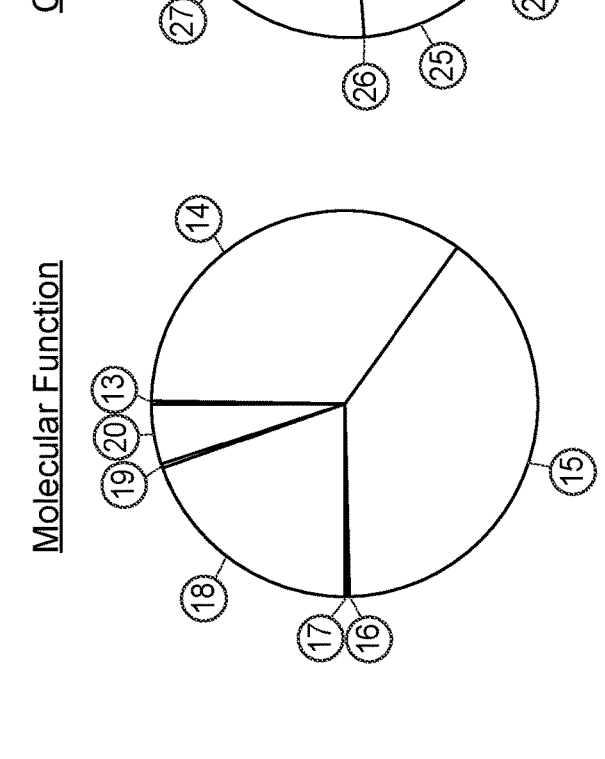

Cellular Compartment

㉑ cell junction
㉒ call part
㉓ extracellular matrix
㉔ extracellular region
㉕ macromeolecular complex
㉖ membrane
㉗ organelle
㉘ synapse Molecular Function ⑬ antioxidant activity
⑭ binding
⑮ catalytic activity
⑯ receptor activity
⑰ signal transducer activity
⑱ structural molecule activity
⑲ translation regulator activity
⑳ transporter activity

Biological Process

① biological adhesion
② biological regulation
③ cellular component organization
④ cellular process
⑤ developmental process
⑥ immune system process
⑦ localization
⑧ locomotion
⑨ metabolic process
⑩ multicellular organismal process
⑪ reproduction
⑫ response to stimulus

FIG. 11 (Cont.)

Ontology: PDE6 P90 Retina (226 Proteins)

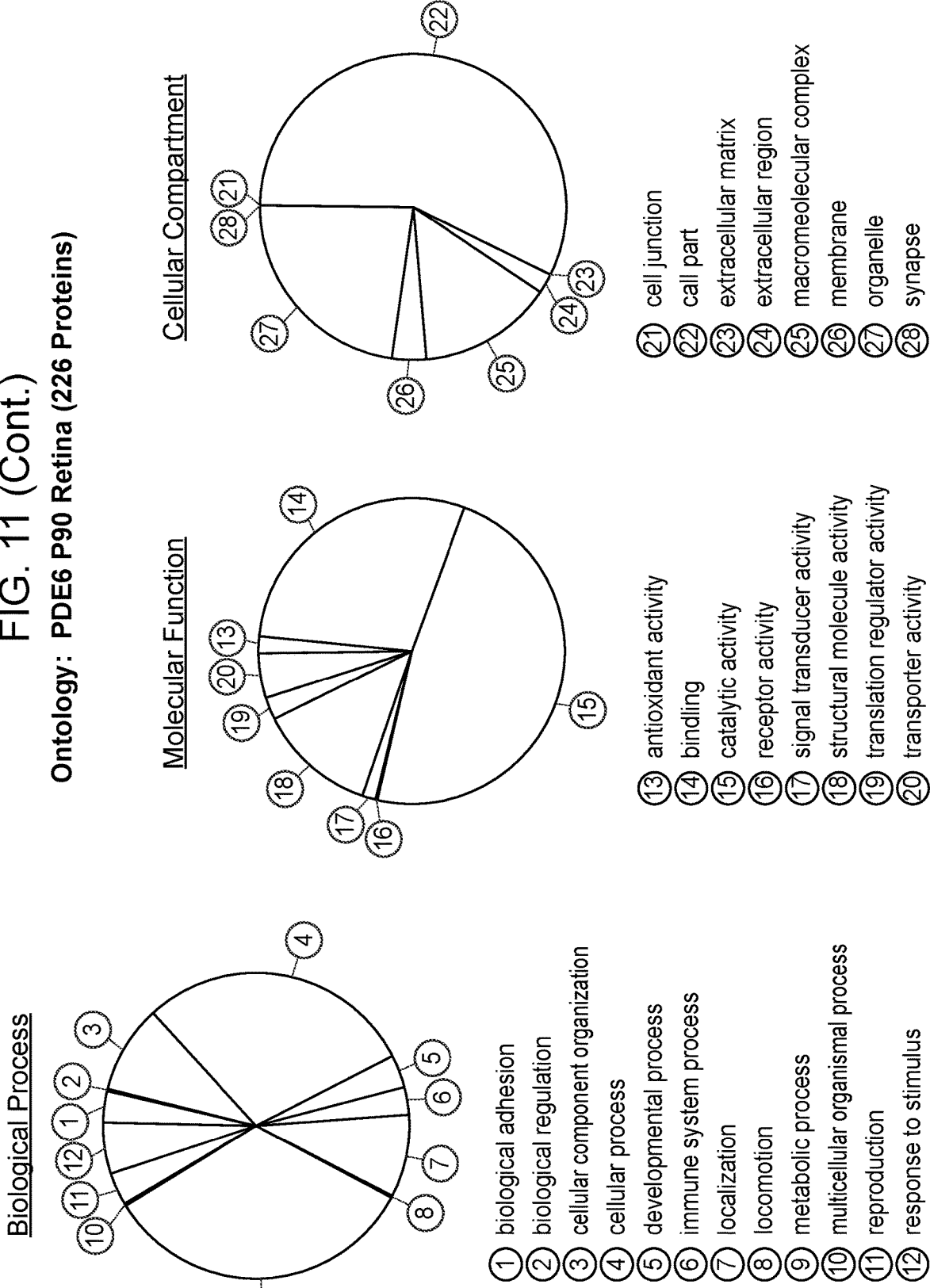

Cellular Compartment

- ㉑ cell junction
- ㉒ call part
- ㉓ extracellular matrix
- ㉔ extracellular region
- ㉕ macromeolecular complex
- ㉖ membrane
- ㉗ organelle
- ㉘ synapse

Molecular Function

- ⑬ antioxidant activity
- ⑭ bindling
- ⑮ catalytic activity
- ⑯ receptor activity
- ⑰ signal transducer activity
- ⑱ structural molecule activity
- ⑲ translation regulator activity
- ⑳ transporter activity

Biological Process

- ① biological adhesion
- ② biological regulation
- ③ cellular component organization
- ④ cellular process
- ⑤ developmental process
- ⑥ immune system process
- ⑦ localization
- ⑧ locomotion
- ⑨ metabolic process
- ⑩ multicellular organismal process
- ⑪ reproduction
- ⑫ response to stimulus

METABOLIC RESCUE OF RETINAL DEGENERATION

STATEMENT REGARDING FEDERALLY SPONSORED RESEARCH OR DEVELOPMENT

This invention was made with government support under contract EY025225 awarded by the National Institutes of Health. The government has certain rights in the invention.

BACKGROUND

Neurodegenerative diseases are debilitating disorders that are caused by the death of neuronal cells, with no known cures available to patients suffering from these conditions. The neurodegenerative disease, retinitis pigmentosa (RP), results from loss of the rod neurons of the retina, and leads to progressive loss of the entire neural retinal network. Although current research advances for RP and other related neurodegenerative disorders have focused on gene therapy approaches, these gene therapy approaches are costly, as they involve targeting each individual genetic mutation (e.g. >130 RHO mutations can lead to RP). There remains a need for better treatments for patients with neuronal degeneration, regardless of their specific genetic mutation, to prevent neuronal cell death.

SUMMARY

Methods are provided for treating and diagnosing diseases and disorders associated with retinal degeneration, such as retinitis pigmentosa. Dietary supplementation with specific metabolites and vitamins can prolong vision and provide a neuroprotective effect. In particular, dietary supplementation with α-ketoglutarate, or a derivative thereof, significantly prolongs photoreceptor cell survival and visual function. In addition, dietary supplementation with B vitamins and a ketogenic diet also improves photoreceptor cell survival and delays disease progression in some cases. Additionally, compositions, methods, and kits are provided for diagnosing a subject with retinitis pigmentosa based on expression levels of vitreous biomarkers.

In one aspect, a method of treating a subject for a disease or disorder associated with retinal degeneration is provided, the method comprising administering to the subject in need thereof a therapeutically effective amount of α-ketoglutarate or a derivative thereof.

In certain embodiments, a derivative of α-ketoglutarate is administered that is cell permeable. Exemplary cell permeable monoester derivatives of α-ketoglutarate include, without limitation, α-ketoglutarate benzyl ester, α-ketoglutarate octyl ester, and α-ketoglutarate trifluoromethyl benzyl (TFMB) ester.

In certain embodiments, the method further comprises administering a nutritional supplement comprising vitamin A, vitamin B2, vitamin B3, retinyl palmitate, docosahexaenoic acid (DHA), lutein, or a combination thereof. In some embodiments, the nutritional supplement comprises vitamin B2, vitamin B3, or a combination thereof. In some embodiments, the nutritional supplement is administered separately, sequentially, or simultaneously with the α-ketoglutarate or the derivative thereof.

In certain embodiments, the method further comprises putting the subject on a ketogenic diet.

In certain embodiments, the subject is mammalian. In some embodiments, the subject is a human.

In certain embodiments, the disease is retinitis pigmentosa. In some embodiments, the subject has at least one mutation linked with retinitis pigmentosa. In some embodiments, the mutation is in a gene selected from the group consisting of RPY, RP1, RP2, RPGR, PRPH2, RP9, IMPDH1, PRPF31, CRB1, PRPF8, TULP1, CA4, HPRPF3, ABCA4, EYS, CERKL, FSCN2, TOPORS, SNRNP200, SEMA4A, PROD, NR2E3, MERTK, USH2A, PROM1, KLHL7, CNGB1, BEST1, TTC8, C2orf71, ARL6, ZNF513, DHDDS, BEST1, PRPH2, LRAT, SPATA7, CRX, and RPGR.

In certain embodiments, the α-ketoglutarate or the derivative thereof is administered orally.

In certain embodiments, the method further comprises separately, sequentially, or simultaneously administering at least one neuroprotective agent to the subject.

In another aspect, a method for treating a subject for a disease or disorder associated with retinal degeneration is provided, the method comprising putting the subject on a ketogenic diet that reduces the subject's daily intake of food containing carbohydrates and increases the subject's daily intake of fat. In some embodiments, the ketogenic diet limits carbohydrate intake of the subject to 10-15 grams of carbohydrate per day. Preferably, the ketogenic diet provides other nutrients at levels in accordance with United States Recommended Daily Allowances (USRDA) guidelines.

In certain embodiments, the subject stays on the diet for at least 6 months, 1 year, 2 years, 3 years, 4 years, 5 years, or longer. In some embodiments, the subject stays on the ketogenic diet for as long as the ketogenic diet is beneficial for treating the disease or disorder associated with retinal degeneration in the subject.

In another aspect, a protein selected from the group consisting of rhodopsin, guanine nucleotide-binding protein alpha subunit and beta subunit, phosducin, cyclic nucleotide-gated channel beta 1, rhodopsin kinase, recoverin, and S-arrestin for use as a biomarker in diagnosing retinitis pigmentosa is provided.

In another aspect, an in vitro method of diagnosing a subject with retinitis pigmentosa is provided, the method comprising: a) obtaining a vitreous sample from the subject; b) measuring one or more biomarkers in the vitreous sample, wherein the biomarkers are selected from the group consisting of rhodopsin, guanine nucleotide-binding protein alpha subunit and beta subunit, phosducin, cyclic nucleotide-gated channel beta 1, rhodopsin kinase, recoverin, and S-arrestin; and c) diagnosing the subject, wherein increased levels of rhodopsin, guanine nucleotide-binding protein alpha subunit and beta subunit, phosducin, cyclic nucleotide-gated channel beta 1, rhodopsin kinase, recoverin, and S-arrestin in the vitreous sample compared to reference values ranges for levels of the biomarkers in a control sample indicate the subject has retinitis pigmentosa.

In certain embodiments, the level of a single biomarker, at least 2 biomarkers, at least 3 biomarkers, at least 4 biomarkers, or all the biomarkers selected from the group consisting of rhodopsin, guanine nucleotide-binding protein alpha subunit and beta subunit, phosducin, cyclic nucleotide-gated channel beta 1, rhodopsin kinase, recoverin, and S-arrestin are measured.

In certain embodiments, the method further comprises administering to the subject a therapeutically effective amount of α-ketoglutarate or a derivative thereof if the subject is diagnosed with retinitis pigmentosa.

In certain embodiments, the method further comprises administering a nutritional supplement comprising vitamin A, vitamin B2, vitamin B3, retinyl palmitate, docosahexaenoic acid (DHA), lutein, or a combination thereof if the subject is diagnosed with retinitis pigmentosa. In some embodiments, the nutritional supplement comprises vitamin B2, vitamin B3, or a combination thereof.

In certain embodiments, the method further comprises putting the subject on a ketogenic diet if the subject is diagnosed with retinitis pigmentosa.

In another aspect, a method of monitoring progression of retinitis pigmentosa in a subject is provided, the method comprising: a) obtaining a first vitreous sample from the subject at a first time point and a second vitreous sample from the subject later at a second time point; b) measuring one or more biomarkers in the first vitreous sample and the second vitreous sample, wherein the biomarkers are selected from the group consisting of rhodopsin, guanine nucleotide-binding protein alpha subunit and beta subunit, phosducin, cyclic nucleotide-gated channel beta 1, rhodopsin kinase, recoverin, and S-arrestin; and c) evaluating progression of retinitis pigmentosa in the subject wherein detection of increased levels of one or more biomarkers selected from the group consisting of rhodopsin, guanine nucleotide-binding protein alpha subunit and beta subunit, phosducin, cyclic nucleotide-gated channel beta 1, rhodopsin kinase, recoverin, and S-arrestin in the second vitreous sample compared to the levels of the biomarkers in the first vitreous sample indicates that the subject is worsening, and detection of decreased levels of one or more biomarkers selected from the group consisting of rhodopsin, guanine nucleotide-binding protein alpha subunit and beta subunit, phosducin, cyclic nucleotide-gated channel beta 1, rhodopsin kinase, recoverin, and S-arrestin in the second vitreous sample compared to the levels of the biomarkers in the first vitreous sample indicates that the subject is improving.

In another aspect, a method of monitoring efficacy of a treatment for a disease or disorder associated with retinal degeneration is provided, the method comprising: a) obtaining a first vitreous sample from a subject before the subject undergoes the treatment and a second vitreous sample from the subject after the subject undergoes the treatment; b) measuring one or more biomarkers in the first vitreous sample and the second vitreous sample, wherein the biomarkers are selected from the group consisting of rhodopsin, guanine nucleotide-binding protein alpha subunit and beta subunit, phosducin, cyclic nucleotide-gated channel beta 1, rhodopsin kinase, recoverin, and S-arrestin; and c) evaluating progression of retinitis pigmentosa in the subject wherein detection of increased levels of one or more biomarkers selected from the group consisting of rhodopsin, guanine nucleotide-binding protein alpha subunit and beta subunit, phosducin, cyclic nucleotide-gated channel beta 1, rhodopsin kinase, recoverin, and S-arrestin in the second vitreous sample compared to the levels of the biomarkers in the first vitreous sample indicates that the subject is worsening or not responding to the treatment, and detection of decreased levels of one or more biomarkers selected from the group consisting of rhodopsin, guanine nucleotide-binding protein alpha subunit and beta subunit, phosducin, cyclic nucleotide-gated channel beta 1, rhodopsin kinase, recoverin, and S-arrestin in the second vitreous sample compared to the levels of the biomarkers in the first vitreous sample indicates that the subject is improving.

In certain embodiments, the treatment comprises administering a therapeutically effective amount of α-ketoglutarate or a derivative thereof.

In certain embodiments, the treatment comprises administering a nutritional supplement comprising vitamin A, vitamin B2, vitamin B3, retinyl palmitate, docosahexaenoic acid (DHA), lutein, or a combination thereof. In some embodiments, the nutritional supplement comprises vitamin B2, vitamin B3, or a combination thereof.

In certain embodiments, the treatment comprises putting the subject on a ketogenic diet.

In another aspect, a composition comprising α-ketoglutarate or a derivative thereof for treatment of retinitis pigmentosa is provided. In certain embodiments, the composition comprises an α-ketoglutarate derivative that is cell permeable Exemplary cell permeable monoester derivatives of α-ketoglutarate include, without limitation, α-ketoglutarate benzyl ester, α-ketoglutarate octyl ester, and α-ketoglutarate trifluoromethyl benzyl (TFMB) ester. In some embodiments, the composition further comprises a pharmaceutically acceptable excipient.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

(FIG. 1A) Pedigree of a family with autosomal recessive retinitis pigmentosa (arRP) caused by mutations in the PDE6A gene. The proband is denoted by the arrow. (FIGS. 1B-1C) Fundus autofluorescence (488 nm) of the proband (II:5) revealed confluent areas of hypo-autofluorescence, suggesting RPE loss throughout the periphery, and a central ring of hyper-autofluorescence overlying the parafovea. (FIG. 1D) Spatially corresponding SD-OCT scans through the fovea confirmed marked peripheral outer retinal thinning and RPE loss. The fovea was relatively preserved, with a distinguishable ellipsoid zone. (FIGS. 1E-1F) Fundus autofluorescence of the affected brother (II:4) revealed similar confluent areas of hypo-autofluorescence and a central ring of hyper-autofluorescence overlying the parafovea. (FIG. 1G) Spatially corresponding SD-OCT scans showed similar marked peripheral outer retinal thinning and RPE loss.

(FIG. 2A) Timeline of the clinical disease presentation in $Pde6\alpha^{D670G}$ mice. (FIG. 2B) Histological analysis of $Pde6\alpha^{D670G}$ mouse retinas at early- (P11), mid- (P30) and late- (P72) stage disease compared to a wild-type mouse at (P12) shows loss of the ONL photoreceptor cells over time. (FIG. 2C) Maximum scotopic electroretinography (ERG) shows an early loss of the photoreceptor a-wave at one month of age in $Pde6\alpha^{D670G}$ mice (blue and green) compared to a wild-type control (red), and complete loss of the global visual response between 2-3 months of age. (FIG. 2D) Infrared (IR; top panels) and autofluorescence (bottom panels) imaging shows increased hyperfluorescence in the $Pde6\alpha^{D670G}$ mice by 5 months of age compared to a wild-type control (far left), indicative of RPE atrophy. RPE, retinal pigment epithelium; ONL, outer nuclear layer; INL, inner nuclear layer; GCL, ganglion cell layer.

(FIG. 3A) Protein spectral counts were analyzed 1-way ANOVA followed by hierarchical clustering. A total of 1067 proteins were differentially-expressed in the Pde6α$^{D670G}$ vitreous and retina samples compared to controls (p<0.05). Results are represented as a heatmap and display protein expression levels on a logarithmic scale. Orange indicates high expression while dark green/black indicates low or no expression. There were 446 proteins that were downregulated in the Pde6α$^{D670G}$ retina that were upregulated in the Pde6α$^{D670G}$ vitreous. Gene ontology (GO) categorization of the 446 protein biomarkers by (FIG. 3B) cellular compartment and (FIG. 3C) biological process. (FIG. 3D) Pathway representation of the 446 protein biomarkers in the Pde6α$^{D670G}$ vitreous. Pathways are ranked by their fold-enrichment obtained from the Mann-Whitney U Test. Metabolic pathways are bold-faced.

FIGS. 5A-5D show that replenishing oxidative phosphorylation with oral supplementation of metabolites provides a mild, but variable, rescue of visual function in the arRP preclinical mouse. (FIG. 5A) Representative traces of the scotopic 0.1 dim-light rod-specific electroretinography (ERG; left) shows some rescue of rod photoreceptor cell response in Pde6α$^{D670G}$ mice treated with vitamin B2 supplementation (purple), but not mice treated with vitamin B$_3$ supplementation (red) in comparison to wild-type controls (black) and untreated Pde6α$^{D670G}$ mice (gray) at one month of age. Representative traces of the scotopic 1.0 global electroretinography (ERG; left) shows some rescue of the global visual response in Pde6α$^{D670G}$ mice treated with vitamin B$_2$ supplementation (purple), but not mice treated with vitamin B$_3$ supplementation (red) in comparison to wild-type controls (black) and untreated Pde6α$^{D670G}$ mice (gray) at one month of age. Quantification of ERGs from a cohort of mice shows no significant visual rescue of (FIG. 5B) the rod photoreceptor cell response, (FIG. 5C) the maximum scotopic a-wave response, or (FIG. 5D) the maximum scotopic b-wave response in mice treated with vitamin B$_2$ supplementation (purple), vitamin B$_3$ supplementation (red), or a combination of both vitamins (red/purple stripes) in comparison with wild-type controls (black) or untreated Pde6α$^{D670G}$ mice (gray) at one month of age.

FIGS. 6A-6F show that restoration of the tricarboxylic acid (TCA) cycle with the ketogenic diet rescues photoreceptor cell survival in the arRP preclinical mouse. (FIG. 6A) Representative traces of the scotopic 0.1 dim-light rod-specific electroretinography (ERG; left) shows no significant difference in the rod photoreceptor cell response in Pde6α$^{D670G}$ mice treated with the ketogenic diet (green) in comparison to untreated Pde6α$^{D670G}$ mice (gray) at one month of age. Representative traces of the scotopic 1.0 global electroretinography (ERG; left) shows some rescue of the global visual response in Pde6α$^{D670G}$ mice treated with the ketogenic diet (green) in comparison to wild-type controls (black) and untreated Pde6α$^{D670G}$ mice (gray) at one month of age. Quantification of ERGs from a cohort of mice shows no significant visual rescue of (FIG. 6B) the rod photoreceptor cell response, (FIG. 6C) the maximum scotopic a-wave response, or (FIG. 6D) the maximum scotopic b-wave response in mice treated with the ketogenic diet (green) in comparison with wild-type controls (black) or untreated Pde6α$^{D670G}$ mice (gray) at one month of age, although there was a trend toward an increased a- and b-wave maximal response. N=(FIGS. 6E-6F) Histological analysis of the retinas of untreated Pde6α$^{D670G}$ mice (left)

Figure 1A:
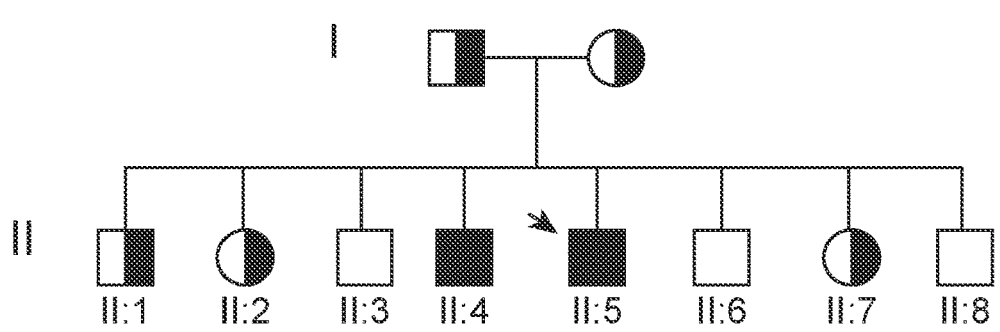
FIGS. 1A-1G show two patients with autosomal recessive Retinitis Pigmentosa carrying mutations in PDE6A.

compared to treated Pde6α$^{D670G}$ mice (right) shows a significant increase in the thickness of the outer nuclear layer (ONL) by number of photoreceptor cell nuclei in mice treated with the ketogenic diet at two months of age. ***, p<0.001. GCL, ganglion cell layer; INL, inner nuclear layer; RPE, retinal pigment epithelium.

FIGS. 7A-7F show that restoration of the tricarboxylic acid (TCA) cycle with oral supplementation of alpha-keto-glutarate rescues photoreceptor cell survival and visual function in the arRP preclinical mouse. (FIG. 7A) Representative traces of the scotopic 0.1 dim-light rod-specific electroretinography (ERG; left) shows a rescue of the rod photoreceptor cell response in Pde6α$^{D670G}$ mice treated with alpha-ketoglutarate supplementation (blue) in comparison to untreated Pde6α$^{D670G}$ mice (gray) and wild-type controls (black) at one month of age. Representative traces of the scotopic 1.0 global electroretinography (ERG; left) shows rescue of the global visual response in Pde6α$^{D670G}$ mice treated alpha-ketoglutarate supplementation (blue) in comparison to untreated Pde6α$^{D670G}$ mice (gray) and wild-type controls (black) at one month of age. Quantification of ERGs from a cohort of mice shows significant visual rescue of (FIG. 7B) the rod photoreceptor cell response, (FIG. 7C) the maximum scotopic a-wave response, and (FIG. 7D) the maximum scotopic b-wave response in mice treated with alpha-ketoglutarate supplementation (blue) in comparison with wild-type controls (black) or untreated Pde6α$^{D670G}$ mice (gray) at one month of age. , p<0.01; *, p<0.001. (FIGS. 7E-7F) Histological analysis of the retinas of untreated Pde6α$^{D670G}$ mice (left) compared to treated Pde6α$^{D670G}$ mice (right) shows a significant increase in the thickness of the outer nuclear layer (ONL) by number of photoreceptor cell nuclei in mice treated with alpha-keto-glutarate supplementation (blue) at one month of age. ****, p<0.0001. GCL, ganglion cell layer; INL, inner nuclear layer; RPE, retinal pigment epithelium.

FIGS. 8A-8E show validation of Pde6α$^{D670G}$ vitreous biomarkers in a human retinal degeneration case. (FIGS. 8A-8B) Pars plana vitrectomy and epiretinal membrane removal procedure for an PDE6A (arRP) patient (II:5 in FIG. 1). A vitreous biopsy was collected from this patient and the affected brother. Protein content was analyzed by LC-MS/MS. (FIG. 8C) Principal component analysis (PCA) of the proteomics data. The score plot of PC1 and PC2 shows separation between PDE6A cases (orange), ERM (blue), and IMH controls (green) based on protein expression levels that were significantly different between the two groups. (FIG. 8D) Protein spectral counts were analyzed by 1-way ANOVA. Results are represented as a volcano plot. The horizontal axis (x-axis) displays the log 2 fold-change value (PDE6A vs. ERM) and the vertical axis (y-axis) displays the noise-adjusted signal as the −log 10 (p-value) from the 1-way ANOVA analysis. Increased levels of FASN and IBP2 are denoted by the orange circles. There were 37 upregulated proteins in PDE6A vitreous and 50 downregulated proteins at the p<0.05 level. (FIG. 8E) Gene ontology analysis categorized the 37 significantly-upregulated proteins by their cellular compartment.

Figure 9:
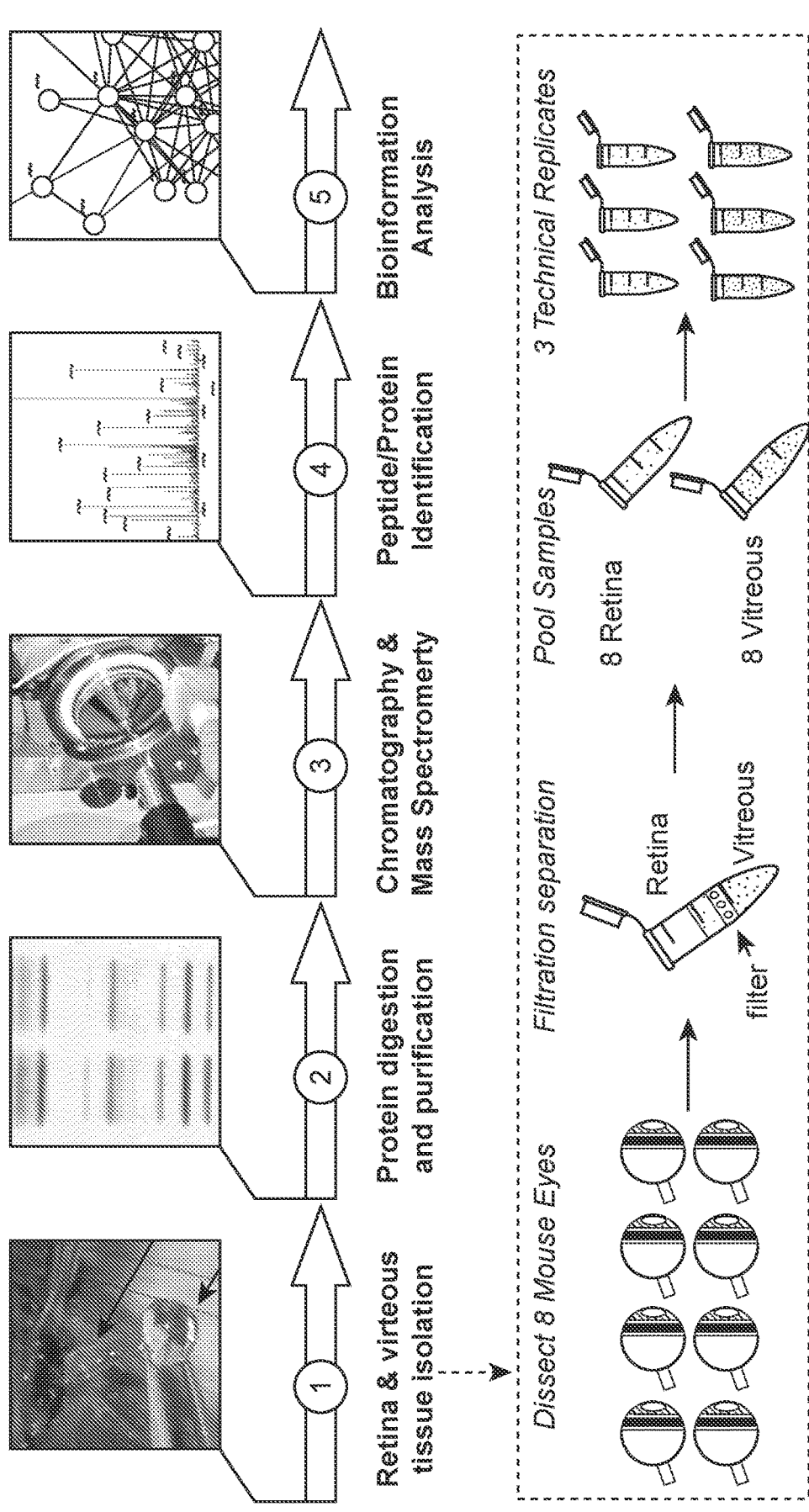

FIG. 9 shows proteomic analysis pipeline. The retina and vitreous were dissected from wild-type and Pde6α$^{D670G}$ mouse eyes. Proteins were precipitated from dissected samples and digested with trypsin. Peptides were analyzed by liquid chromatography-tandem mass spectrometry. Identifications were returned, and proteins represented by two or more peptides were used in further differential expression, ontology, and pathway analysis.

Figure 10:
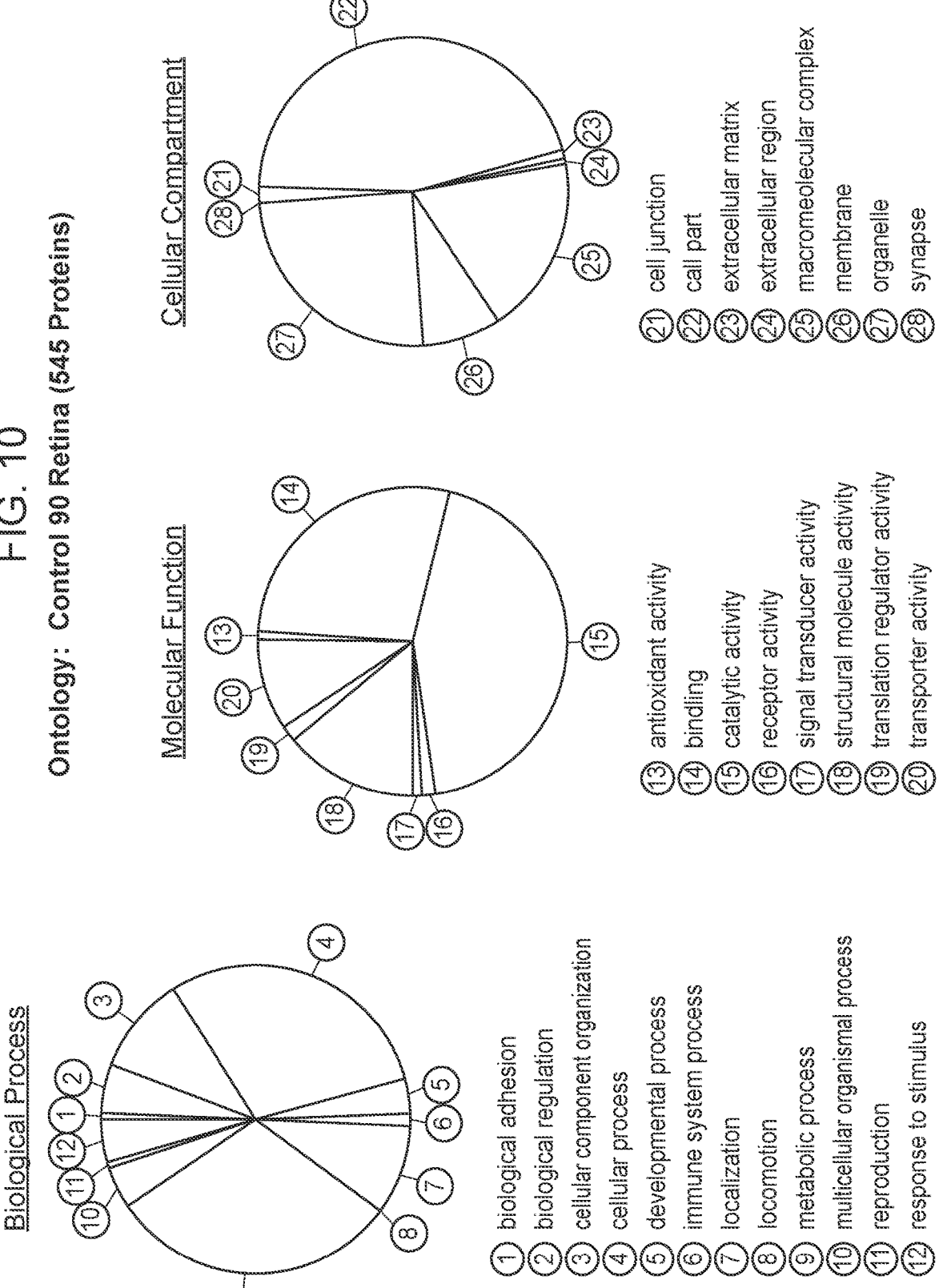

FIG. 10 shows gene ontology analysis of the Pde6α$^{D670G}$ retina proteomes at different stages of degeneration. Identified retinal proteins from the wild-type and Pde6α$^{D670G}$ mice at P15, P28, and P90. Gene ontology analysis categorized each protein group by biological process, molecular function, and cellular compartment.

FIG. 11 shows gene ontology analysis of the Pde6α$^{D670G}$ vitreous proteomes at different stages of degeneration. Identified vitreous proteins from the wild-type and Pde6α$^{D670G}$ mice at P15, P28, and P90. Gene ontology analysis categorized each protein group by biological process, molecular function, and cellular compartment.

DETAILED DESCRIPTION

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In the description that follows, a number of terms conventionally used in the field are utilized. In order to provide a clear and consistent understanding of the specification and claims, and the scope to be given to such terms, the following definitions are provided.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is human.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations. The definition also includes sample that have been enriched for particular types of molecules, e.g., nucleic acids, polypeptides, etc.

The term "diagnosis" is used herein to refer to the identification of a molecular or pathological state, disease or condition.

The term "prognosis" is used herein to refer to the prediction of the likelihood of disease progression (e.g., progression of retinal degeneration), including loss of cone and/or rod photoreceptor cells, loss of vision, etc.

The term "prediction" is used herein to refer to the act of foretelling or estimating, based on observation, experience, or scientific reasoning. In one example, a physician may predict the likelihood that a patient will survive.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides/epitopes). In some embodiments, the affinity of one molecule for another molecule to which it specifically binds is characterized by a KD (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower KD.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member).

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

The term "disease or disorder associated with retinal degeneration" includes any disease or disorder causing degeneration of rod photoreceptors and/or cone photoreceptors and loss of vision. Diseases and disorders causing retinal degeneration include, but are not limited to, retinitis pigmentosa, Usher syndrome, Alport's syndrome, Kearns-Sayre syndrome, abetalipoproteinemia, McLeod syndrome, Bardet-Biedl syndrome, neurosyphilis, toxoplasmosis and Refsum's disease.

Retinitis pigmentosa is a disorder that is characterized by progressive loss of vision associated with degeneration of rod and cone photoreceptor cells in the eye. The presence of dark pigment deposits in the retina or a mottled retinal pigment epithelium, bone spicules in the fundus, and attenuation of blood vessels in the retina is common in individuals suffering from retinitis pigmentosa. Individuals with retinitis pigmentosa also experience visual changes including, but not limited to, nyctalopia (night blindness), loss of peripheral vision (tunnel vision), photophobia (aversion to bright lights), photopsia (blinking/shimmering lights within the visual field), poor color discrimination, loss of central vision, slow adjustment to changes in light levels, and eventual blindness. See, e.g., Heckenlively et al., Clinical findings and common symptoms in retinitis pigmentosa. Am. J. Ophthalmol. 105(5): 504-511 (1988).

At least 260 genes, including numerous candidate mutations (over 3000) in recessive, dominant, and X-linked alleles have been linked to retinitis pigmentosa. Retinitis pigmentosa may be associated with one or more mutations in genes including, without limitation, RPY, RP1, RP2, RPGR, PRPH2, RP9, IMPDH1, PRPF31, CRB1, PRPF8, TULP1, CA4, HPRPF3, ABCA4, EYS, CERKL, FSCN2, TOPORS, SNRNP200, SEMA4A, PRCD, NR2E3, MERTK, USH2A, PROM1, KLHL7, CNGB1, BEST1, TTC8, C2orf71, ARL6, ZNF513, DHDDS, BEST1, PRPH2, LRAT, SPATA7, CRX, and RPGR. See, e.g., Farrar et al.

(2017) Hum Mol Genet. 26(R1):R2-R11, Tsang et al. (2018) Adv Exp Med Biol. 1085:69-77, Ali et al. (2017) 3 Biotech. 7(4):251, Lyraki et al. (2016) Biochem. Soc. Trans. 44(5): 1235-1244, and Daiger et al. (2013) Clinical Genetics. 84 (2):132-141; herein incorporated by reference.

By "therapeutically effective dose or amount" of α-ketoglutarate or a derivative thereof is intended an amount that, when administered alone or in combination with other neuroprotective agents, nutritional supplements, and/or a ketogenic diet, as described herein, brings about a positive therapeutic response, such as improved recovery from a disease or disorder associated with retinal degeneration (e.g., retinitis pigmentosa). For example, a therapeutically effective dose or amount may prolong photoreceptor cell survival (e.g., rod photoreceptor cells and cone photoreceptor cells), restore visual function, reduce neuronal cell loss, and/or delay disease progression. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

"Substantially purified" generally refers to isolation of a component such as a substance (compound, drug, vitamin, metabolite, nucleic acid, polynucleotide, protein, or polypeptide) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography, gel filtration, and sedimentation according to density.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

Biomarkers. The term "biomarker" as used herein refers to a compound, such as a protein, a mRNA, a metabolite, or a metabolic byproduct which is differentially expressed or present at different concentrations, levels or frequencies in one sample compared to another, such as a vitreous or retinal sample derived from patients who have a disease or disorder associated with retinal degeneration (e.g., retinitis pigmentosa) compared to one or more vitreous or retinal samples from healthy control subjects (i.e., subjects not having a disease or disorder associated with retinal degeneration). Biomarkers include, but are not limited to, down-regulated proteins in the retina involved in oxidative phosphorylation such as ATP synthase, mitochondrial F1 complex, alpha subunit 1, ATP synthase, mitochondrial F1 complex, beta polypeptide, ATP synthase, mitochondrial F1 complex, gamma polypeptide, ATP synthase, mitochondrial Fo complex subunit $B_1$, ATP synthase, mitochondrial Fo complex subunit D, ATP synthase, mitochondrial Fo complex subunit F2, ATP synthase, mitochondrial Fo complex subunit G, ATP synthase, mitochondrial F1 complex, O subunit, cytochrome c oxidase subunit 4I1, cytochrome c oxidase subunit 5A, cytochrome c oxidase subunit $6B_1$, cytochrome c1, cytochrome c, somatic, cytochrome c oxidase subunit II, NADH dehydrogenase, subunit 5 (complex 1), NADH:ubiquinone oxidoreductase subunit A1, NDUFA4, mitochondrial complex associated, NADH:ubiquinone oxidoreductase subunit A5, NADH:ubiquinone oxidoreductase subunit A9, NADH:ubiquinone oxidoreductase subunit A10, NADH:ubiquinone oxidoreductase subunit A11, NADH:ubiquinone oxidoreductase subunit A13, NADH:ubiquinone oxidoreductase subunit B5, NADH:ubiquinone oxidoreductase subunit B6, NADH:ubiquinone oxidoreductase subunit B10, NADH:ubiquinone oxidoreductase core subunit S1, NADH:ubiquinone oxidoreductase core subunit S2, NADH:ubiquinone oxidoreductase core subunit S3 NADH:ubiquinone oxidoreductase subunit S4, NADH:ubiquinone oxidoreductase core subunit S7, NADH:ubiquinone oxidoreductase core subunit S8, NADH:ubiquinone oxidoreductase core subunit V1, succinate dehydrogenase complex flavoprotein subunit A, succinate dehydrogenase complex iron sulfur subunit B, succinate dehydrogenase complex subunit C, ubiquinol-cytochrome c reductase, complex III subunit X, ubiquinol-cytochrome c reductase binding protein, ubiquinol-cytochrome c reductase core protein I, ubiquinol-cytochrome c reductase core protein II, and ubiquinol-cytochrome c reductase, and Rieske iron-sulfur polypeptide 1; down-regulated proteins in the retina involved in the tricarboxylic acid (TCA) cycle such as aconitase 2, citrate synthase, dihydrolipoamide dehydrogenase, dihydrolipoamide S-succinyltransferase, fumarate hydratase, isocitrate dehydrogenase 3 (NAD+) alpha, isocitrate dehydrogenase 3 (NAD+) beta, isocitrate dehydrogenase 3 (NAD+) gamma, malate dehydrogenase 2, oxoglutarate dehydrogenase, succinate dehydrogenase complex flavoprotein subunit A, succinate dehydrogenase complex iron sulfur subunit B, succinate dehydrogenase complex subunit C, and succinate-CoA ligase ADP-forming beta subunit; down-regulated proteins in the retina involved in the sirtuin signaling pathway such as ATP citrate lyase, ATP synthase, mitochondrial F1 complex, alpha subunit 1, ATP synthase, mitochondrial F1 complex, beta polypeptide, ATP synthase, mitochondrial F1 complex, gamma polypeptide 1, ATP synthase, mitochondrial Fo complex subunit B1, cytochrome c1, glucose-6-phosphate dehydrogenase, GABA type A receptor associated protein like 1, glutaminase, glutamate dehydrogenase 1, glutamic-oxaloacetic transaminase 2, H1 histone family member 0, histone cluster 1 H1 family member c, lactate dehydrogenase A, lactate dehydrogenase B, NADH dehydrogenase, subunit 5 (complex I), N-myc downstream regulated 1, NADH:ubiquinone oxidoreductase subunit A1, NDUFA4, mitochondrial complex associated, NADH:ubiquinone oxidoreductase subunit A5, NADH:ubiquinone oxidoreductase subunit A9, NADH:ubiquinone oxidoreductase subunit A10, NADH:ubiquinone oxidoreductase subunit A11, NADH:ubiquinone oxidoreductase subunit A13, NADH:ubiquinone oxidoreductase subunit B5, NADH:ubiquinone oxidoreductase subunit B6, NADH:ubiquinone oxidoreductase subunit B10, NADH:ubiquinone oxidoreductase core subunit S1, NADH:ubiquinone oxidoreductase core subunit S2, NADH:ubiquinone oxidoreductase core subunit S3, NADH:ubiquinone oxidoreductase core subunit S4, NADH:ubiquinone oxidoreductase core subunit S7, NADH:ubiquinone oxidoreductase core subunit S8, NADH:ubiquinone oxidoreductase core subunit V1, pyruvate dehydrogenase (lipoamide) alpha 1, phosphoglycerate mutase 1, phosphoglycerate kinase 1, peptidylprolyl isomerase D, succinate dehydrogenase complex flavoprotein subunit A, succinate dehydrogenase complex iron sulfur subunit B, succinate dehydrogenase complex subunit C, splicing factor 3a subunit 1, solute carrier family 25 member 4, solute carrier family 2 member 1, superoxide dismutase 1, superoxide dismutase 2, translocase of inner mitochondrial membrane 44, translocase of outer mitochondrial membrane 22, tripartite motif containing 28, tubulin alpha 4a, ubiquinol-cytochrome c reductase core protein II, ubiquinol-cytochrome c reductase, Rieske iron-sulfur polypeptide 1, voltage dependent anion channel 1, and voltage dependent anion channel 2. In some embodiments, vitreous or retinal biomarker protein levels are measured. A decrease in retinal protein expression of a biomarker may be associated with a corresponding increase in vitreous protein expression because a degenerating neural retina leaks proteins into the vitreous. Biomarkers involved in the rod photoreceptor transduction pathway that are upregulated in the vitreous at the onset of rod cell degeneration include, but are not limited to, rhodopsin (Rho), guanine nucleotide-binding protein alpha and beta subunits (Gnat1 and Gnb1), phosducin (Pdc), cyclic nucleotide-gated channel beta 1 (Cngb1), rhodopsin kinase (Grk1), recoverin (Rcvrn), and S-arrestin (Sag).

In some embodiments, the concentration or level of a biomarker is determined before and after the administration of a treatment for a disease or disorder associated with retinal degeneration to a subject. The treatment may comprise, for example, without limitation, administering a therapeutically effective amount of α-ketoglutarate, or a derivative thereof, alone or in combination with one or more neuroprotective agents or nutritional supplements to a subject or putting the subject on a ketogenic diet, or a combination thereof. In some embodiments, the treatment further comprises administering supplements, such as vitamin A, DHA, or lutein, gene therapy, retinal sheet transplantation, or implantation of optic prosthetic devices; or a combination thereof. The degree of change in the concentration or level of a biomarker, or lack thereof, is interpreted as an indication of whether the treatment has the desired effect (e.g., reversing, halting, or slowing retinal degeneration). In other words, the concentration or level of a biomarker is determined before and after the administration of the treatment to an individual, and the degree of change, or lack thereof, in the level is interpreted as an indication of whether the individual is "responsive" to the treatment.

A "reference level" or "reference value" of a biomarker means a level of the biomarker that is indicative of a particular disease state, phenotype, or predisposition to developing a particular disease state or phenotype, or lack thereof, as well as combinations of disease states, phenotypes, or predisposition to developing a particular disease state or phenotype, or lack thereof. A "positive" reference level of a biomarker means a level that is indicative of a particular disease state or phenotype. A "negative" reference level of a biomarker means a level that is indicative of a lack of a particular disease state or phenotype. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched or gender-matched so that comparisons may be made between biomarker levels in samples from subjects of a certain age or gender and reference levels for a particular disease state, phenotype, or lack thereof in a certain age or gender group). Such reference levels may also be tailored to specific techniques that are used to measure levels of biomarkers in biological samples (e.g., mass spectrometry (e.g., LC-MS, LC-MS/MS, GC-MS), NMR, PCR, microarray analysis, biochemical or enzymatic assays, etc.), where the levels of biomarkers may differ based on the specific technique that is used.

A "similarity value" is a number that represents the degree of similarity between two things being compared. For example, a similarity value may be a number that indicates the overall similarity between a patient's biomarker profile using specific phenotype-related biomarkers and reference value ranges for the biomarkers in one or more control samples or a reference profile (e.g., the similarity to a "retinitis pigmentosa" biomarker expression profile or a "retinal degeneration" biomarker expression profile). The similarity value may be expressed as a similarity metric, such as a correlation coefficient, or may simply be expressed as the expression level difference, or the aggregate of the expression level differences, between levels of biomarkers in a patient sample and a control sample or reference expression profile.

The terms "quantity", "amount", and "level" are used interchangeably herein and may refer to an absolute quantification of a molecule or an analyte in a sample, or to a relative quantification of a molecule or analyte in a sample, i.e., relative to another value such as relative to a reference value as taught herein, or to a range of values for the biomarker. These values or ranges can be obtained from a single patient or from a group of patients.

Obtaining and assaying a sample. The term "assaying" is used herein to include the physical steps of manipulating a biological sample (e.g., vitreous or retinal sample) to generate data related to the sample. As will be readily understood by one of ordinary skill in the art, a biological sample must be "obtained" prior to assaying the sample. Thus, the term "assaying" implies that the sample has been obtained. The terms "obtained" or "obtaining" as used herein encompass the act of receiving an extracted or isolated biological sample. For example, a testing facility can "obtain" a biological sample in the mail (or via delivery, etc.) prior to assaying the sample. In some such cases, the biological sample was "extracted" or "isolated" from an individual by another party prior to mailing (i.e., delivery, transfer, etc.), and then "obtained" by the testing facility upon arrival of the sample. Thus, a testing facility can obtain the sample and then assay the sample, thereby producing data related to the sample.

The terms "obtained" or "obtaining" as used herein can also include the physical extraction or isolation of a biological sample from a subject. Accordingly, a biological sample can be isolated from a subject (and thus "obtained") by the same person or same entity that subsequently assays the sample. When a biological sample is "extracted" or "isolated" from a first party or entity and then transferred (e.g., delivered, mailed, etc.) to a second party, the sample was "obtained" by the first party (and also "isolated" by the first party), and then subsequently "obtained" (but not "isolated") by the second party. Accordingly, in some embodiments, the step of obtaining does not comprise the step of isolating a biological sample.

In some embodiments, the step of obtaining comprises the step of isolating a biological sample (e.g., a pre-treatment biological sample, a post-treatment biological sample, etc.). Methods and protocols for isolating various biological samples (e.g., a blood sample, a serum sample, a plasma sample, a biopsy sample, an aspirate, etc.) will be known to one of ordinary skill in the art and any convenient method may be used to isolate a biological sample.

It will be understood by one of ordinary skill in the art that in some cases, it is convenient to wait until multiple samples (e.g., a pre-treatment biological sample and a post-treatment biological sample) have been obtained prior to assaying the samples. Accordingly, in some cases an isolated biological sample (e.g., a pre-treatment biological sample, a post-treatment biological sample, etc.) is stored until all appropriate samples have been obtained. One of ordinary skill in the art will understand how to appropriately store a variety of different types of biological samples and any convenient method of storage may be used (e.g., refrigeration) that is appropriate for the particular biological sample. In some embodiments, a pre-treatment biological sample is assayed prior to obtaining a post-treatment biological sample. In some cases, a pre-treatment biological sample and a post-treatment biological sample are assayed in parallel. In some cases, multiple different post-treatment biological samples and/or a pre-treatment biological sample are assayed in parallel. In some cases, biological samples are processed immediately or as soon as possible after they are obtained.

In some embodiments, the concentration (i.e., "level"), or expression level of a gene product, which may be an RNA, a protein, etc., (which will be referenced herein as a biomarker), in a biological sample is measured (i.e., "determined"). By "expression level" (or "level") it is meant the level of gene product (e.g. the absolute and/or normalized value determined for the RNA expression level of a biomarker or for the expression level of the encoded polypeptide, or the concentration of the protein in a biological sample). The term "gene product" or "expression product" are used herein to refer to the RNA transcription products (RNA transcripts, e.g. mRNA, an unspliced RNA, a splice variant mRNA, and/or a fragmented RNA) of the gene, including mRNA, and the polypeptide translation products of such RNA transcripts. A gene product can be, for example, an unspliced RNA, an mRNA, a splice variant mRNA, a microRNA, a fragmented RNA, a polypeptide, a post-translationally modified polypeptide, a splice variant polypeptide, etc.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assaying may be relative or absolute. For example, "assaying" can be determining whether the expression level is less than or "greater than or equal to" a particular threshold, (the threshold can be pre-determined or can be determined by assaying a control sample). On the other hand, "assaying to determine the expression level" can mean determining a quantitative value (using any convenient metric) that represents the level of expression (i.e., expression level, e.g., the amount of protein and/or RNA, e.g., mRNA) of a particular biomarker. The level of expression can be expressed in arbitrary units associated with a particular assay (e.g., fluorescence units, e.g., mean fluorescence intensity (MFI)), or can be expressed as an absolute value with defined units (e.g., number of mRNA transcripts, number of protein molecules, concentration of protein, etc.). Additionally, the level of expression of a biomarker can be compared to the expression level of one or more additional genes (e.g., nucleic acids and/or their encoded proteins) to derive a normalized value that represents a normalized expression level. The specific metric (or units) chosen is not crucial as long as the same units are used (or conversion to the same units is performed) when evaluating multiple biological samples from the same individual (e.g., biological samples taken at different points in time from the same individual). This is because the units cancel when calculating a fold-change (i.e., determining a ratio) in the expression level from one biological sample to the next (e.g., biological samples taken at different points in time from the same individual).

"Providing an analysis" is used herein to refer to the delivery of an oral or written analysis (i.e., a document, a report, etc.). A written analysis can be a printed or electronic document. A suitable analysis (e.g., an oral or written report) provides any or all of the following information: identifying information of the subject (name, age, etc.), a description of what type of biological sample(s) was used and/or how it was used, the technique used to assay the sample (e.g., vitreous sample), the results of the assay (e.g., the level of the biomarker as measured in the pre-treatment and post-treatment assay and/or the fold-change of a biomarker level in a post-treatment assay compared to a pre-treatment assay), the assessment as to whether the individual is determined to be responsive or not responsive to a treatment, the assessment as to whether the individual is determined to have retinitis pigmentosa, a recommendation to continue or alter therapy, a recommended strategy for additional therapy, etc. The report can be in any format including, but not limited to printed information on a suitable medium or substrate (e.g., paper); or electronic format. If in electronic format, the report can be in any computer readable medium, e.g., diskette, compact disk (CD), flash drive, and the like, on which the information has been recorded. In addition, the report may be present as a website address which may be used via the internet to access the information at a remote site.

Compositions

Pharmaceutical Compositions. Pharmaceutical compositions comprising α-ketoglutarate or a derivative thereof can be used to treat a disease or disorder associated with retinal degeneration. In some embodiments, the pharmaceutical composition comprises a cell permeable derivative of α-ketoglutarate such as a monoester derivative including, for example, without limitation, α-ketoglutarate benzyl ester, α-ketoglutarate octyl ester, and α-ketoglutarate trifluoromethyl benzyl (TFMB) ester. For a description of cell permeable derivatives of a-ketoglutarate, see, e.g., MacKenzie et al. (2007) Mol. Cell. Biol. 27(9):3282-9, herein incorporated by reference.

The α-ketoglutarate, or a derivative thereof, can be formulated into pharmaceutical compositions optionally comprising one or more pharmaceutically acceptable excipients. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition can also include an antimicrobial agent for preventing or deterring microbial growth. Nonlimiting examples of antimicrobial agents include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the α-ketoglutarate, or a derivative thereof, or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (BASF, Mount Olive, New Jersey); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the α-ketoglutarate or a derivative thereof (e.g., when contained in a drug delivery system) in the composition will vary depending on a number of factors, but will optimally be a therapeutically effective dose when the composition is in a unit dosage form or container (e.g., a vial). A therapeutically effective dose can be determined experimentally by repeated administration of increasing amounts of the composition in order to determine which amount produces a clinically desired endpoint.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, NJ (1998), and Kibbe, A. H., Handbook of Pharmaceutical Excipients, 3rd Edition, American Pharmaceutical Association, Washington, D.C., 2000.

The compositions encompass all types of formulations and in particular those that are suited for injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. Examples of suitable diluents for reconstituting solid compositions prior to injection include bacteriostatic water for injection, dextrose 5% in water, phosphate buffered saline, Ringer's solution, saline, sterile water, deionized water, and combinations thereof. With respect to liquid pharmaceutical compositions, solutions and suspensions are envisioned. Additional preferred compositions include those for oral, ocular, or localized delivery.

The pharmaceutical preparations herein can also be housed in a syringe, an implantation device, or the like, depending upon the intended mode of delivery and use. Preferably, the compositions comprising α-ketoglutarate or a derivative thereof are in unit dosage form, meaning an amount of a composition appropriate for a single dose, in a premeasured or pre-packaged form.

The compositions herein may optionally include one or more additional agents, such as neuroprotective agents and/ or nutritional supplements. Compounded preparations may include α-ketoglutarate, or a derivative thereof, and one or more other agents for treating a disease or disorder associated with retinal degeneration, such as, but not limited to, neuroprotective agents and/or nutritional supplements such as, vitamin A, retinyl palmitate, docosahexaenoic acid (DHA), lutein, and the like.

Alternatively, such agents can be contained in a separate composition from the composition comprising the α-ketoglutarate, or the derivative thereof, and co-administered concurrently, before, or after the composition comprising the α-ketoglutarate or the derivative thereof.

Methods

Administration of α-ketoglutarate. At least one therapeutically effective cycle of treatment with a composition comprising α-ketoglutarate, as described herein, will be administered to a subject for treatment of a disease or disorder associated with retinal degeneration. Diseases and disorders associated with retinal degeneration that can be treated by the methods described herein include, but are not limited to, retinitis pigmentosa, Usher syndrome, Alport's syndrome, Kearns-Sayre syndrome, abetalipoproteinemia, McLeod syndrome, Bardet-Biedl syndrome, neurosyphilis, toxoplasmosis and Refsum's disease.

By "therapeutically effective dose or amount" of α-ketoglutarate is intended an amount that, when administered alone or in combination with a neuroprotective agent, nutritional supplement, and/or a ketogenic diet, as described herein, brings about a positive therapeutic response, such as improved recovery from a disease or disorder associated with retinal degeneration (e.g., retinitis pigmentosa). For example, a therapeutically effective dose or amount may prolong photoreceptor cell survival (e.g., rod photoreceptor cells and/or cone photoreceptor cells), restore visual function, reduce neuronal cell loss, and/or delay disease progression. The exact amount required will vary from subject to subject, depending on the species, age, and general condition of the subject, the severity of the condition being treated, the particular type of α-ketoglutarate derivative, other neuroprotective agents, nutritional supplements, or drugs employed in combination, the mode of administration, and the like. An appropriate "effective" amount in any individual case may be determined by one of ordinary skill in the art using routine experimentation, based upon the information provided herein.

In certain embodiments, multiple therapeutically effective doses of compositions comprising α-ketoglutarate, and/or one or more other therapeutic agents, such as one or more other agents for treating a disease or disorder associated with retinal degeneration, such as, but not limited to, neuroprotective agents and/or nutritional supplements such as, vitamin A, retinyl palmitate, docosahexaenoic acid (DHA), lutein, or other medications will be administered. The compositions comprising α-ketoglutarate are typically, although not necessarily, administered orally, via injection (subcutaneously, intravenously, or intramuscularly), by infusion, topically, or locally. Additional modes of administration are also contemplated, such as intraocular, intra-arterial, intravascular, pulmonary, intralesional, and so forth.

The preparations according to the invention are also suitable for local treatment. For example, compositions comprising α-ketoglutarate may be administered by intraocular injection. The particular preparation and appropriate method of administration can be chosen to target the α-ketoglutarate to photoreceptor cells at risk of degeneration. Local treatment may avoid some side effects of systemic therapy.

The pharmaceutical preparation can be in the form of a liquid solution or suspension immediately prior to administration, but may also take another form such as a syrup, cream, ointment, tablet, capsule, powder, gel, matrix, suppository, or the like. The pharmaceutical compositions comprising α-ketoglutarate, or a derivative thereof, and/or other agents may be administered using the same or different routes of administration in accordance with any medically acceptable method known in the art.

In another embodiment, the pharmaceutical compositions comprising α-ketoglutarate and/or other agents are administered prophylactically, e.g., to prevent retinal degeneration. Such prophylactic uses will be of particular value for subjects who have a genetic predisposition to developing retinal degeneration such as individuals having one or more mutations associated with retinitis pigmentosa. At least 260 genes, including numerous candidate mutations (over 3000) in recessive, dominant, and X-linked alleles have been linked to retinitis pigmentosa. See, e.g., Farrar et al. (2017) Hum Mol Genet. 26(R1):R2-R11, Tsang et al. (2018) Adv Exp Med Biol. 1085:69-77, Ali et al. (2017) 3 Biotech. 7(4):251, Lyraki et al. (2016) Biochem. Soc. Trans. 44(5): 1235-1244, and Wang; herein incorporated by reference. Patients having such mutations may benefit from treatment according to the methods described herein. In some embodiments, the patient has one or more mutations in a gene selected from the group consisting of RPY, RP1, RP2, RPGR, PRPH2, RP9, IMPDH1, PRPF31, CRB1, PRPF8, TULP1, CA4, HPRPF3, ABCA4, EYS, CERKL, FSCN2, TOPORS, SNRNP200, SEMA4A, PROD, NR2E3, MERTK, USH2A, PROM1, KLHL7, CNGB1, BEST1, TTC8, C2orf71, ARL6, ZNF513, DHDDS, BEST1, PRPH2, LRAT, SPATA7, CRX, and RPGR, wherein the mutation has been linked to retinitis pigmentosa.

In another embodiment, the pharmaceutical compositions comprising α-ketoglutarate, or a derivative thereof, neuroprotective agents, and/or nutritional supplements, and/or other agents are in a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition.

Those of ordinary skill in the art will appreciate which conditions the α-ketoglutarate or a derivative thereof can effectively treat. The actual dose to be administered will vary depending upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case.

In certain embodiments, multiple therapeutically effective doses of a composition comprising α-ketoglutarate or a derivative thereof will be administered according to a daily dosing regimen or intermittently. For example, a therapeutically effective dose can be administered, one day a week, two days a week, three days a week, four days a week, or five days a week, and so forth. By "intermittent" administration is intended the therapeutically effective dose can be administered, for example, every other day, every two days, every three days, once a week, every other week, and so forth. For example, in some embodiments, a composition comprising a-ketoglutarate will be administered once-weekly, twice-weekly or thrice-weekly for an extended period of time, such as for 1, 2, 3, 4, 5, 6, 7, 8 . . . 10 . . . 15 . . . 24 weeks, and so forth. By "twice-weekly" or "two times per week" is intended that two therapeutically effective doses of the agent in question is administered to the subject within a 7 day period, beginning on day 1 of the first week of administration, with a minimum of 72 hours, between doses and a maximum of 96 hours between doses. By "thrice weekly" or "three times per week" is intended that three therapeutically effective doses are administered to the subject within a 7 day period, allowing for a minimum of 48 hours between doses and a maximum of 72 hours between doses. For purposes of the present invention, this type of dosing is referred to as "intermittent" therapy. In accordance with the methods of the present invention, a subject can receive intermittent therapy (i.e., once-weekly, twice-weekly or thrice-weekly administration of a therapeutically effective dose) for one or more weekly cycles until the desired therapeutic response is achieved. The agents can be administered by any acceptable route of administration as noted herein below. The amount administered will depend on the potency of the α-ketoglutarate or the derivative thereof and/or other agents administered, the magnitude of the effect desired, and the route of administration.

α-ketoglutarate or a derivative thereof (again, preferably provided as part of a pharmaceutical preparation) can be administered alone or in combination with one or more other therapeutic agents, such as other agents for treating a disease or disorder associated with retinal degeneration, including, but not limited to, neuroprotective agents and/or nutritional supplements such as, vitamin A, vitamin B2 (riboflavin), vitamin B3 (nicotinamide), retinyl palmitate, docosahexaenoic acid (DHA), lutein, or other medications used to treat a particular condition or disease according to a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Preferred compositions are those requiring dosing no more than once a day.

The α-ketoglutarate or a derivative thereof can be administered prior to, concurrent with, or subsequent to other agents. If provided at the same time as other agents, α-ketoglutarate or a derivative thereof can be provided in the same or in a different composition. Thus, a-ketoglutarate or a derivative thereof and one or more other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising α-ketoglutarate or a derivative thereof and a dose of a pharmaceutical composition comprising at least one other agent, such as another drug for treating an infection, which in combination comprise a therapeutically effective dose, according to a particular dosing regimen. Similarly, α-ketoglutarate or a derivative thereof and one or more other therapeutic agents can be administered in at least one therapeutic dose. Administration of the separate pharmaceutical compositions can be performed simultaneously or at different times (i.e., sequentially, in either order, on the same day, or on different days), as long as the therapeutic effect of the combination of these substances is caused in the subject undergoing therapy.

Toxicity can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in further optimizing and/or defining a therapeutic dosage range and/or a sub-therapeutic dosage range (e.g., for use in humans). The exact formulation, route of administration and dosage can be chosen by the individual physician in view of the patient's condition.

Additionally, treatment with α-ketoglutarate or a derivative thereof may be combined with any other medical treatment for a disease or disorder associated with retinal degeneration, such as, but not limited to, administering supplements, such as vitamin A, vitamin B2 (riboflavin), vitamin $B_3$ (nicotinamide), DHA, and lutein, gene therapy, retinal sheet transplantation, and implantation of optic prosthetic devices.

Nutritional Treatment of Retinal Degeneration

A disease or disorder associated with retinal degeneration may be treated nutritionally (i.e., nutritional therapy) by putting the subject on a ketogenic diet to improve photoreceptor cell survival. The ketogenic diet is a low-carbohydrate, high-fat diet. Subjects on the ketogenic diet are required to reduce daily intake of carbohydrates in any form (e.g., monosaccharides, disaccharides, oligosaccharides, and polysaccharides), including carbohydrates found in sugar, honey, fruit, vegetables, breads, cereal, flour, desserts, etc. In some embodiments, carbohydrate intake is restricted to 10-15 g of carbohydrate per day. In certain embodiments, the ketogenic diet reduces the subject's daily intake of carbohydrates by at least 50% to 95%, including any percent within this range, such as 50, 55, 60, 65, 70, 75, 80, 85, 90, 91, 92, 93, 94, or 95%. Adequate protein should be provided in the diet with the remainder of the calories in the diet derived from fat. Additionally, vitamins, particularly A, B, and D vitamins as well as calcium may be supplemented to meet nutritional needs. For a description of the ketogenic diet, see, e.g., Walczyk et al. (2017) Consult Pharm. 32(7): 388-396, Sampaio et al. (2016) Arq Neuropsiquiatr. 74(10): 842-848, Freeman et al. (2007) Pediatrics 119(3):535-543, Zupec-Kania et al. (2009) Nutr Clin Pract. 23(6):589-596; herein incorporated by reference.

Restricting carbohydrate intake forces the body to burn fat to provide energy rather than carbohydrates. The ketogenic diet increases cellular levels of acetyl-CoA, which is utilized by the tricarboxylic acid (TCA) cycle together with oxaloacetate. In addition, the ketogenic diet reduces transamination of glutamate to aspartate, thereby providing more glutamate for use by cells.

Nutritional therapy may be implemented by providing the subject being treated for retinal degeneration with dietary instructions for reducing carbohydrate intake and increasing fat intake to meet the dietary requirements of the ketogenic diet. Alternatively, the subject may be provided with prepackaged therapeutic meals (e.g., breakfast meals, lunch meals, dinner meals, or snacks) that meet the requirements of the ketogenic diet. Such prepackaged therapeutic meals may aid patients in complying with dietary restrictions. Preferably, any prescribed diet provides other nutrients at levels in accordance with United States Recommended Daily Allowances (USRDA) guidelines.

In some embodiments, nutritional therapy may further include intake of an α-ketoglutarate supplement. The α-ketoglutarate supplement may be administered, for example, orally either added to food or a drink, or ingested as tablets.

Nutritional therapy should bring about a positive therapeutic response with respect to treatment of an individual for retinal degeneration. By "positive therapeutic response" is intended that the individual undergoing the nutritional therapy as described herein exhibits an improvement in one or more symptoms of a disease or disorder associated with retinal degeneration. For example, a positive therapeutic response may include prolonging photoreceptor cell survival (e.g., rod photoreceptor cells and/or cone photoreceptor cells), restoring visual function, reducing neuronal cell loss, or delaying disease progression.

A subject may continue the nutritional therapy (e.g., ketogenic diet and/or α-ketoglutarate supplementation) for as long as the nutritional therapy is beneficial for treating the disease or disorder associated with retinal degeneration in the subject. For example, a subject may continue the nutritional therapy for at least 1 month to 3 months, at least 1 month to 4 months, at least 5 months to 1 year, 2 years, 3 years, 4 years, 5 years, or longer. Continued nutritional therapy may be beneficial for delaying disease progression and preventing further vision loss.

The subject may be treated either therapeutically for existing retinal degeneration or prophylactically (e.g., a subject at risk of developing retinal degeneration because of a genetic predisposition or presence of one or more developmental, environmental, occupational, or behavioral risk factors). In particular, a subject may be treated prophylactically if the subject has a genetic mutation known to be associated with a risk of developing retinal degeneration. For example, a subject at risk of developing retinal degeneration (e.g., having one or more risk factors) may be treated prophylactically for retinal degeneration by putting the subject on a ketogenic diet and/or administering an α-ketoglutarate supplement. Prophylactic treatment may be repeated, for example, annually, every two years, every three years, every four years, or every five years to reduce the risk of retinal degeneration.

Additionally, nutritional therapy may be combined with any other medical treatment for a disease or disorder associated with retinal degeneration, such as, but not limited to, administering supplements, such as vitamin A, vitamin B2 (riboflavin), vitamin B3 (nicotinamide), DHA, and lutein, gene therapy, retinal sheet transplantation, and implantation of optic prosthetic devices.

In another embodiment, the method further comprises monitoring retinal degeneration in the subject during nutritional therapy. Retinal degeneration may be monitored for a period during the time the subject is kept on a ketogenic diet and/or receives α-ketoglutarate and/or B vitamins, and/or other nutritional supplements. In certain embodiments, the monitoring is used to adjust the ketogenic diet of the subject to reduce the carbohydrate levels or increase fat intake sufficiently to suppress retinal degeneration.

Biomarkers and Diagnostic Methods

Biomarkers that can be used in the practice of the subject methods include, without limitation, proteins involved in oxidative phosphorylation such as ATP synthase, mitochondrial F1 complex, alpha subunit 1, ATP synthase, mitochondrial F1 complex, beta polypeptide, ATP synthase, mitochondrial F1 complex, gamma polypeptide, ATP synthase, mitochondrial Fo complex subunit B1, ATP synthase, mitochondrial Fo complex subunit D, ATP synthase, mitochondrial Fo complex subunit F2, ATP synthase, mitochondrial Fo complex subunit G, ATP synthase, mitochondrial F1 complex, O subunit, cytochrome c oxidase subunit 4I1, cytochrome c oxidase subunit 5A, cytochrome c oxidase subunit 6B1, cytochrome c1, cytochrome c, somatic, cytochrome c oxidase subunit II, NADH dehydrogenase, subunit 5 (complex 1), NADH:ubiquinone oxidoreductase subunit A1, NDUFA4, mitochondrial complex associated, NADH:ubiquinone oxidoreductase subunit A5, NADH:u-biquinone oxidoreductase subunit A9, NADH:ubiquinone oxidoreductase subunit A10, NADH:ubiquinone oxidoreductase subunit A11, NADH:ubiquinone oxidoreductase subunit A13, NADH:ubiquinone oxidoreductase subunit B5, NADH:ubiquinone oxidoreductase subunit B6, NADH:ubiquinone oxidoreductase subunit B10, NADH:ubiquinone oxidoreductase core subunit S1, NADH:ubiquinone oxidoreductase core subunit S2, NADH:ubiquinone oxidoreductase core subunit S3 NADH:ubiquinone oxidoreductase subunit S4, NADH:ubiquinone oxidoreductase core subunit S7, NADH:ubiquinone oxidoreductase core subunit S8, NADH:ubiquinone oxidoreductase core subunit V1, succinate dehydrogenase complex flavoprotein subunit A, succinate dehydrogenase complex iron sulfur subunit B, succinate dehydrogenase complex subunit C, ubiquinol-cytochrome c reductase, complex III subunit X, ubiquinol-cytochrome c reductase binding protein, ubiquinol-cytochrome c reductase core protein 1, ubiquinol-cytochrome c reductase core protein 11, and ubiquinol-cytochrome c reductase, and Rieske iron-sulfur polypeptide 1; proteins involved in the tricarboxylic acid (TCA) cycle such as aconitase 2, citrate synthase, dihydrolipoamide dehydrogenase, dihydrolipoamide S-succinyltransferase, fumarate hydratase, isocitrate dehydrogenase 3 (NAD+) alpha, isocitrate dehydrogenase 3 (NAD+) beta, isocitrate dehydrogenase 3 (NAD+) gamma, malate dehydrogenase 2, oxoglutarate dehydrogenase, succinate dehydrogenase complex flavoprotein subunit A, succinate dehydrogenase complex iron sulfur subunit B, succinate dehydrogenase complex subunit C, and succinate-CoA ligase ADP-forming beta subunit; proteins involved in the sirtuin signaling pathway such as ATP citrate lyase, ATP synthase, mitochondrial F1 complex, alpha subunit 1, ATP synthase, mitochondrial F1 complex, beta polypeptide, ATP synthase, mitochondrial F1 complex, gamma polypeptide 1, ATP synthase, mitochondrial Fo complex subunit B1, cytochrome c1, glucose-6-phosphate dehydrogenase, GABA type A receptor associated protein like 1, glutaminase, glutamate dehydrogenase 1, glutamic-oxaloacetic transaminase 2, H1 histone family member 0, histone cluster 1 H1 family member c, lactate dehydrogenase A, lactate dehydrogenase B, NADH dehydrogenase, subunit 5 (complex I), N-myc downstream regulated 1, NADH:ubiquinone oxidoreductase subunit A1, NDUFA4, mitochondrial complex associated, NADH:ubiquinone oxidoreductase subunit A5, NADH:ubiquinone oxidoreductase subunit A9, NADH:ubiquinone oxidoreductase subunit A10, NADH:ubiquinone oxidoreductase subunit A11, NADH:ubiquinone oxidoreductase subunit A13, NADH:ubiquinone oxidoreductase subunit B5, NADH:ubiquinone oxidoreductase subunit B6, NADH:ubiquinone oxidoreductase subunit B10, NADH:ubiquinone oxidoreductase core subunit S1, NADH:ubiquinone oxidoreductase core subunit S2, NADH:ubiquinone oxidoreductase core subunit S3, NADH:ubiquinone oxidoreductase subunit S4, NADH:ubiquinone oxidoreductase core subunit S7, NADH:ubiquinone oxidoreductase core subunit S8, NADH:ubiquinone oxidoreductase core subunit V1, pyruvate dehydrogenase (lipoamide) alpha 1, phosphoglycerate mutase 1, phosphoglycerate kinase 1, peptidylprolyl isomerase D, succinate dehydrogenase complex flavoprotein subunit A, succinate dehydrogenase complex iron sulfur subunit B, succinate dehydrogenase complex subunit C, splicing factor 3a subunit 1, solute carrier family 25 member 4, solute carrier family 2 member 1, superoxide dismutase 1, superoxide dismutase 2, translocase of inner mitochondrial membrane 44, translocase of outer mitochondrial membrane 22, tripartite motif containing 28, tubulin alpha 4a, ubiquinol-cytochrome c reductase core protein II, ubiquinol-cytochrome c reductase, Rieske iron-sulfur polypeptide 1, voltage dependent anion channel 1, and voltage dependent anion channel 2. In some embodiments, vitreous or retinal biomarker protein levels are measured. A decrease in retinal protein expression of a biomarker may be associated with a corresponding increase in vitreous protein expression because a degenerating neural retina leaks proteins into the vitreous. Biomarkers involved in the rod photoreceptor transduction pathway that are upregulated in the vitreous at the onset of rod cell degeneration include, but are not limited to, rhodopsin (Rho), guanine nucleotide-binding protein alpha and beta subunits (Gnat1 and Gnb1), phosducin (Pdc), cyclic nucleotide-gated channel beta 1 (Cngb1), rhodopsin kinase (Grk1), recoverin (Rcvrn), and S-arrestin (Sag).

Aberrant changes in the levels of these biomarkers are associated with retinal degeneration. Accordingly, monitoring the levels of these biomarkers is useful for diagnosing diseases and disorders associated with retinal degeneration. The diagnostic methods described herein can be used for evaluating subjects who have not yet developed clinical symptoms or subjects who have developed clinical symptoms who are suspected of having a disease or disorder associated with retinal degeneration. The methods described herein are also useful for monitoring subjects who have a genetic predisposition or family history indicating a risk of developing a disease or disorder associated with retinal degeneration. In particular, the subject methods are useful for monitoring a subject who has retinitis pigmentosa or a genotype comprising at least one mutation indicating a risk of developing retinitis pigmentosa. In some embodiments, the subject has a recessive, dominant, or X-linked allele associated with retinitis pigmentosa. Retinitis pigmentosa may be associated with one or more mutations in genes including, without limitation, RPY, RP1, RP2, RPGR, PRPH2, RP9, IMPDH1, PRPF31, CRB1, PRPF8, TULP1, CA4, HPRPF3, ABCA4, EYS, CERKL, FSCN2, TOPORS, SNRNP200, SEMA4A, PROD, NR2E3, MERTK, USH2A, PROM1, KLHL7, CNGB1, BEST1, TTC8, C2orf71, ARL6, ZNF513, DHDDS, BEST1, PRPH2, LRAT, SPATA7, CRX, and RPGR. See, e.g., Farrar et al. (2017) Hum Mol Genet.

26(R1):R2-R11, Tsang et al. (2018) Adv Exp Med Biol. 1085:69-77, Ali et al. (2017) 3 Biotech. 7(4):251, Lyraki et al. (2016) Biochem. Soc. Trans. 44(5):1235-1244, and Daiger et al. (2013) Clinical Genetics. 84 (2):132-141; herein incorporated by reference.

The diagnostic methods for diagnosing a subject with a disease or disorder associated with retinal degeneration typically comprise the steps of a) obtaining a vitreous or retinal sample from the subject; and measuring one or more of the biomarkers described herein in the vitreous or retinal sample. The levels of the biomarkers in the sample can be compared with respective reference value ranges for the biomarkers in a control sample (i.e., from a normal or healthy subject, e.g., an individual known to not have retinitis pigmentosa or other disease or disorder associated with retinal degeneration).

For diagnosing retinitis pigmentosa, for example, when analyzing the levels of biomarkers in a vitreous sample from the subject, the reference value ranges used for comparison can represent the levels of one or more biomarkers in a vitreous sample from one or more subjects without retinitis pigmentosa (i.e., normal or healthy control), wherein detection of increased levels of one or more biomarkers selected from the group consisting of rhodopsin, guanine nucleotide-binding protein alpha subunit and beta subunit, phosducin, cyclic nucleotide-gated channel beta 1, rhodopsin kinase, recoverin, and S-arrestin in the vitreous sample from the subject compared to reference values ranges for the levels of the biomarkers in a control sample indicate the subject has retinitis pigmentosa. Alternatively, the reference values can represent the levels of one or more biomarkers in a vitreous sample from one or more subjects with retinitis pigmentosa, wherein similarity to the reference value ranges indicates the stage of disease progression of retinitis pigmentosa (e.g., extent of retinal degeneration).

A vitreous or retinal sample comprising biomarkers is obtained from the subject. A vitreous or retinal biopsy can be obtained by surgical techniques according to conventional methods well known in the art. For example, a fine-needle aspiration biopsy, which is typically performed with a needle having a 26-30 gauge, can be used to collect a vitreous or retinal biopsy. See, e.g., Examples and Eide et al. (2009) Acta Ophthalmol. 87(6):588-601, Skeie et al. (2012) Retina 32(10):2141-9, Monteiro et al. (2015) Proteomics Clin Appl. 9(1-2):187-202.

The methods described herein may be used to determine if a patient should be treated for a disease or disorder associated with retinal degeneration. For example, a patient is selected for treatment if the subject is diagnosed with a disease or disorder associated with retinal degeneration based on a biomarker expression profile. The treatment may comprise administering a therapeutically effective amount of α-ketoglutarate or a derivative thereof, a nutritional supplement such as, but not limited to, vitamin A, vitamin B2, vitamin B3, retinyl palmitate, docosahexaenoic acid (DHA), and lutein, or placing the subject on a ketogenic diet, or a combination thereof.

In some embodiments, the methods described herein are used for monitoring progression of a disease or disorder associated with retinal degeneration in a subject. For example, a first vitreous or retinal sample comprising biomarkers can be obtained from the subject at a first time point and a second vitreous or retinal sample comprising biomarkers can be obtained from the subject later at a second time point, followed by measuring one or more biomarkers in the samples. In some cases, combinations of biomarkers are used. In some such cases, the levels of all measured bio-markers must change (as described above) in order for the determination to be made regarding the diagnosis of the subject.

For example, retinal degeneration is associated with down-regulation of proteins in the retina involved in oxidative phosphorylation such as ATP synthase, mitochondrial F1 complex, alpha subunit 1, ATP synthase, mitochondrial F1 complex, beta polypeptide, ATP synthase, mitochondrial F1 complex, gamma polypeptide, ATP synthase, mitochondrial Fo complex subunit B1, ATP synthase, mitochondrial Fo complex subunit D, ATP synthase, mitochondrial Fo complex subunit F2, ATP synthase, mitochondrial Fo complex subunit G, ATP synthase, mitochondrial F1 complex, O subunit, cytochrome c oxidase subunit 4I1, cytochrome c oxidase subunit 5A, cytochrome c oxidase subunit 6B1, cytochrome c1, cytochrome c, somatic, cytochrome c oxidase subunit 11, NADH dehydrogenase, subunit 5 (complex 1), NADH:ubiquinone oxidoreductase subunit A1, NDUFA4, mitochondrial complex associated, NADH:ubiquinone oxidoreductase subunit A5, NADH:ubiquinone oxidoreductase subunit A9, NADH:ubiquinone oxidoreductase subunit A10, NADH:ubiquinone oxidoreductase subunit A11, NADH:ubiquinone oxidoreductase subunit A13, NADH:ubiquinone oxidoreductase subunit B5, NADH:ubiquinone oxidoreductase subunit B6, NADH:ubiquinone oxidoreductase subunit B10, NADH:ubiquinone oxidoreductase core subunit S1, NADH:ubiquinone oxidoreductase core subunit S2, NADH:ubiquinone oxidoreductase core subunit S3 NADH:ubiquinone oxidoreductase subunit S4, NADH:ubiquinone oxidoreductase core subunit S7, NADH:ubiquinone oxidoreductase core subunit S8, NADH:ubiquinone oxidoreductase core subunit V1, succinate dehydrogenase complex flavoprotein subunit A, succinate dehydrogenase complex iron sulfur subunit B, succinate dehydrogenase complex subunit C, ubiquinol-cytochrome c reductase, complex III subunit X, ubiquinol-cytochrome c reductase binding protein, ubiquinol-cytochrome c reductase core protein I, ubiquinol-cytochrome c reductase core protein II, and ubiquinol-cytochrome c reductase, and Rieske iron-sulfur polypeptide 1; down-regulation of proteins in the retina involved in the tricarboxylic acid (TCA) cycle such as aconitase 2, citrate synthase, dihydrolipoamide dehydrogenase, dihydrolipoamide S-succinyltransferase, fumarate hydratase, isocitrate dehydrogenase 3 (NAD+) alpha, isocitrate dehydrogenase 3 (NAD+) beta, isocitrate dehydrogenase 3 (NAD+) gamma, malate dehydrogenase 2, oxoglutarate dehydrogenase, succinate dehydrogenase complex flavoprotein subunit A, succinate dehydrogenase complex iron sulfur subunit B, succinate dehydrogenase complex subunit C, and succinate-CoA ligase ADP-forming beta subunit; and down-regulation of proteins in the retina involved in the sirtuin signaling pathway such as ATP citrate lyase, ATP synthase, mitochondrial F1 complex, alpha subunit 1, ATP synthase, mitochondrial F1 complex, beta polypeptide, ATP synthase, mitochondrial F1 complex, gamma polypeptide 1, ATP synthase, mitochondrial Fo complex subunit B1, cytochrome c1, glucose-6-phosphate dehydrogenase, GABA type A receptor associated protein like 1, glutaminase, glutamate dehydrogenase 1, glutamic-oxaloacetic transaminase 2, H1 histone family member 0, histone cluster 1 H1 family member c, lactate dehydrogenase A, lactate dehydrogenase B, NADH dehydrogenase, subunit 5 (complex I), N-myc downstream regulated 1, NADH:ubiquinone oxidoreductase subunit A1, NDUFA4, mitochondrial complex associated, NADH:ubiquinone oxidoreductase subunit A5, NADH:ubiquinone oxidoreductase subunit A9, NADH:ubiquinone oxidoreductase subunit A10, NADH:ubiquinone oxidoreductase subunit A11, NADH:ubiquinone oxidoreductase subunit A13, NADH:ubiquinone oxidoreductase subunit B5, NADH:ubiquinone oxidoreductase subunit B6, NADH:ubiquinone oxidoreductase subunit B10, NADH:ubiquinone oxidoreductase core subunit S1, NADH:ubiquinone oxidoreductase core subunit S2, NADH:ubiquinone oxidoreductase core subunit S3, NADH:ubiquinone oxidoreductase subunit S4, NADH:ubiquinone oxidoreductase core subunit S7, NADH:ubiquinone oxidoreductase core subunit S8, NADH:ubiquinone oxidoreductase core subunit V1, pyruvate dehydrogenase (lipoamide) alpha 1, phosphoglycerate mutase 1, phosphoglycerate kinase 1, peptidylprolyl isomerase D, succinate dehydrogenase complex flavoprotein subunit A, succinate dehydrogenase complex iron sulfur subunit B, succinate dehydrogenase complex subunit C, splicing factor 3a subunit 1, solute carrier family 25 member 4, solute carrier family 2 member 1, superoxide dismutase 1, superoxide dismutase 2, translocase of inner mitochondrial membrane 44, translocase of outer mitochondrial membrane 22, tripartite motif containing 28, tubulin alpha 4a, ubiquinol-cytochrome c reductase core protein II, ubiquinol-cytochrome c reductase, Rieske iron-sulfur polypeptide 1, voltage dependent anion channel 1, and voltage dependent anion channel 2. Therefore, decreasing levels of these biomarkers is associated with worsening retinal degeneration.

Decreases in protein levels of biomarkers in retinal samples may be associated with corresponding increases in levels of the biomarkers in vitreous samples because the degenerating neural retina leaks proteins into the vitreous. In some embodiments, rhodopsin, guanine nucleotide-binding protein alpha subunit and beta subunit, phosducin, cyclic nucleotide-gated channel beta 1, rhodopsin kinase, recoverin, and S-arrestin are measured in a vitreous sample, wherein increasing levels of rhodopsin, guanine nucleotide-binding protein alpha subunit and beta subunit, phosducin, cyclic nucleotide-gated channel beta 1, rhodopsin kinase, recoverin, and S-arrestin in the vitreous sample indicate that the subject is worsening.

The subject methods may also be used for assaying pre-treatment and post-treatment biological samples isolated from an individual to determine whether the individual is responsive or not responsive to a treatment for a disease or disorder associated with retinal degeneration. For example, a first retinal or vitreous sample comprising biomarkers can be obtained from the subject before the subject undergoes the therapy, and a second retinal or vitreous sample comprising biomarkers can be obtained from the subject after the subject undergoes the therapy, followed by measuring one or more biomarkers in the samples obtained from the subject.

In some cases, combinations of biomarkers are used in the subject methods. In some such cases, the levels of all measured biomarkers must change (as described above) in order for the determination to be made that the individual is responsive, maintaining responsiveness, or not responsive to a treatment. In some embodiments, rhodopsin, guanine nucleotide-binding protein alpha subunit and beta subunit, phosducin, cyclic nucleotide-gated channel beta 1, rhodopsin kinase, recoverin, and S-arrestin are used for monitoring efficacy of a therapy for treatment of retinitis pigmentosa in the subject, wherein detection of increased levels of one or more biomarkers selected from the group consisting of rhodopsin, guanine nucleotide-binding protein alpha subunit and beta subunit, phosducin, cyclic nucleotide-gated channel beta 1, rhodopsin kinase, recoverin, and S-arrestin in the second vitreous sample compared to the levels of the biomarkers in the first vitreous sample indicates that the subject is worsening or not responding to the therapy, and detection of decreased levels of one or more biomarkers selected from the group consisting of rhodopsin, guanine nucleotide-binding protein alpha subunit and beta subunit, phosducin, cyclic nucleotide-gated channel beta 1, rhodopsin kinase, recoverin, and S-arrestin in the second vitreous sample compared to the levels of the biomarkers in the first vitreous sample indicates that the subject is improving.

In some embodiments, only some biomarkers selected from rhodopsin, guanine nucleotide-binding protein alpha subunit and beta subunit, phosducin, cyclic nucleotide-gated channel beta 1, rhodopsin kinase, recoverin, and S-arrestin are used in the methods described herein. For example, a single biomarker, two types of biomarkers, three types of biomarkers, four types of biomarkers, or five types of biomarkers can be used in any combination. In other embodiments, all the biomarkers are used.

The level of a biomarker in in a pre-treatment vitreous or retinal sample can be referred to as a "pre-treatment value" because the first sample is isolated from the individual prior to the administration of the therapy (i.e., "pre-treatment"). The level of a biomarker in the pre-treatment sample can also be referred to as a "baseline value" because this value is the value to which "post-treatment" values are compared. In some cases, the baseline value (i.e., "pre-treatment value") is determined by determining the level of a biomarker in multiple (i.e., more than one, e.g., two or more, three or more, for or more, five or more, etc.) pre-treatment biological samples. In some cases, the multiple pre-treatment biological samples are isolated from an individual at different time points in order to assess natural fluctuations in biomarker levels prior to treatment. As such, in some cases, one or more (e.g., two or more, three or more, for or more, five or more, etc.) pre-treatment samples are isolated from the individual. In some embodiments, all of the pre-treatment samples will be the same type of biological sample (e.g., a vitreous or a retinal biopsy sample). In some cases, two or more pre-treatment samples are pooled prior to determining the level of the biomarker in the samples. In some cases, the level of the biomarker is determined separately for two or more pre-treatment biological samples and a "pre-treatment value" is calculated by averaging the separate measurements.

A post-treatment vitreous or retinal sample is isolated from an individual after the administration of a therapy. Thus, the level of a biomarker in a post-treatment sample can be referred to as a "post-treatment value". In some embodiments, the level of a biomarker is measured in additional post-treatment samples (e.g., a second, third, fourth, fifth, etc. post-treatment sample). Because additional post-treatment samples are isolated from the individual after the administration of a treatment, the levels of a biomarker in the additional samples can also be referred to as "post-treatment values."

The term "responsive" as used herein means that the treatment is having the desired effect; that is, the treatment is improving photoreceptor cell survival (e.g., rod photoreceptor cells and cone photoreceptor cells), restoring or maintaining visual function, reducing neuronal cell loss, and/or delaying disease progression. When the individual does not improve in response to the treatment, it may be desirable to seek a different therapy or treatment regime for the individual.

The diagnosis and/or monitoring of an individual for a disease or disorder associated with retinal degeneration (e.g., retinitis pigmentosa) is a direct and active clinical application of the correlation between levels of a biomarker and retinal degeneration. For example, "determining" requires the active step of reviewing the data, which is produced during the active assaying step(s), and resolving whether an individual does or does not have a disease or disorder associated with retinal degeneration and/or is responding or not responding to a treatment to prevent or decrease retinal degeneration and/or delay disease progression. Additionally, in some cases, a decision is made to proceed with the current treatment (i.e., therapy), or instead to alter the treatment. In some cases, the subject methods include the step of continuing therapy or altering therapy.

The term "continue treatment" (i.e., continue therapy) is used herein to mean that the current course of treatment (e.g., continued administration of a therapy) is to continue. If the current course of treatment is not effective, the treatment may be altered. "Altering therapy" is used herein to mean "discontinuing therapy" or "changing the therapy" (e.g., changing the type of treatment, changing the particular dose and/or frequency of administration of a nutritional supplement or medication, e.g., increasing the dose and/or frequency, or changing the diet of the subject, e.g., ketogenic diet). In some cases, therapy can be altered until the individual is deemed to be responsive. In some embodiments, altering therapy means changing which type of treatment is administered, discontinuing a particular treatment altogether, etc.

As a non-limiting illustrative example, a patient may be initially treated by administering a nutritional supplement comprising α-ketoglutarate or a derivative thereof. Then to "continue treatment" would be to continue with these types of treatments. If the current course of treatment is not effective in treating, the disease or disorder associated with retinal degeneration, treatment may be altered, e.g., increasing dosage of α-ketoglutarate or a derivative thereof, administering B vitamins or other nutritional supplements, or placing the subject on a ketogenic diet.

In other words, the level of one or more biomarkers may be monitored in order to determine when to continue therapy and/or when to alter therapy. As such, a post-treatment biological sample (e.g., vitreous sample) can be isolated after any of the administrations and assayed to determine the level of a biomarker. Accordingly, the subject methods can be used to determine whether an individual being treated for a disease or disorder associated with retinal degeneration is responsive or is maintaining responsiveness to a treatment.

The therapy can be administered to an individual any time after a pre-treatment biological sample is isolated from the individual, but it is preferable for the therapy to be administered simultaneous with or as soon as possible (e.g., about 7 days or less, about 3 days or less, e.g., 2 days or less, 36 hours or less, 1 day or less, 20 hours or less, 18 hours or less, 12 hours or less, 9 hours or less, 6 hours or less, 3 hours or less, 2.5 hours or less, 2 hours or less, 1.5 hours or less, 1 hour or less, 45 minutes or less, 30 minutes or less, 20 minutes or less, 15 minutes or less, 10 minutes or less, 5 minutes or less, 2 minutes or less, or 1 minute or less) after a pre-treatment biological sample is isolated (or, when multiple pre-treatment biological samples are isolated, after the final pre-treatment biological sample is isolated).

In some cases, more than one type of therapy may be administered to the individual. For example, a subject may be administered α-ketoglutarate or a derivative thereof. The subject may also be administered a nutritional supplement comprising vitamin B2, vitamin B3, or a combination thereof. Additionally, a subject may be put on a ketogenic diet that reduces carbohydrate intake and increases fat intake.

In some embodiments, the subject methods include providing an analysis indicating whether the individual is determined to have a disease or disorder associated with retinal degeneration. The analysis may further provide an analysis of whether an individual is responsive or not responsive to a treatment, or whether the individual is determined to be maintaining responsiveness or not maintaining responsiveness to a treatment. As described above, an analysis can be an oral or written report (e.g., written or electronic document). The analysis can be provided to the subject, to the subject's physician, to a testing facility, etc. The analysis can also be accessible as a website address via the internet. In some such cases, the analysis can be accessible by multiple different entities (e.g., the subject, the subject's physician, a testing facility, etc.).

Detecting and Measuring Biomarkers

It is understood that the biomarkers in a sample can be measured by any suitable method known in the art. Measurement of the expression level of a biomarker can be direct or indirect. For example, the abundance levels of RNAs or proteins can be directly quantitated. Alternatively, the amount of a biomarker can be determined indirectly by measuring abundance levels of cDNAs, amplified RNAs or DNAs, or by measuring quantities or activities of RNAs, proteins, or other molecules (e.g., metabolites or metabolic byproducts) that are indicative of the expression level of the biomarker. The methods for measuring biomarkers in a sample have many applications. For example, one or more biomarkers can be measured to aid in evaluating the progression of a disease or disorder associated with retinal degeneration (e.g., retinitis pigmentosa) and determining the appropriate treatment for a subject, as well as monitoring responses of a subject to treatment.

In some embodiments, the amount or level in the sample of one or more proteins/polypeptides encoded by a gene of interest is determined. Any convenient protocol for evaluating protein levels may be employed where the level of one or more proteins in the assayed sample is determined. For antibody-based methods of protein level determination, any convenient antibody can be used that specifically binds to the intended biomarker (e.g., rhodopsin, guanine nucleotide-binding protein alpha subunit and beta subunit, phosducin, cyclic nucleotide-gated channel beta 1, rhodopsin kinase, recoverin, and S-arrestin). The terms "specifically binds" or "specific binding" as used herein refer to preferential binding to a molecule relative to other molecules or moieties in a solution or reaction mixture (e.g., an antibody specifically binds to a particular polypeptide or epitope relative to other available polypeptides or epitopes). In some embodiments, the affinity of one molecule for another molecule to which it specifically binds is characterized by a $K_d$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). By "Affinity" it is meant the strength of binding, increased binding affinity being correlated with a lower $K_d$.

While a variety of different manners of assaying for protein levels are known in the art, one representative and convenient type of protocol for assaying protein levels is the enzyme-linked immunosorbent assay (ELISA). In ELISA and ELISA-based assays, one or more antibodies specific for the proteins of interest may be immobilized onto a selected solid surface, preferably a surface exhibiting a protein affinity such as the wells of a polystyrene microtiter plate. After washing to remove incompletely adsorbed material, the assay plate wells are coated with a non-specific "blocking" protein that is known to be antigenically neutral with regard to the test sample such as bovine serum albumin (BSA), casein or solutions of powdered milk. This allows for blocking of non-specific adsorption sites on the immobilizing surface, thereby reducing the background caused by non-specific binding of antigen onto the surface. After washing to remove unbound blocking protein, the immobilizing surface is contacted with the sample to be tested under conditions that are conducive to immune complex (antigen/antibody) formation. Such conditions include diluting the sample with diluents such as BSA or bovine gamma globulin (BGG) in phosphate buffered saline (PBS)/Tween or PBS/Triton-X 100, which also tend to assist in the reduction of nonspecific background, and allowing the sample to incubate for about 2-4 hours at temperatures on the order of about 25°–27° C. (although other temperatures may be used). Following incubation, the antisera-contacted surface is washed so as to remove non-immunocomplexed material. An exemplary washing procedure includes washing with a solution such as PBS/Tween, PBS/Triton-X 100, or borate buffer. The occurrence and amount of immunocomplex formation may then be determined by subjecting the bound immunocomplexes to a second antibody having specificity for the target that differs from the first antibody and detecting binding of the second antibody. In certain embodiments, the second antibody will have an associated enzyme, e.g. urease, peroxidase, or alkaline phosphatase, which will generate a color precipitate upon incubating with an appropriate chromogenic substrate. For example, a urease or peroxidase-conjugated anti-human IgG may be employed, for a period of time and under conditions which favor the development of immunocomplex formation (e.g., incubation for 2 hours at room temperature in a PBS-containing solution such as PBS/Tween). After such incubation with the second antibody and washing to remove unbound material, the amount of label is quantified, for example by incubation with a chromogenic substrate such as urea and bromocresol purple in the case of a urease label or 2,2'-azino-di-(3-ethyl-benzthiazoline)-6-sulfonic acid (ABTS) and $H_2O_2$, in the case of a peroxidase label. Quantitation is then achieved by measuring the degree of color generation, e.g., using a visible spectrum spectrophotometer. The preceding format may be altered by first binding the sample to the assay plate. Then, primary antibody is incubated with the assay plate, followed by detecting of bound primary antibody using a labeled second antibody with specificity for the primary antibody.

The solid substrate upon which the antibody or antibodies are immobilized can be made of a wide variety of materials and in a wide variety of shapes, e.g., microtiter plate, microbead, dipstick, resin particle, etc. The substrate may be chosen to maximize signal to noise ratios, to minimize background binding, as well as for ease of separation and cost. Washes may be effected in a manner most appropriate for the substrate being used, for example, by removing a bead or dipstick from a reservoir, emptying or diluting a reservoir such as a microtiter plate well, or rinsing a bead, particle, chromatographic column or filter with a wash solution or solvent.

Alternatively, non-ELISA based-methods for measuring the levels of one or more proteins in a sample may be employed and any convenient method may be used. Representative examples known to one of ordinary skill in the art include but are not limited to other immunoassay techniques such as radioimmunoassays (RIA), sandwich immunoassays, fluorescent immunoassays, enzyme multiplied immunoassay technique (EMIT), capillary electrophoresis immunoassays (CEIA), and immunoprecipitation assays; mass spectrometry (MS), tandem mass spectrometry (MS/MS), tandem liquid chromatography mass spectrometry (LC-MS/MS), proteomic arrays, xMAP microsphere technology, western blotting, immunohistochemistry, flow cytometry, cytometry by time-of-flight (CyTOF), multiplexed ion beam imaging (MIBI), and detection in body fluid by electrochemical sensor. In, for example, flow cytometry methods, the quantitative level of gene products of the one or more genes of interest are detected on cells in a cell suspension by lasers. As with ELISAs and immunohistochemistry, antibodies (e.g., monoclonal antibodies) that specifically bind the polypeptides encoded by the genes of interest are used in such methods.

As another example, electrochemical sensors may be employed. In such methods, a capture aptamer or an antibody that is specific for a target protein (the "analyte") is immobilized on an electrode. A second aptamer or antibody, also specific for the target protein, is labeled with, for example, pyrroquinoline quinone glucose dehydrogenase ((PQQ)GDH). The sample of body fluid is introduced to the sensor either by submerging the electrodes in body fluid or by adding the sample fluid to a sample chamber, and the analyte allowed to interact with the labeled aptamer/antibody and the immobilized capture aptamer/antibody. Glucose is then provided to the sample, and the electric current generated by (PQQ)GDH is observed, where the amount of electric current passing through the electrochemical cell is directly related to the amount of analyte captured at the electrode.

Flow cytometry can be used to distinguish subpopulations of cells expressing different cellular markers and to determine their frequency in a population of cells. Typically, whole cells are incubated with antibodies that specifically bind to the cellular markers. The antibodies can be labeled, for example, with a fluorophore, isotope, or quantum dot to facilitate detection of the cellular markers. The cells are then suspended in a stream of fluid and passed through an electronic detection apparatus. In addition, fluorescence-activated cell sorting (FACS) can be used to sort a heterogeneous mixture of cells into separate containers. (See, e.g., Shapiro *Practical Flow Cytometry*, Wiley-Liss, 4th edition, 2003; Loken *Immunofluorescence Techniques in Flow Cytometry and Sorting*, Wiley, 2nd edition, 1990; *Flow Cytometry: Principles and Applications*, (ed. Macey), Humana Press 1st edition, 2007; herein incorporated by reference in their entireties.)

Cytometry by time-of-flight (CyTOF), also known as mass cytometry, is a method that can be used for detection of cellular markers in whole cells. CyTOF uses transition element isotopes as labels for antibodies, which are detected by a time-of-flight mass spectrometer. Unlike conventional flow cytometry, CyTOF is destructive to cells, but has the advantage that it can be used to analyze more cell markers simultaneously. See, e.g., Bendall et al. (2012) Trends in Immunology 33:323-332; Newell et al. (2012) Immunity 36(1):142-52; Ornatsky et al. (2010) J. Immunol. Methods 361 (1-2):1-20; Bandura et al. (2009) Analytical Chemistry 81:6813-6822; Chen et al. (2012) Cell Mol. Immunol. 9(4):322-323; and Cheung et al. (2011) Nat. Rev. Rheumatol. 7(9):502-3; herein incorporated by reference in their entireties.

In addition, multiplexed ion beam imaging (MIBI) can be used to distinguish subpopulations of cells carrying different cellular markers. MIBI uses secondary ion mass spectrometry to image antibodies that are tagged with isotopically pure elemental metal reporters. Not only can MIBI measure protein levels on individual cells, but also, the technique is capable of providing information about cell morphology and localization. Like CYTOF, MIBI is capable of analyzing a large number of cell markers (e.g., up to 100) simultaneously over a five-log dynamic range. See, e.g., Angelo et al. (2014) Nat. Med. 20(4):436-442; Bodenmiller et al. (2016) Cell Syst. 2(4):225-238; and Levenson et al. (2015) Lab Invest. 95(4):397-405; herein incorporated by reference in their entireties.

For measuring protein activity levels, the amount or level of protein activity in the sample of one or more proteins/ polypeptides encoded by the gene of interest is determined.

In other embodiments, the amount or level in the sample of one or more RNAs encoded by a gene of interest is determined. Any convenient method for measuring mRNA levels in a sample may be used, e.g. hybridization-based methods, e.g. northern blotting and in situ hybridization (Parker & Barnes, Methods in Molecular Biology 106:247-283 (1999)), RNase protection assays (Hod, Biotechniques 13:852-854 (1992)), and PCR-based methods (e.g. reverse transcription PCR (RT-PCR) (Weis et al., Trends in Genetics 8:263-264 (1992)). Alternatively, any convenient method for measuring protein levels in a sample may be used, e.g. antibody-based methods, e.g. immunoassays, e.g., enzyme-linked immunosorbent assays (ELISAs), immunohistochemistry, and flow cytometry (FACS).

For measuring mRNA levels, the starting material may be total RNA, i.e. unfractionated RNA, or poly A+ RNA isolated from a suspension of cells. General methods for mRNA extraction are well known in the art and are disclosed in standard textbooks of molecular biology, including Ausubel et al., Current Protocols of Molecular Biology, John Wiley and Sons (1997). RNA isolation can also be performed using a purification kit, buffer set and protease from commercial manufacturers, according to the manufacturer's instructions. For example, RNA from cell suspensions can be isolated using Qiagen RNeasy mini-columns, and RNA from cell suspensions or homogenized tissue samples can be isolated using the TRIzol reagent-based kits (Invitrogen), MasterPure™ Complete DNA and RNA Purification Kit (EPICENTRE™, Madison, Wis.), Paraffin Block RNA Isolation Kit (Ambion, Inc.) or RNA Stat-60 kit (Tel-Test).

The mRNA levels may be measured by any convenient method. Examples of methods for measuring mRNA levels may be found in, e.g., the field of differential gene expression analysis. One representative and convenient type of protocol for measuring mRNA levels is array-based gene expression profiling. Such protocols are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively.

Specific hybridization technology which may be employed in the subject methods includes that described in U.S. Pat. Nos. 5,143,854; 5,288,644; 5,324,633; 5,432,049;

5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions, and unbound nucleic acid is then removed. The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

The resultant pattern of hybridized nucleic acid provides information regarding expression for each of the genes that have been probed, where the expression information is in terms of whether or not the gene is expressed and, typically, at what level, where the expression data, i.e., expression profile (e.g., in the form of a transcriptosome), may be both qualitative and quantitative.

Additionally or alternatively, non-array based methods for quantitating the level of one or more nucleic acids in a sample may be employed. These include those based on amplification protocols, e.g., Polymerase Chain Reaction (PCR)-based assays, including quantitative PCR, reverse-transcription PCR (RT-PCR), real-time PCR, and the like, e.g. TaqMan, RT-PCR, MassARRAY System, BeadArray technology, and Luminex technology; and those that rely upon hybridization of probes to filters, e.g. Northern blotting and in situ hybridization. Serial Analysis Gene Expression (SAGE) can also be used to determine RNA abundances in a cell sample. See, e.g., Velculescu et al., 1995, Science 270:484-7; Carulli, et al., 1998, Journal of Cellular Biochemistry Supplements 30/31:286-96; herein incorporated by reference in their entireties. SAGE analysis does not require a special device for detection, can be used for simultaneously detecting the expression of large numbers of transcription products.

The resultant data provides information regarding expression, amount, and/or activity for each of the biomarkers that have been measured, wherein the information is in terms of whether or not the biomarker is present (e.g. expressed) and at what level, and wherein the data may be both qualitative and quantitative.

Data Analysis

In some embodiments, one or more pattern recognition methods can be used in analyzing the data for biomarker levels. The quantitative values may be combined in linear or non-linear fashion to diagnose an individual with a disease or disorder associated with retinal degeneration (e.g., retinitis pigmentosa) and/or monitor retinal degeneration. In some embodiments, measurements for a biomarker or combinations of biomarkers are formulated into linear or non-linear models or algorithms (e.g., a 'biomarker signature') and converted into a likelihood score. This likelihood score indicates the probability that a vitreous or retinal sample is from a patient who exhibits no evidence of disease or a patient who has a disease or disorder associated with retinal degeneration (e.g., retinitis pigmentosa). The likelihood score can be used to distinguish disease states (e.g., stage of disease progression, extent of retinal degeneration, or photoreceptor cell loss). The models and/or algorithms can be provided in machine readable format, and may be used to correlate biomarker levels or a biomarker profile with a disease state, and/or to designate a treatment modality for a patient or class of patients.

Analyzing the levels of a plurality of biomarkers may comprise the use of an algorithm or classifier. In some embodiments, a machine learning algorithm is used to classify a patient as having a positive or negative diagnosis for a disease or disorder associated with retinal degeneration (e.g., retinitis pigmentosa). For example, a machine learning algorithm may be used for computing a risk score for retinitis pigmentosa. The machine learning algorithm may comprise a supervised learning algorithm. Examples of supervised learning algorithms may include Average One-Dependence Estimators (AODE), Artificial neural network (e.g., Backpropagation), Bayesian statistics (e.g., Naive Bayes classifier, Bayesian network, Bayesian knowledge base), Case-based reasoning, Decision trees, Inductive logic programming, Gaussian process regression, Group method of data handling (GMDH), Learning Automata, Learning Vector Quantization, Minimum message length (decision trees, decision graphs, etc.), Lazy learning, Instance-based learning Nearest Neighbor Algorithm, Analogical modeling, Probably approximately correct learning (PAC) learning, Ripple down rules, a knowledge acquisition methodology, Symbolic machine learning algorithms, Subsymbolic machine learning algorithms, Support vector machines, Random Forests, Ensembles of classifiers, Bootstrap aggregating (bagging), and Boosting. Supervised learning may comprise ordinal classification such as regression analysis and Information fuzzy networks (IFN). Alternatively, supervised learning methods may comprise statistical classification, such as AODE, Linear classifiers (e.g., Fisher's linear discriminant, Logistic regression, Naive Bayes classifier, Perceptron, and Support vector machine), quadratic classifiers, k-nearest neighbor, Boosting, Decision trees (e.g., C4.5, Random forests), Bayesian networks, and Hidden Markov models.

The machine learning algorithms may also comprise an unsupervised learning algorithm. Examples of unsupervised learning algorithms may include artificial neural network, Data clustering, Expectation-maximization algorithm, Self-organizing map, Radial basis function network, Vector Quantization, Generative topographic map, Information bottleneck method, and IBSEAD. Unsupervised learning may also comprise association rule learning algorithms such as Apriori algorithm, Eclat algorithm and FP-growth algorithm. Hierarchical clustering, such as Single-linkage clustering and Conceptual clustering, may also be used. Alternatively, unsupervised learning may comprise partitional clustering such as K-means algorithm and Fuzzy clustering.

In some instances, the machine learning algorithms comprise a reinforcement learning algorithm. Examples of reinforcement learning algorithms include, but are not limited to, temporal difference learning, Q-learning and Learning Automata. Alternatively, the machine learning algorithm may comprise Data Pre-processing.

Preferably, the machine learning algorithms may include, but are not limited to, Average One-Dependence Estimators (AODE), Fisher's linear discriminant, Logistic regression, Perceptron, Multilayer Perceptron, Artificial Neural Networks, Support vector machines, Quadratic classifiers, Boosting, Decision trees, C4.5, Bayesian networks, Hidden Markov models, High-Dimensional Discriminant Analysis, and Gaussian Mixture Models. The machine learning algorithm may comprise support vector machines, Naïve Bayes classifier, k-nearest neighbor, high-dimensional discriminant analysis, or Gaussian mixture models. In some instances, the machine learning algorithm comprises Random Forests.

Kits

Also provided are kits for use in the methods. In some embodiments, α-ketoglutarate or a derivative thereof is provided in a dosage form (e.g., a therapeutically effective dosage form). Other agents may also be included in the kit such as other neuroprotective agents or nutritional supplements such as vitamin A, vitamin B2, vitamin B3, retinyl palmitate, docosahexaenoic acid (DHA), lutein, or a combination thereof. In some embodiments, a nutritional supplement comprising α-ketoglutarate, vitamin B2, and vitamin B3 is included in the kit.

In other embodiments, the subject kits may include agents (e.g., an antibody that specifically binds to a biomarker and/or other immunoassay reagents, and the like) for determining the level of at least one biomarker. In some embodiments, a kit comprises agents for determining the level of a single biomarker, two or more different biomarkers, or all the biomarkers selected from the group consisting of rhodopsin, guanine nucleotide-binding protein alpha subunit and beta subunit, phosducin, cyclic nucleotide-gated channel beta 1, rhodopsin kinase, recoverin, and S-arrestin.

In the context of a kit, any of these agents can be provided in liquid or sold form in any convenient packaging (e.g., stick pack, dose pack, etc.). The agents of a kit can be present in the same or separate containers. The agents may also be present in the same container. In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Proteomic analysis of the vitreous may serve as way to indirectly biopsy the neural retina during early degeneration and identify changes in the retinal proteome. Therefore, we collected vitreous biopsy samples from two autosomal recessive (ar)RP patients carrying mutations in PDE6A (OMIM: 180071). PDE6 mutations contribute to a significant fraction of RP cases (7-9%) and the PDE6A gene encodes the catalytic α-subunit of the rod-specific cGMP-dependent phosphodiesterase (PDE), a key component of the phototransduction cascade that is responsible for the hydrolysis of cGMP in the rod photoreceptor outer segment. Furthermore, we have previously characterized the $Pde6\alpha^{D670G}$ (C57BL/6J-Pde6$\alpha^{nmf363/nmf363}$) arRP preclinical mouse model and were the first to show long-term visual rescue after AAV supplementation gene therapy. Similar to human arRP patients, the $Pde6\alpha^{D670G}$ mice harbor a point mutation in the Pde6a gene that disrupts a highly conserved residue near the cGMP-binding site of the catalytic subunit. These mice develop early onset severe retinal degeneration, characterized by photoreceptor death, retinal vessel attenuation, pigmented patches, ERG abnormalities, and white retinal spotting. Thus, this mouse model reflects the human arRP clinical phenotype and neuronal cell death progression and can be used to detect early neural retinal changes during RP disease.

To identify potential vitreous biomarkers for neural retinal degeneration, we studied protein expression in the $Pde6\alpha^{D670G}$ arRP mouse model. Tandem liquid chromatography mass spectrometry (LC-MS/MS) was performed on both retina and vitreous samples in wild-type and $Pde6\alpha^{D670G}$ mice during early (post-natal day 15), middle (post-natal day 30) and late stage (post-natal day 90) disease. To our knowledge, this is the first extensive dataset on an RP mouse model and the first to show how the various molecular pathways change during the progression of neuronal degeneration.

We then used our proteomics dataset to interrogate the top cellular pathways disrupted at the onset of rod photoreceptor cell death (P15 in our mouse model) and targeted these critical pathways to investigate non-pharmacologic treatments for RP patients, regardless of their specific genetic mutation. Additionally, we validated our mouse proteomic dataset to those found up-regulated within the vitreous of our two human arRP patients in late stages of neuronal degeneration and neural retinal network loss. Based on the human and mouse analysis, we provided mice with oral supplementation of metabolites involved in oxidative phosphorylation and the tricarboxylic acid (TCA) cycle, the critical metabolic pathways found to be disrupted at the onset of rod dystrophy. We found that restoration of the TCA cycle by dietary supplementation of a single metabolite, alpha-ketoglutarate, was able to significantly prolong photoreceptor cell survival and visual function in the arRP mouse model for at least one month of age. Overall, this study not only provides important information on the molecular pathways that may play a role at the onset of neurodegenerative diseases, but we found that replenishing specific metabolites via oral supplementation can prolong vision and provide a neuroprotective effect in our preclinical model system. The TCA cycle, along with other cellular pathways we identified in our proteomics dataset, are potential therapeutic targets for the treatment of arRP, as well as applicable to other vitreoretinopathies and diseases presenting with neuronal cell loss.

Results

Proteomics of the Human Vitreous Highlight Changes Occurring in the Neural Retina During RP Disease Progression.

Figure 1B:
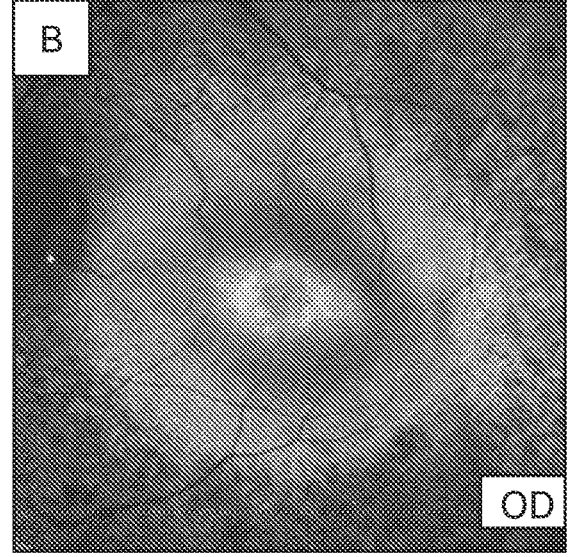
Figure 1C:
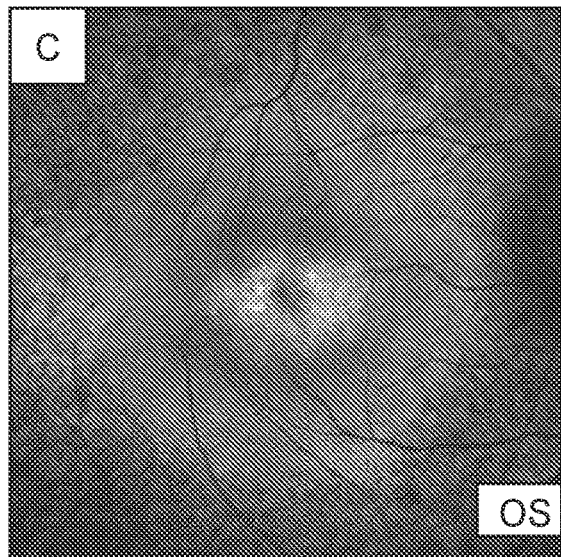
Figure 1D:
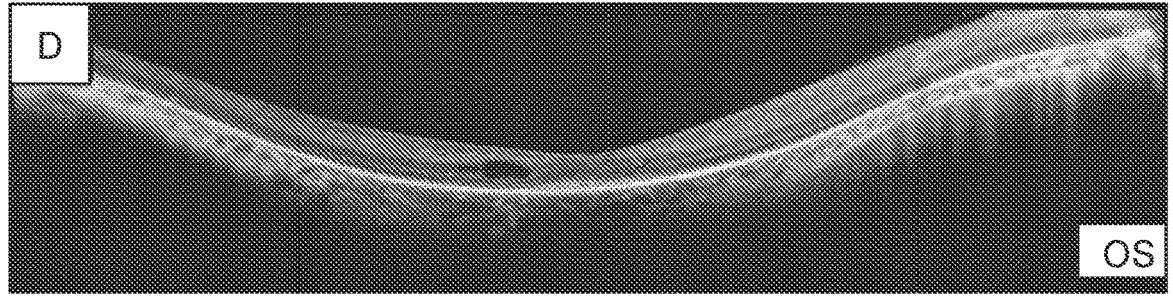
Figure 1E:
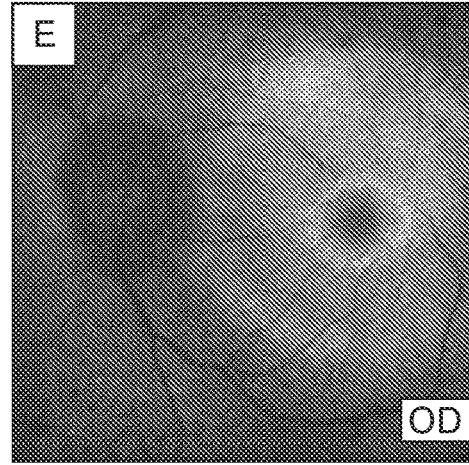
Figure 1F:
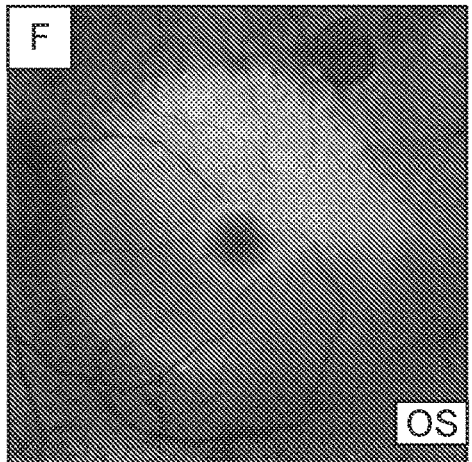
Figure 1G:
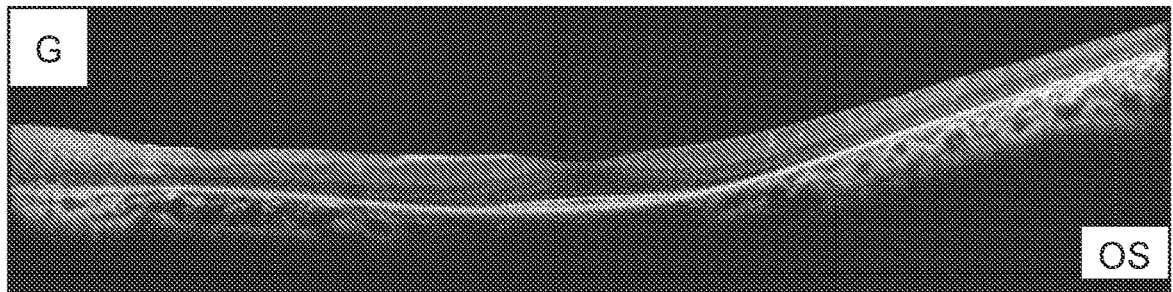

In human patients, neural retina biopsies are rare and highly invasive, and result in a loss of visual response as neuronal cells are excised from the patient eye. However, the vitreous humor is an optically-transparent extracellular matrix located in the posterior chamber of the eye, just anterior to the neural retinal network, and is an easily accessible biopsy site.[2-5] We have previously shown that proteomic analysis of the adjacent vitreous in humans serves as way to indirectly biopsy the neural retina during early degeneration and identify changes in the retinal proteome.[2, 4-8] Vitreous samples were collected from a patient with arRP harboring a p.R102C/p.S303C mutation in the PDE6A gene (II:5; FIG. 1A). (1) This patient presented with extensive peripheral intra-retinal pigment migration on color fundus imaging (FIG. 1B-C). Fundus autofluorescence (AF) revealed high-density central AF rings (FIG. 1C) and optical coherence tomography (OCT) revealed thinning of the neuronal cell layers (FIG. 1D). The patient developed a significant epiretinal membrane and underwent vitrectomy surgery (Supplemental Video 1) and the vitreous biopsy was collected at this time. Additionally, the proband's affected brother (II:4) displayed similar intra-retinal pigment migration (FIG. 1E-F) and hyper-auto-fluorescent rings on AF imaging (FIG. 1F). OCT imaging similarly revealed thinning of retinal cell layers and cystoid macular edema (FIG. 1G). Vitreous biopsies were also taken from the affected brother (11:4), two patients with epiretinal membranes (ERM), three controls with idiopathic macular holes (IMH) or vitreous opacities (Table 1) for proteomic analysis.

$Pde6\alpha^{D670G}$ Mice Display Neuronal Degeneration and Impaired Retinal Function Mimicking Human arRP.

Figure 2A:
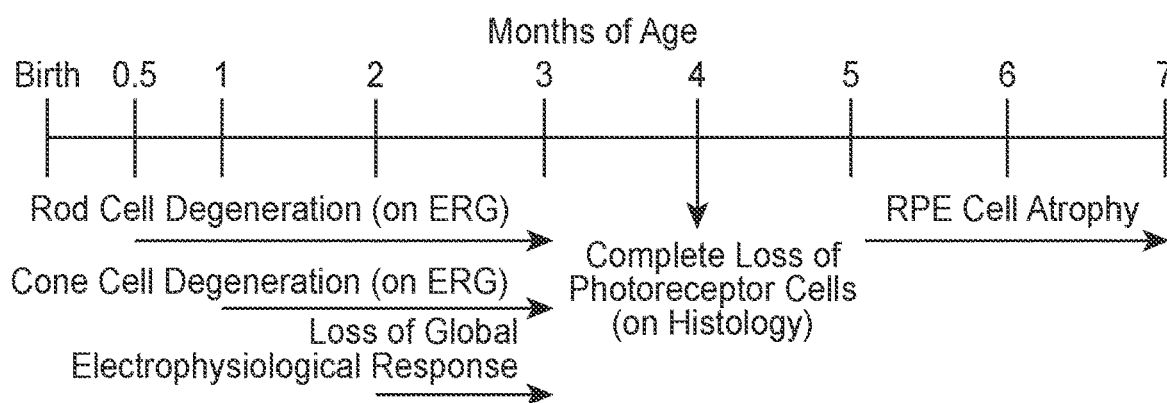
FIGS. 2A-2D show that $Pde6\alpha^{D670G}$ mice display photoreceptor degeneration and impaired retinal function mimicking human retinitis pigmentosa (RP).
Figure 2B:
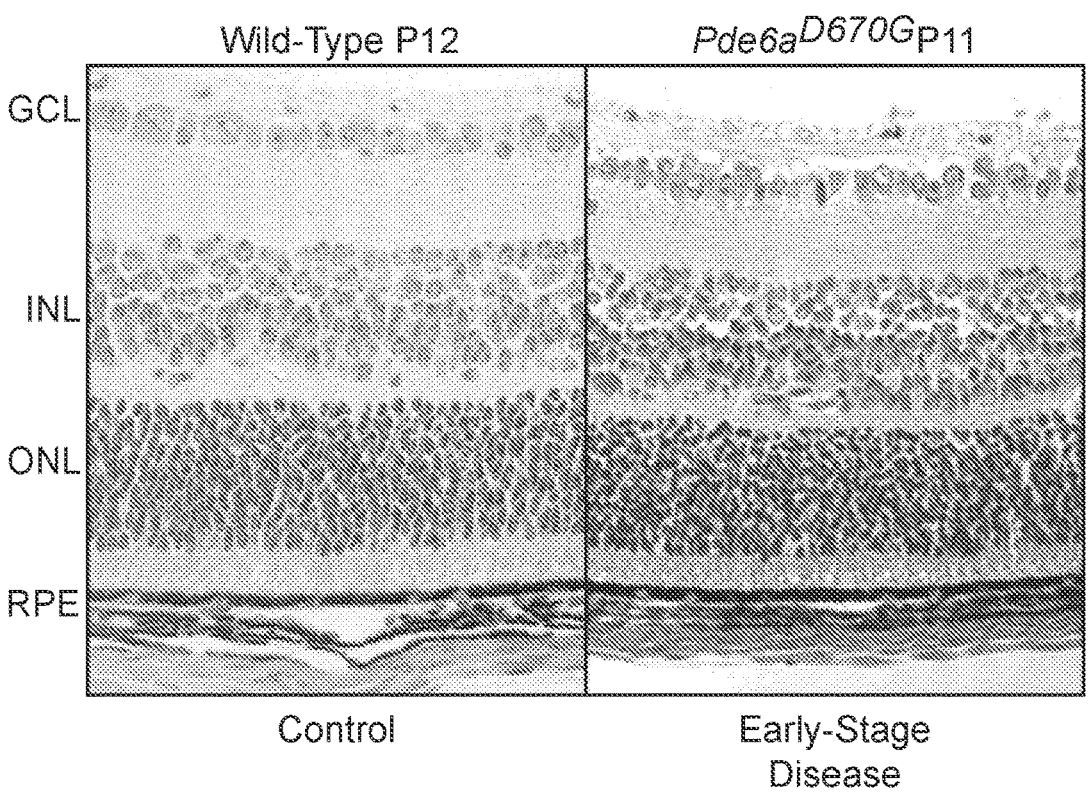
Figure 2B:
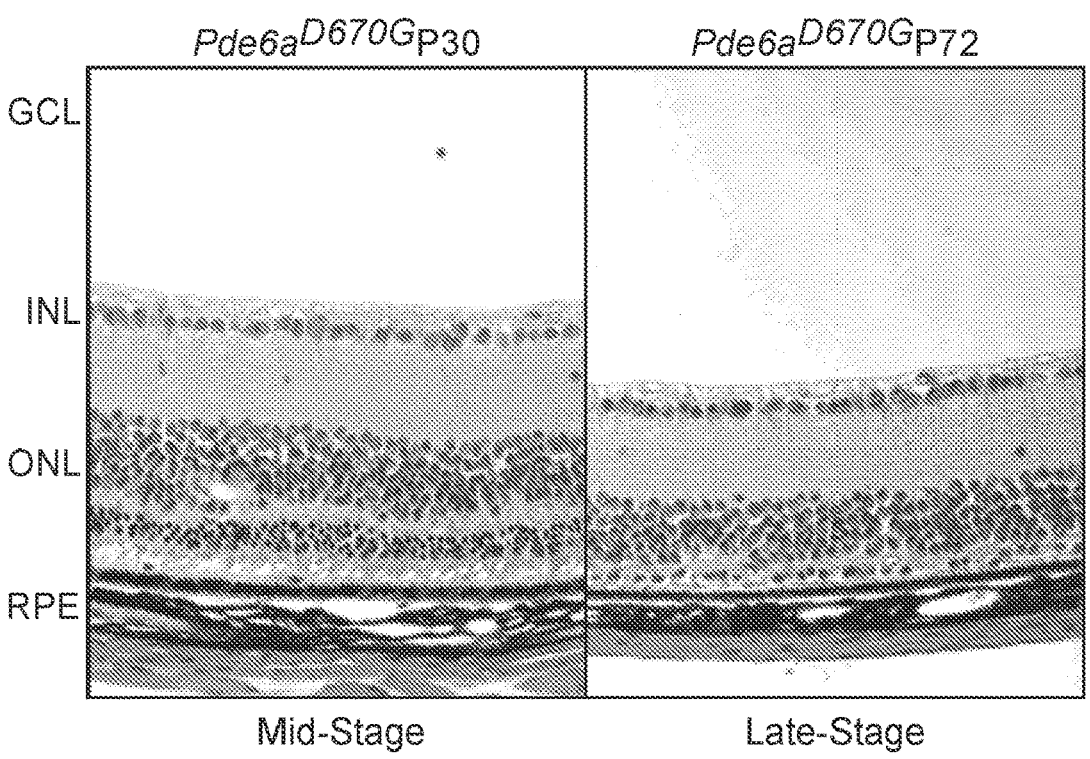
Figure 2C:
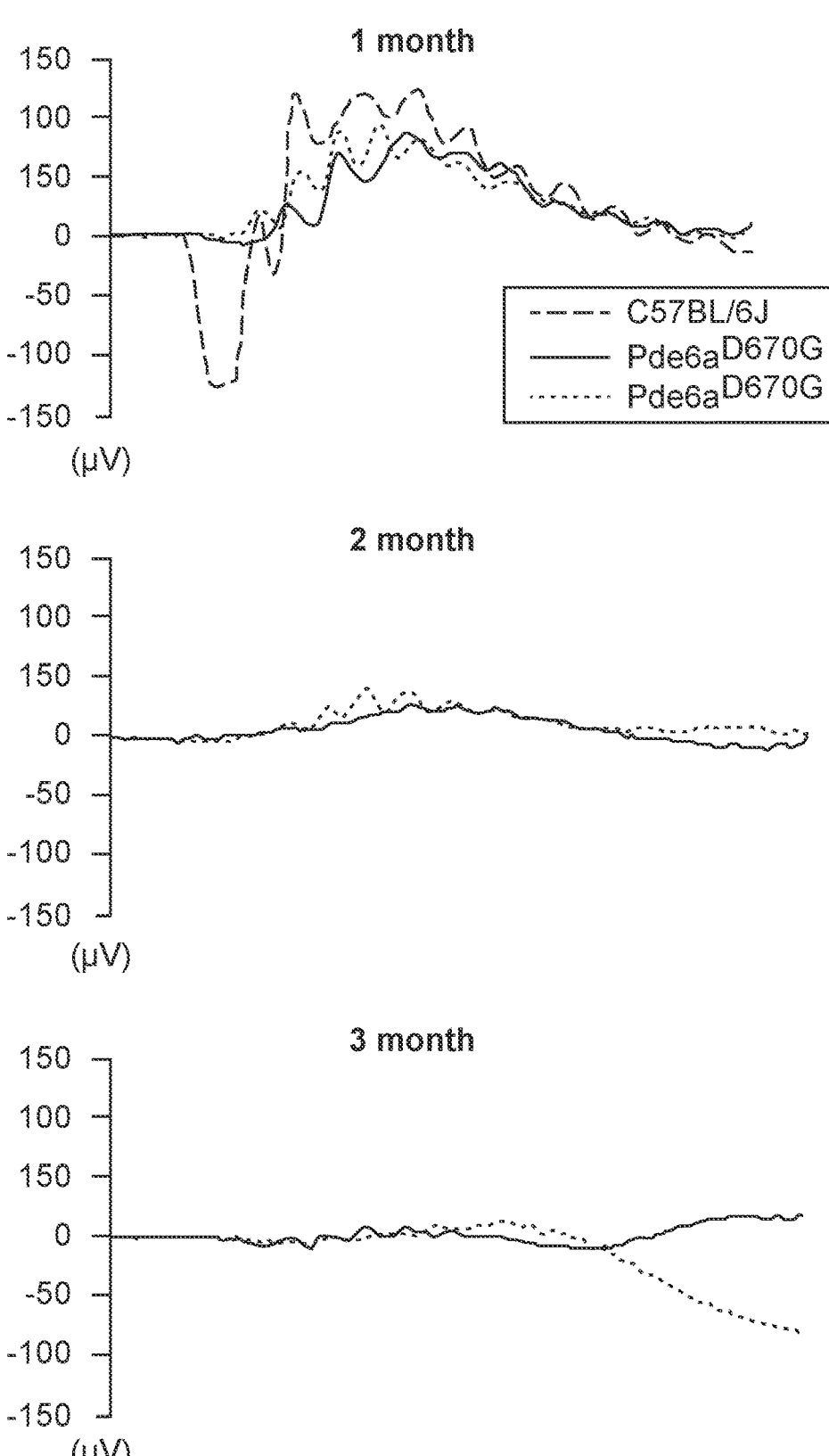
Figure 2D:
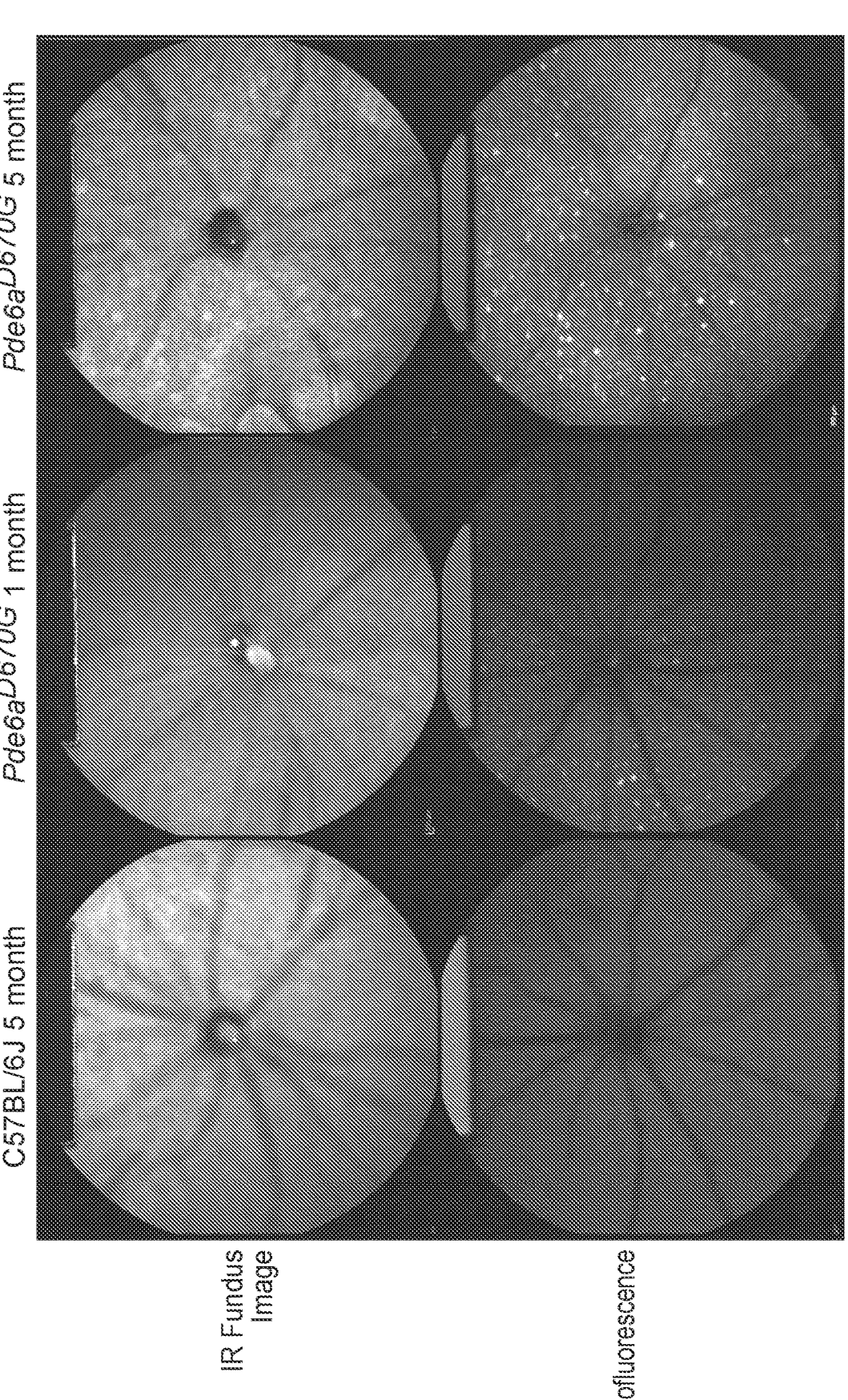

To determine whether changes in the human arRP vitreous proteome would reflect key pathologic markers of neuronal cell death and provide examples of potential targets for early detection and therapeutic applications, we first examined the arRP preclinical mouse model. We have previously characterized and published genetic therapy approaches for the $Pde6\alpha^{D670G}$ mouse.[11-13] The $Pde6\alpha^{D670G}$ phenotype closely resembles that of patients with arRP: presenting with early-onset severe neurodegeneration, characterized by photoreceptor death, retinal vessel attenuation, pigmented patches, electroretinogram (ERG) abnormalities, and white retinal spotting (FIG. 2A). These mice display a loss of rod photoreceptor visual function by ERG analysis as early as one month of age (FIG. 2C) and full loss of global visual function on ERG analysis by two months of age (FIG. 2C). RPE atrophy and neural retinal remodeling is detectable by AF and infrared imaging beginning at 5 months of age (FIG.

2D). In particular, Pde6α$^{D670G}$ mice do not display histologically-detectable photoreceptor degeneration until after post-natal day 14 (P14; FIG. 2B), so we collected retina and vitreous samples from these mice at disease onset (P15), mid-stage (P30) and late-stage disease (P90; FIG. 2B).

Proteomic Analysis of Pde6α$^{D670G}$ Retina and Vitreous Identifies Global Protein Expression Changes.

Retina and vitreous samples for wild-type (at 90 days of age) and Pde6α$^{D670G}$ mice (at 15, 30, and 90 days of age) were trypsinized and underwent multidimensional liquid chromatography before mass spectrometry analysis (FIG. 9; Table 2). Notably there were fewer distinguishable proteins in the Pde6α$^{D670G}$ mouse retina at 90 days (484±63 individual proteins) than 15 days (1,135±55 individual proteins), suggesting a decrease in protein expression as neurodegeneration progresses in the preclinical model (Table 2). Conversely, we noticed there were more distinguishable proteins in the Pde6α$^{D670G}$ mouse vitreous at 15 days (364±30 individual proteins) compared to wild-type vitreous (202±9 individual proteins), suggesting an increase in vitreous protein expression at early stages of neuronal cell death (Table 2).

To obtain a global view of the Pde6α$^{D670G}$ retina and vitreous proteomes at different stages of degeneration, a gene ontology (GO) analysis of highly-represented proteins in each group was performed. When comparing the four total retinal protein profiles, the GO summaries for the control retina were similar to the Pde6α$^{D670G}$ retina at P30 and P90. The highest represented categories were cellular process, catalytic activity, and intracellular regions (FIG. 10). Interestingly, there was a decrease in the number of proteins with transporter activity in the Pde6α$^{D670G}$ retina at early stage neuronal cell death, consistent with a loss of protein expression at this stage (FIG. 10). When comparing the four total vitreous protein profiles, the GO summaries were distinct. Vitreous proteins differed in the molecular function and cellular compartment representation at each disease stage. For example, there was an increase in the number of membrane-bound proteins and macromolecular complexes detected in the Pde6α$^{D670G}$ vitreous at early stage neurodegeneration when compared to control vitreous (FIG. 11). Together, this indicated that the arRP retina and vitreous express distinct functional categories of proteins compared to wild-type mice at each stage of disease progression, and that these protein pathways may reflect targets for therapeutics preventing further neuronal cell death and loss of the neural retinal network.

Oxidative Metabolic Pathways are Downregulated in the Pde6α$^{D670G}$ Retina at the Onset of Neuronal Cell Death.

Figure 3A:
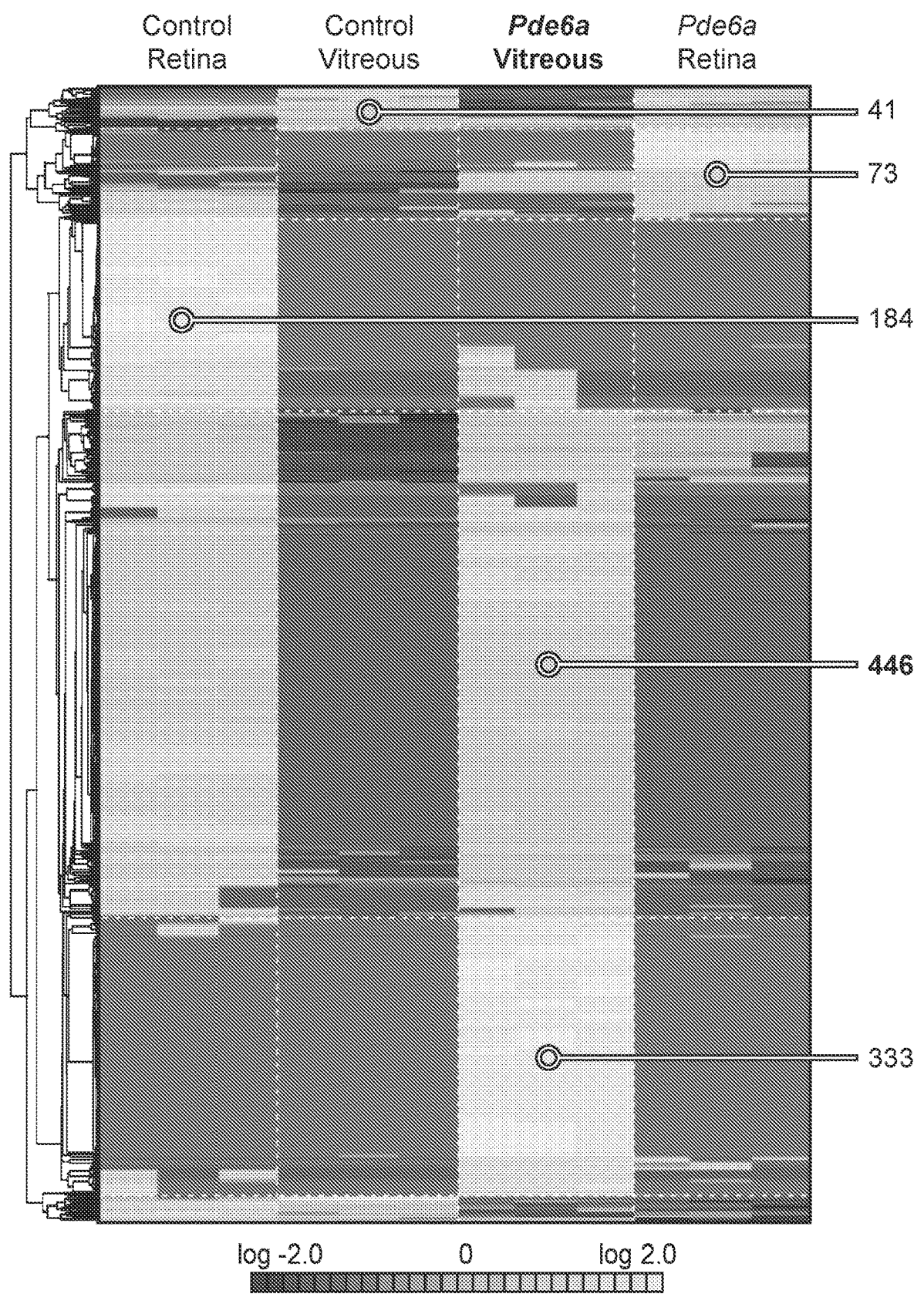
FIGS. 3A-3D show that proteomic analysis of $Pde6\alpha^{D670G}$ retina and vitreous identifies global protein expression changes.
Figure 3B:
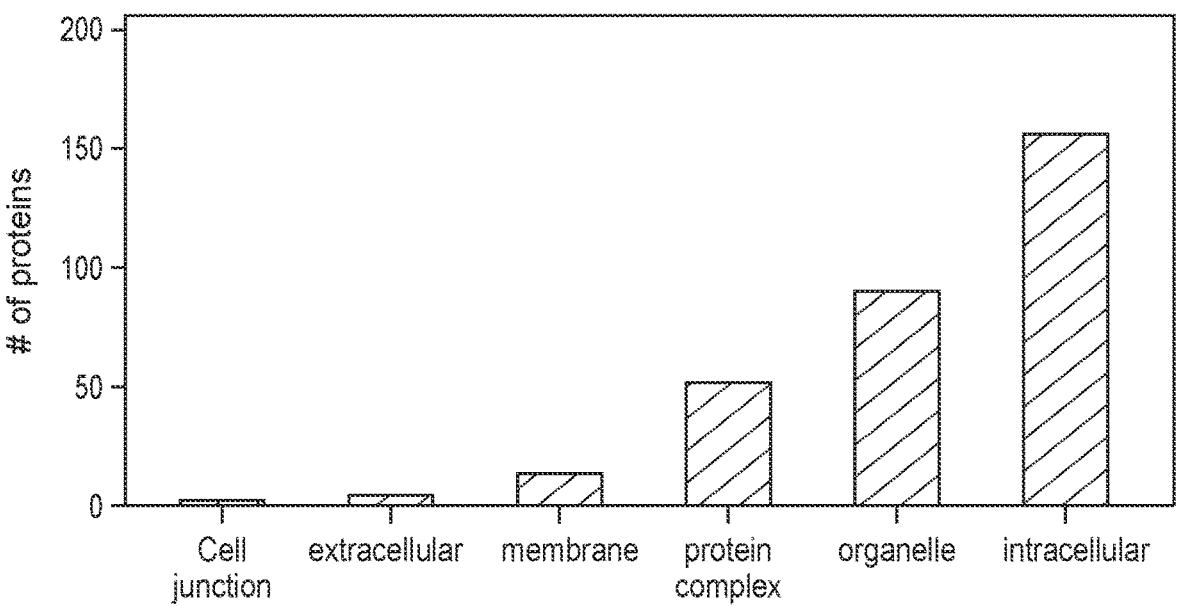
Figure 3C:
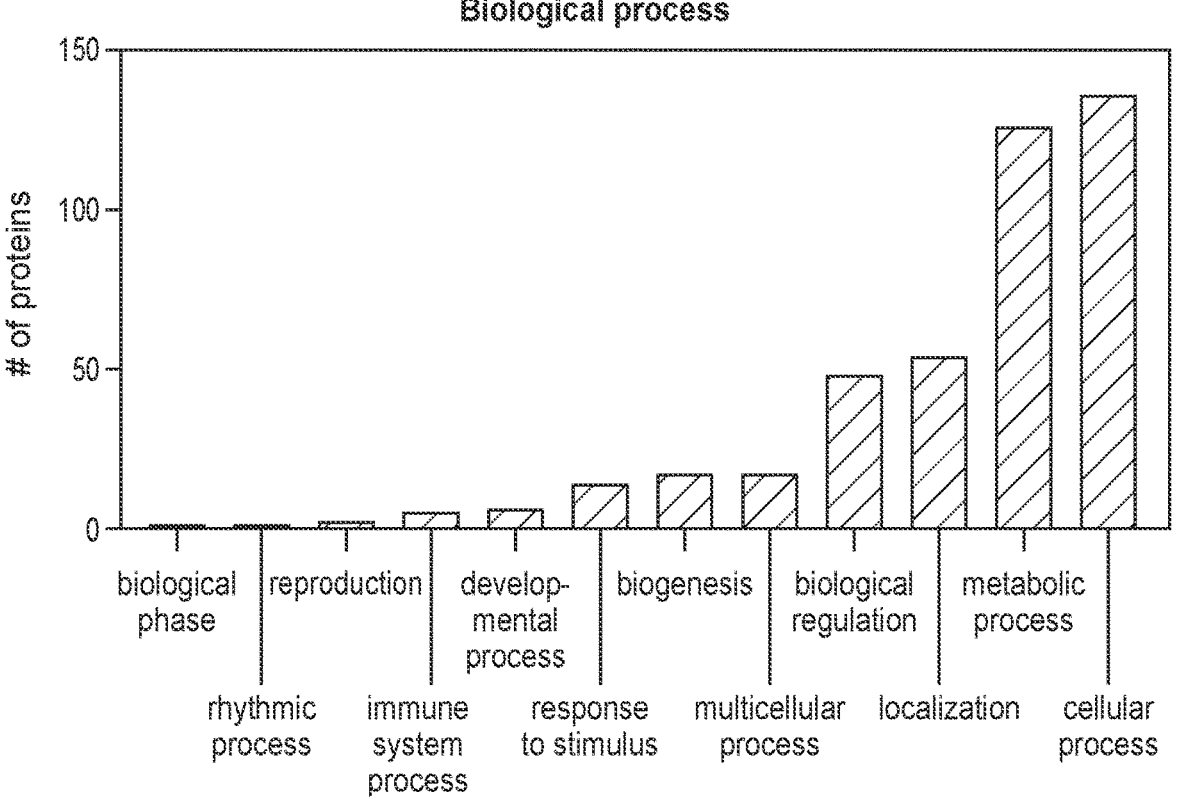
Figure 3D:
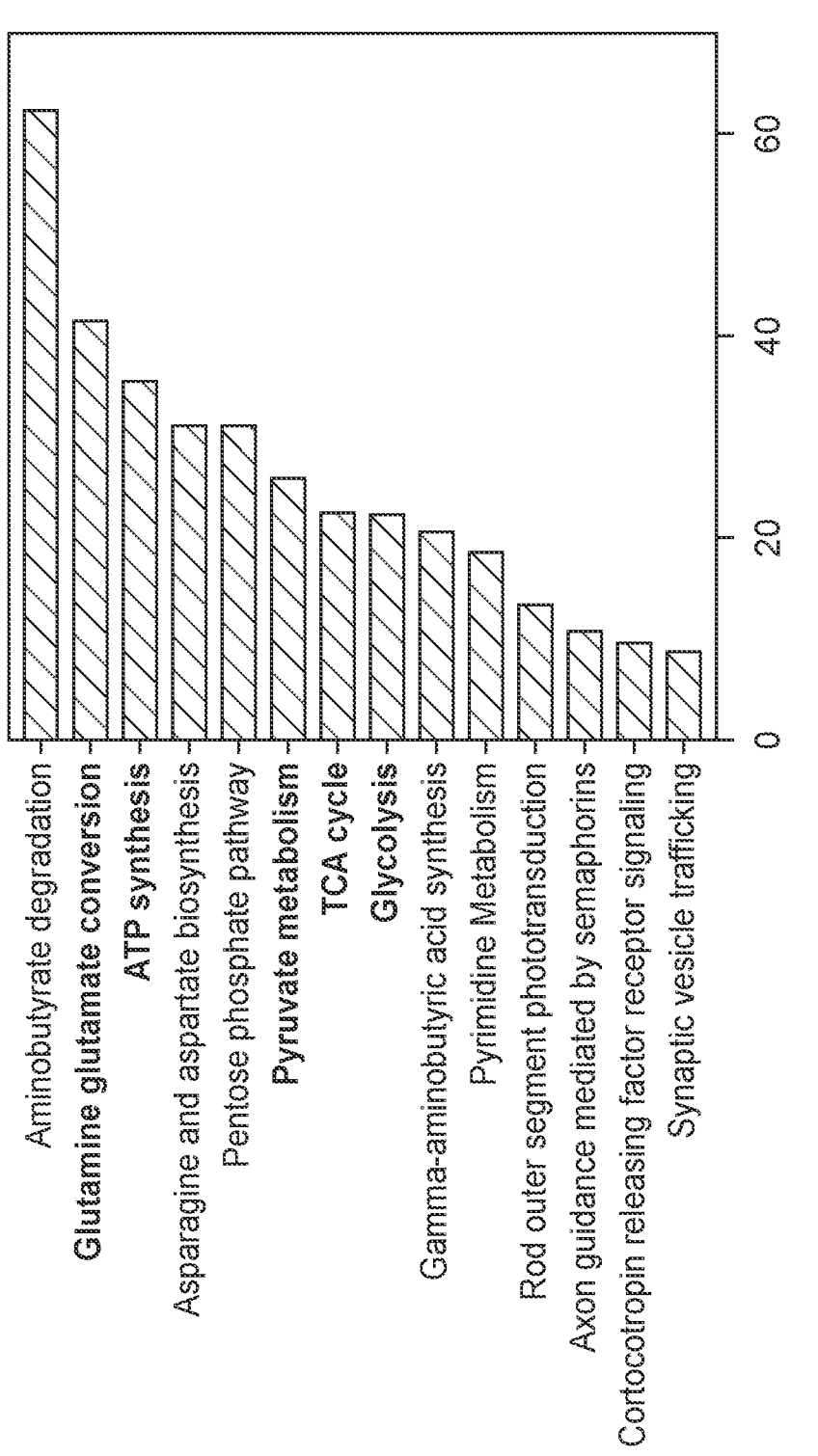

Vitreous and retina protein levels (with two or more spectra) from Pde6α$^{D670G}$ (P15) and wild-type mice were compared using 1-way ANOVA and hierarchical heatmap clustering. A total of 1,067 proteins were differentially-expressed in the Pde6α$^{D670G}$ samples compared to controls (p<0.05; FIG. 3A). There was a significant decrease in protein expression in Pde6α$^{D670G}$ retina at early stage neurodegeneration (P15) compared to controls. There was also a significant increase in protein expression at the onset of neuronal cell death in the Pde6α$^{D670G}$ vitreous compared to controls (779 upregulated proteins; p<0.05). The decrease in retinal protein expression and corresponding increase in vitreous protein expression suggested that the degenerating neural retina may leak proteins into the vitreous, similar to that seen in human patient samples. We compared the list of proteins highly-abundant in control mouse retinas to that of the upregulated proteins in Pde6α$^{D670G}$ vitreous at the onset of neuronal cell death (P15). There were 446 proteins that were expressed in the control retina that were found to be elevated in the P15 Pde6α$^{D670G}$ vitreous (FIG. 3A). These proteins were not present in control vitreous. GO analysis categorized a significant fraction of these proteins to be intracellular, suggesting that they have migrated from the degenerating neural retina into the extracellular vitreous (FIG. 3B). Categorization of these 446 proteins by their biological process revealed that a significant fraction were involved in metabolic processes (FIG. 3C). Pathway analysis revealed that these proteins represent metabolic (e.g. glycolysis, TCA cycle), synaptic signaling, and visual transduction pathways (FIG. 3D). As expected, we found key proteins involved in the rod photoreceptor transduction pathway to be upregulated in the arRP vitreous at the onset of rod cell degeneration (P15): rhodopsin (Rho), guanine nucleotide-binding protein alpha and beta subunits (Gnat1 and Gnb1), phosducin (Pdc), cyclic nucleotide-gated channel beta 1 (Cngb1), rhodopsin kinase (Grk1), recoverin (Rcvrn), and S-arrestin (Sag). Taken together, these results are suggestive that these 446 candidate proteins are biomarkers for early arRP detection and possible targets for neuroprotective therapeutics.

Replenishing Oxidative Phosphorylation with Oral Supplementation of Metabolites Provides a Mild, but Variable, Rescue of Neuronal Cell Function in the arRP Preclinical Mouse.

Figure 4:
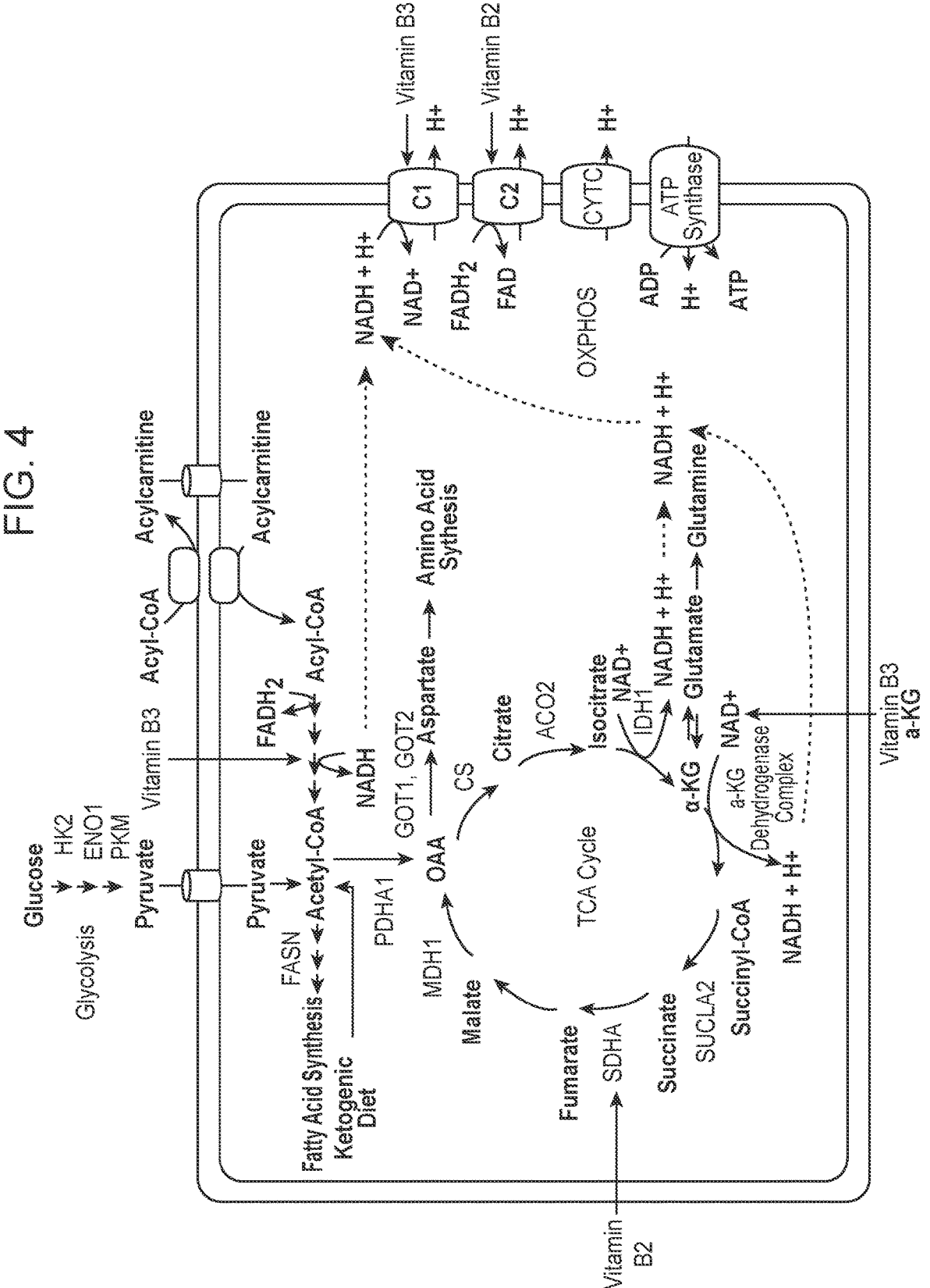
FIG. 4 shows metabolic therapy for Pde6α$^{D670G}$ mice based on vitreous biomarkers. Metabolic pathway diagram highlighting identified proteins in the Pde6α$^{D670G}$ vitreous (red text). Metabolites are represented by blue text. Affected pathways include the TCA cycle, glycolysis, and oxidative phosphorylation (OXPHOS).
Figure 5A:
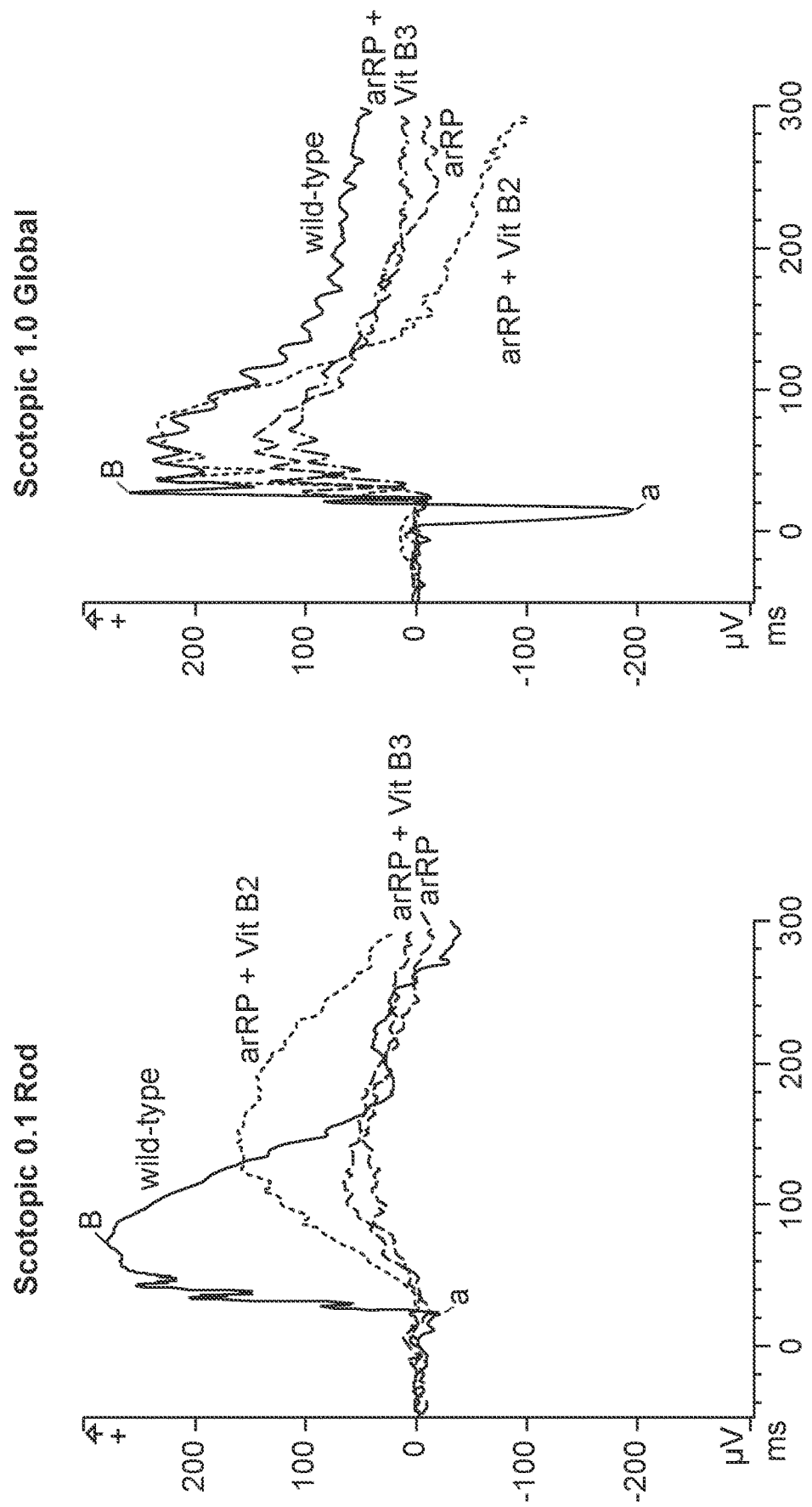

Since our proteomics data suggested that retinal oxidative metabolism was affected in early retinal degeneration in the arRP mouse, and defects in oxidative metabolism have been previously shown to contribute to photoreceptor degeneration in RP patients, we proposed to restore key metabolites involved in oxidative phosphorylation and the TCA cycle as potential non-pharmacologic therapies for attenuating neurodegeneration in the arRP preclinical model (FIG. 4). Flavin mononucleotide (FMN) and flavin adenine dinucleotide (FAD), which can be delivered via vitamin B$_2$ supplementation, are critical for enzymatic reactions within the electron transport chain and the TCA cycle (FIG. 5A). Additionally, nicotinamide adenine dinucleotide (NAD), available from vitamin B$_3$ supplementation, is a critical co-enzyme for aerobic metabolism and oxidative phosphorylation (FIG. 5A). Both vitamin B$_2$ and B$_3$ are water soluble and can be provided orally via drinking water without toxicity. We tested whether dietary vitamin B$_2$ (riboflavin) and/or dietary vitamin B$_3$ (nicotinamide) can increase oxidative phosphorylation and delay disease progression in our mouse model of arRP by delivering them via the drinking water at a concentration of 2.5 g/L, beginning at post-natal day 0 (P0). A negative control group received untreated water ad libitum. Compared to controls, arRP mice receiving vitamin B$_3$ showed an increased rod photoreceptor functional response on ERG analysis (FIG. 5B). Mice that received either vitamin B$_2$ or a combination of both B vitamins did not show an ERG rescue effect (FIG. 5B). However, analysis of a larger cohort of mice did not show statistical significance for rod photoreceptor cell function on ERG analysis, suggesting that the rescue effect was variable and did not affect all arRP mice that were provided the oral supplementation therapy (FIGS. 5C-5E).

Restoration of the Tricarboxylic Acid (TCA) Cycle with Oral Supplementation of a Single Metabolite Prolongs Neuronal Cell Survival and Vision in the arRP Preclinical Mouse.

Pde6α$^{D670G}$ mice display decreased PDE6A activity, and thus elevated levels of cGMP in the rod photoreceptor cell. We hypothesized that elevated levels of cGMP lead to elevation of intracellular calcium levels that can stimulate abnormally-rapid oxygenation of α-ketoglutarate. This stimulates glutamate uptake in the mitochondria through the $Ca^{2+}$-activated aspartate/glutamate carrier (SLC1A3). Glutamate depletion in turn disrupts the ability of photoreceptors to synthesize proteins leading to lack of protein turnover and photoreceptor cell death. Consistent with this hypothesis, we observed decreased protein expression in Pde6α$^{D670G}$ retinas at the onset of neuronal cell death at P15, preceding the detection of photoreceptor degeneration by histological analysis (FIG. 3).

Figure 6A:
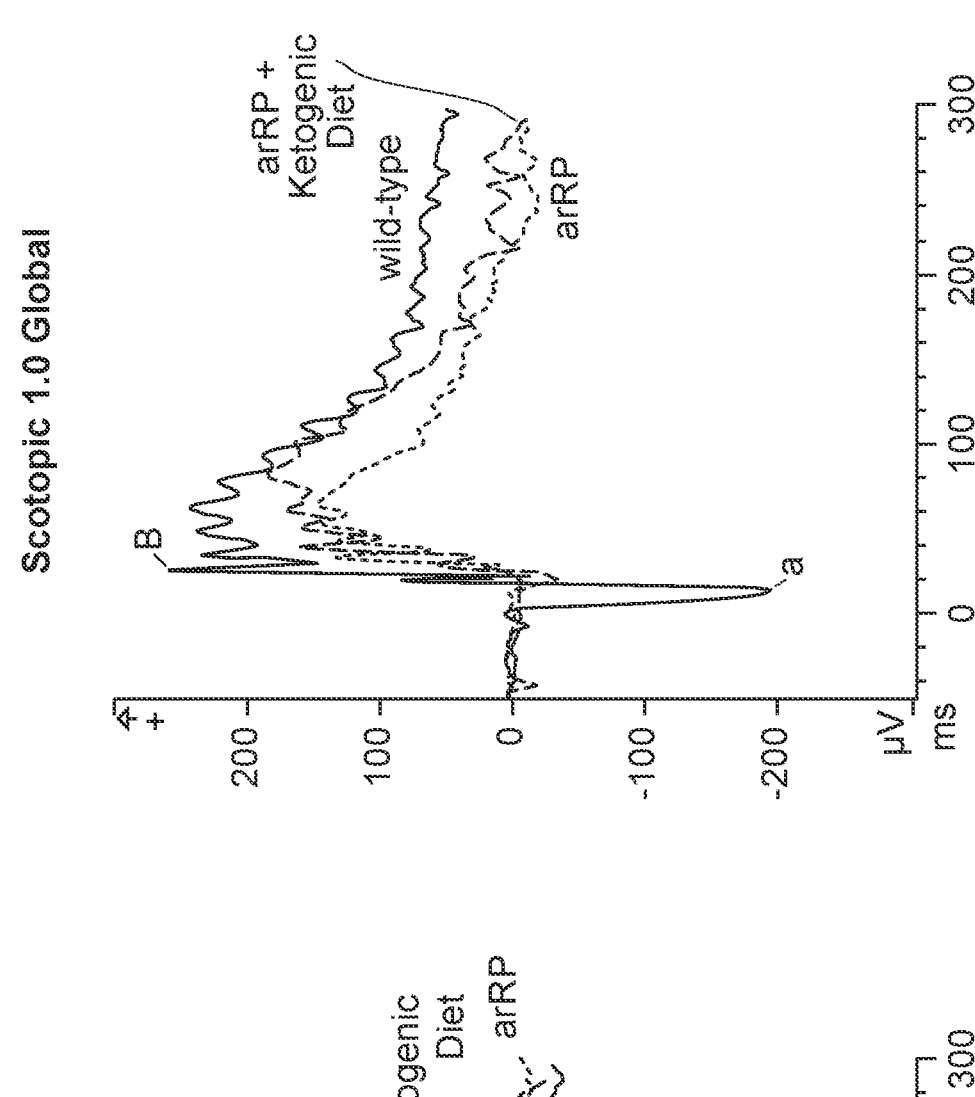
Figure 6A:
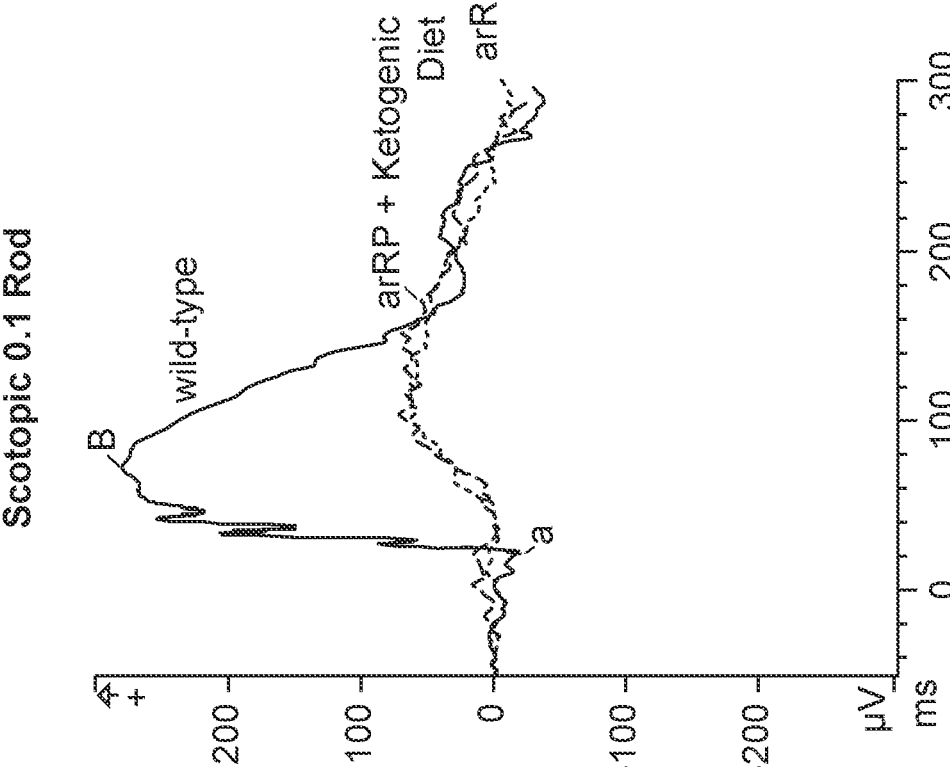
Figure 6E:
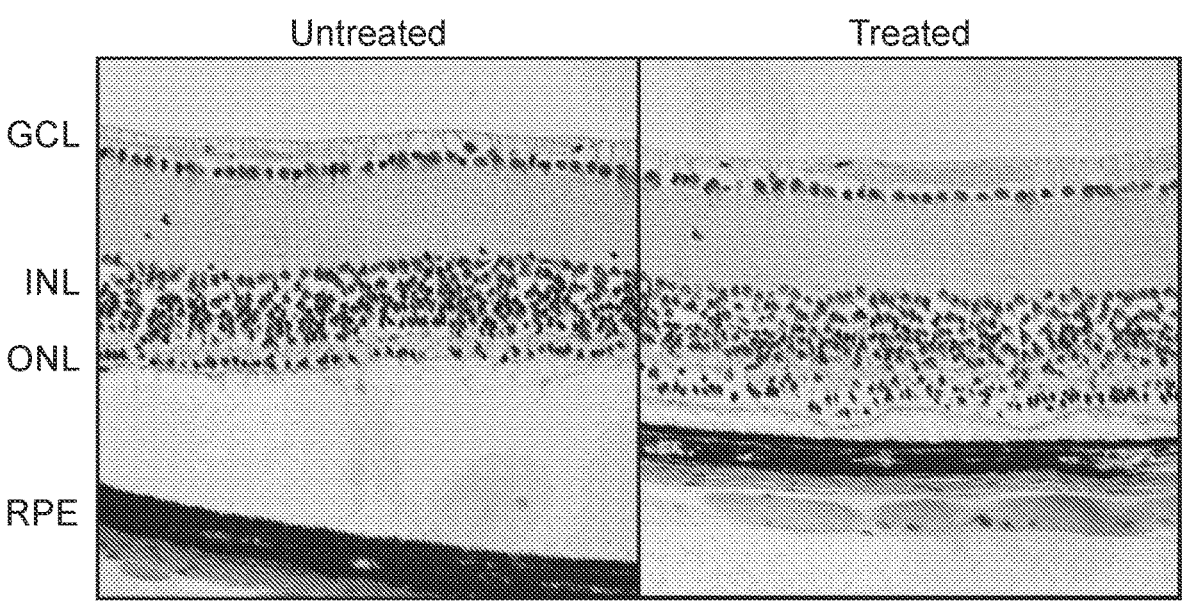
Figure 6F:
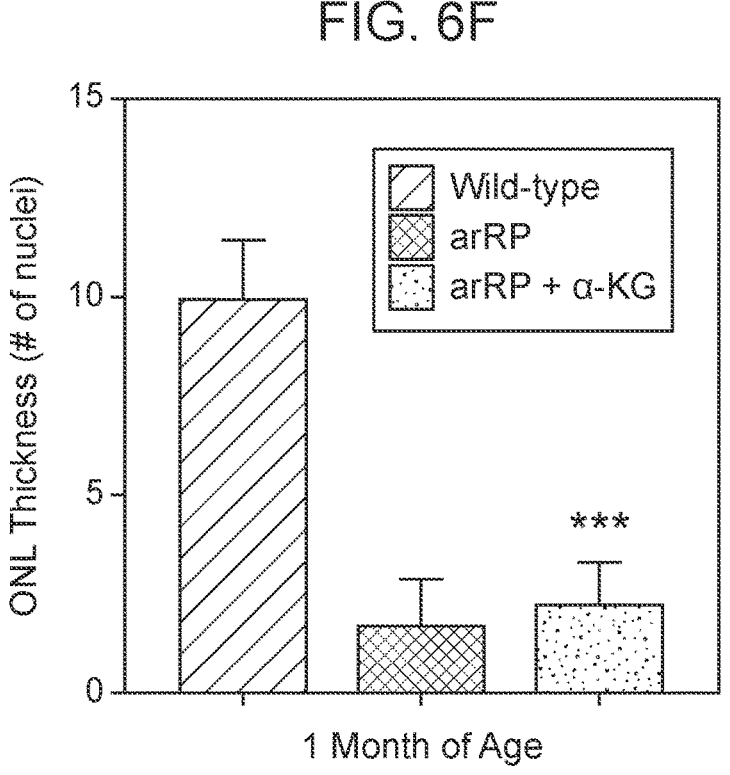

The ketogenic diet has gained public popularity and is an effective treatment option for patients with epileptic seizures. The ketogenic diet provides acetyl-CoA to feed into the TCA cycle toward the citrate synthetase reaction (FIG. 6A). This consumes oxaloacetate and diminishes the transamination of glutamate to aspartate, therefore providing more glutamate to be used by cells. Additionally, the ketogenic diet can shuttle malate back into the TCA cycle, and to support this need, we found that MDH2 levels were low in the Pde6α$^{D670G}$ retina at the onset of neuronal cell death (FIG. 4). Therefore, the arRP preclinical model was placed on a ketogenic diet (6:1:1 fat:protein:carbohydrate) beginning at post-natal day 21 (P21). Representative ERG traces of arRP mice fed the ketogenic diet showed no difference in the rod photoreceptor cell response, but a rescue of the global visual response compared to littermates on standard chow diet (FIG. 6B). Quantification of ERG recordings from arRP mice treated with the ketogenic diet shows no significant difference in ERG responses compared to littermates on a standard chow diet, although there was a trend toward a- and b-wave visual rescue at the maximal scotopic 1.0 ERG setting (FIG. 6C-E). Histological analysis of the outer nuclear layer (ONL) thickness showed mild, but significant, photoreceptor cell survival in mice treated with the ketogenic diet compared to untreated control littermates both at one and two months of age (FIG. 6F).

Since the ketogenic diet could not support nursing pups in their development, the diet was not delivered until P21, at mid-stage of disease. Dark-raising the Pde6α$^{D670G}$ mice allows for a delay in neuronal cell death, as the phototransduction cascade is not activated in the rod photoreceptor cells without light stimuli. Dark-raised Pde6α$^{D670G}$ mice on the ketogenic diet beginning at P21 showed significant visual rescue by ERG analysis compared to controls (FIG. 12). Therefore, supplementation with another metabolite involved in the TCA cycle that can be delivered at or before the onset of neuronal degeneration may provide a stronger neuroprotective effect on the photoreceptor cells.

Figure 7A:
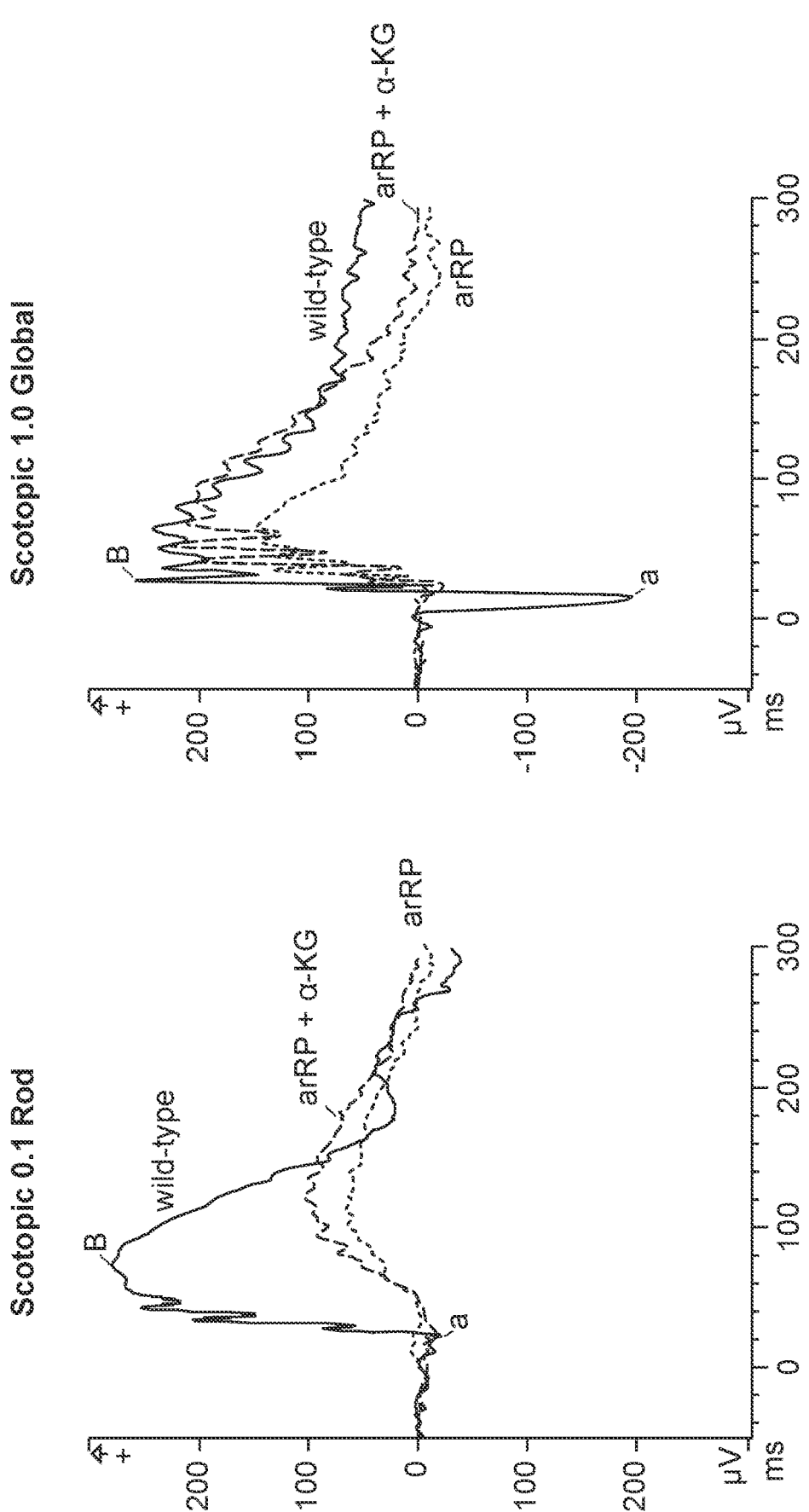
Figure 7E:
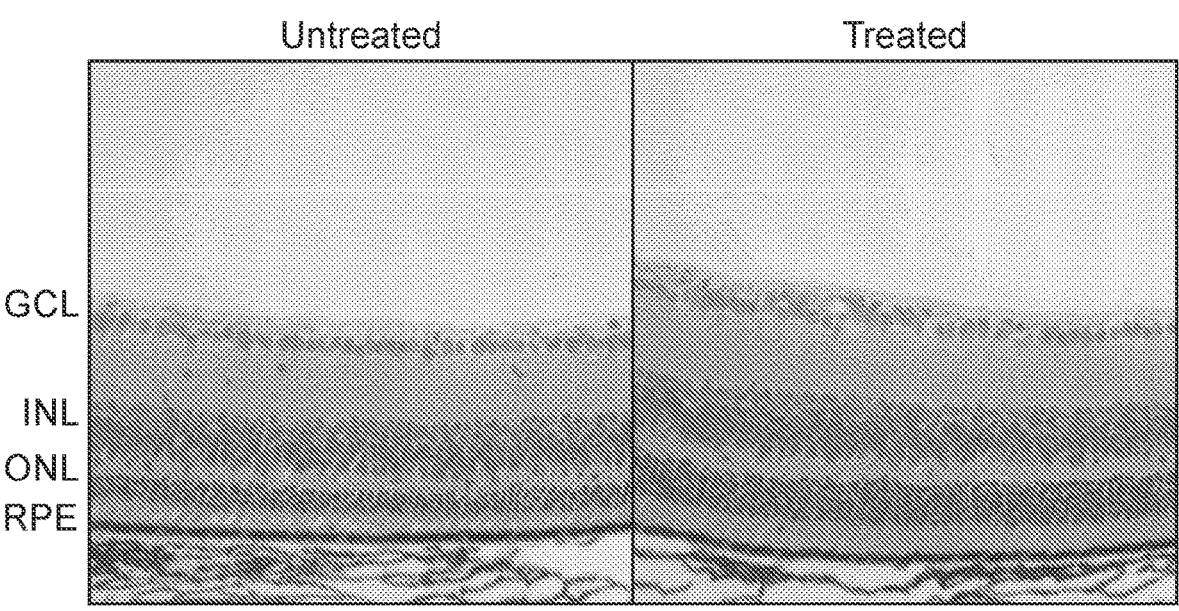
Figure 7F:
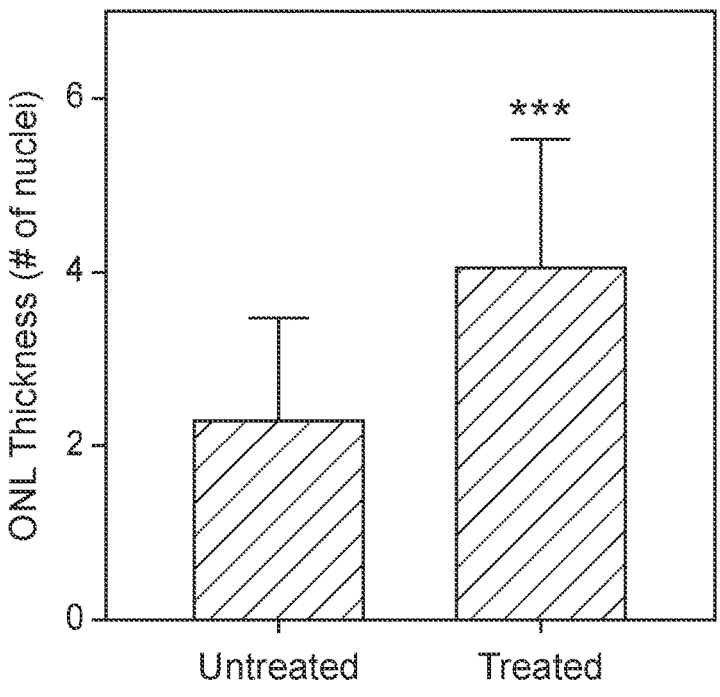

Alpha-ketoglutarate is not only a key component of the TCA cycle (FIG. 7A), but also plays a key role in amino acid biosynthesis and readily available as a supplement for humans. The amination of alpha-ketoglutarate provides glutamate, which increases amino acid synthesis and could promote photoreceptor cell survival in our preclinical arRP model. Furthermore, alpha-ketoglutarate derivatives have been delivered to mice to treat hypoxic conditions without any notations of adverse side effects. Pde6α$^{D670G}$ mice were provided with 10 g/L alpha-ketoglutarate in the drinking water beginning at PO and examined for functional visual rescue by ERG at one month of age. Representative ERG traces showed visual rescue both in the rod photoreceptors, rod-cone photoreceptor a-wave response, and global inner retina scotopic ERG response in Pde6α$^{D670G}$ mice treated with alpha-ketoglutarate compared to controls (FIG. 7B). Quantification of ERG responses in the cohorts of mice showed a significant rescue of the photoreceptors and inner retinal signaling in the Pde6α$^{D670G}$ mice treated with alpha-ketoglutarate compared to untreated controls, and in most cases the visual responses were not significantly different from those of normal, wild-type control mice (FIGS. 7C-7E). Histological analysis showed a significant rescue of photoreceptor cells and their inner/outer segments after treatment with alpha-ketoglutarate at one month of age (FIG. 7F). Thus, oral supplementation with a single metabolite, alpha-ketoglutarate, provided a significant neuroprotective effect on the rod photoreceptors and neural retinal network for at least one month of age in our arRP preclinical mouse model.

Validation of Pde6α$^{D670G}$ Vitreous Biomarkers in a Human Retinal Degeneration Case.

Figure 8A:
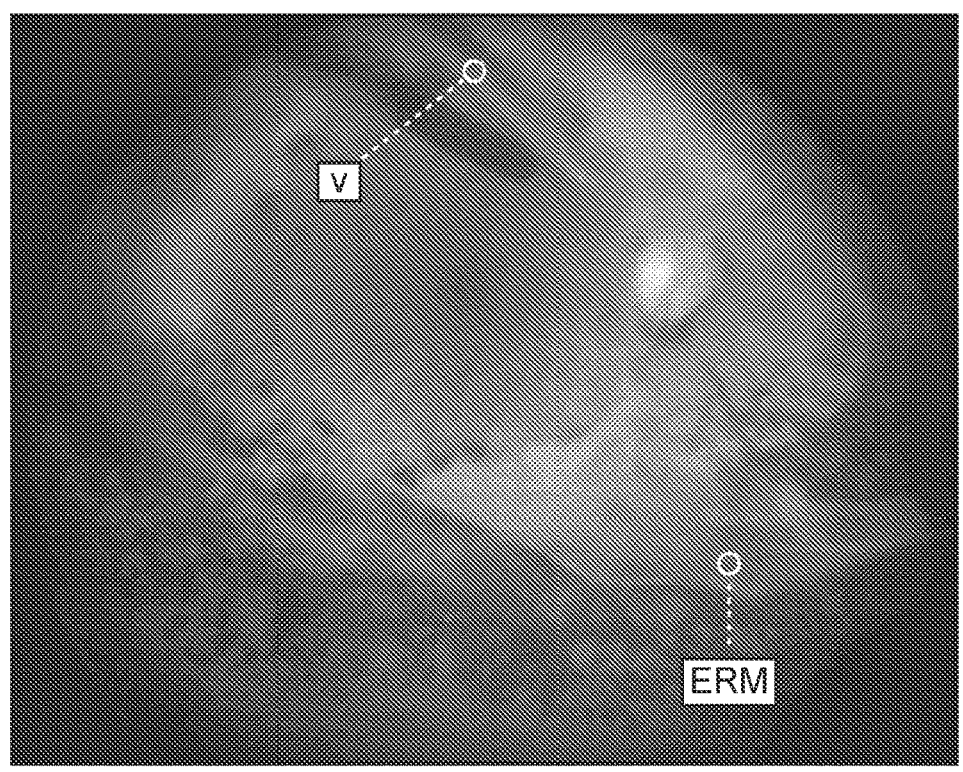
Figure 8B:
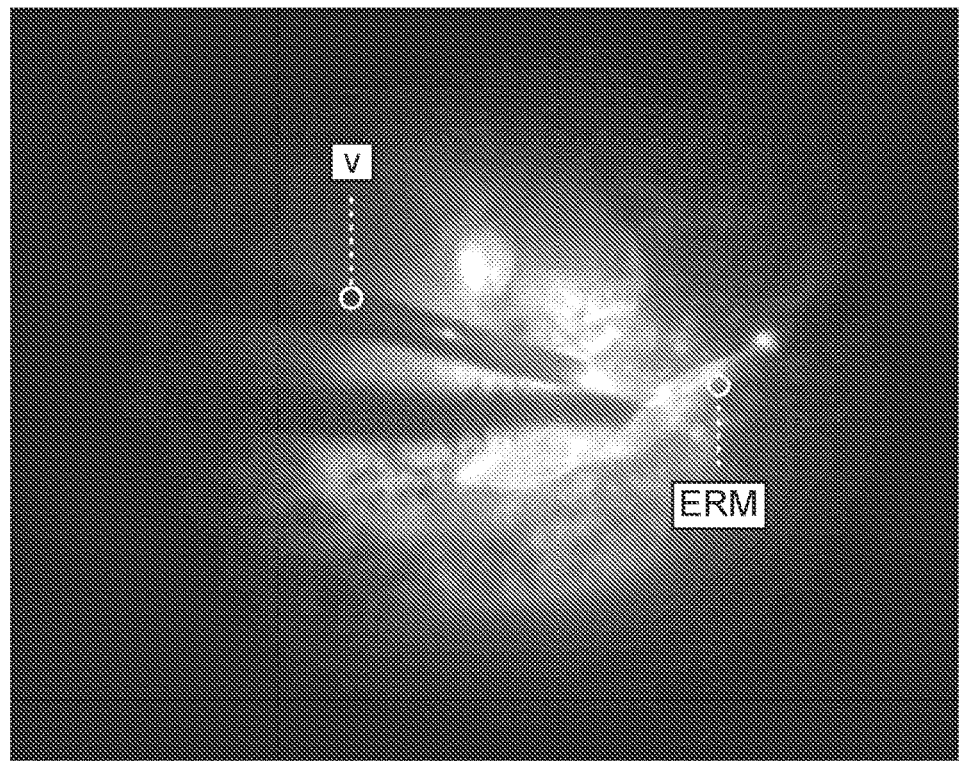

These findings suggest that changes in intracellular retinal protein expression can be detectable in the extracellular vitreous, and lead to potential pathways to target for therapeutics for arRP patients, as well as patients with other neurodegenerative diseases. We sought to validate some of our candidate biomarkers from the Pde6α$^{D670G}$ vitreous and retina samples with our human cases of retinitis pigmentosa caused by PDE6A mutations (FIG. 1). Vitreous biopsies were collected from the arRP proband (FIGS. 8A-8B), as well as the patient's affected brother (II:4), two ERM patients, and three control patients with idiopathic macular holes (IMH) or vitreous opacities (Table 1). Vitreous samples were analyzed using LC-MS/MS to determine proteomic content. We detected 612 proteins in the patient's vitreous by LC-MS/MS (Table 7). Protein spectral counts were analyzed by principal component analysis (PCA). Multi-group comparison (1-way ANOVA) was used to identify differentially-expressed proteins in the large-scale dataset. The score plot of PC1 and PC2 showed separation between the PDE6A, ERM, and controls samples based on differentially-expressed proteins that were significantly different between the three groups (FIG. 8C). ANOVA identified 36 proteins that were significantly differentially-expressed between the groups.

We next compared protein expression between PDE6A and ERM vitreous. There were 87 differentially-expressed proteins between PDE6A vitreous to ERM vitreous: 37 upregulated and 50 downregulated (p<0.05; FIG. 8D). We similarly observed a fraction (27%) of upregulated, intracellular proteins in PDE6A vitreous (FIG. 8E). Among the upregulated proteins in PDE6A vitreous were insulin-like growth factor-binding protein 2 (IBP2) and fatty acid synthase (FASN). FASN is involved in the synthesis of long-chain fatty acids from acetyl-CoA and NADPH. We similarly saw increased levels of fatty acid synthase in the vitreous of Pde6α$^{D670G}$ vitreous during early degeneration (FIG. 4). Loss of FASN in the neural retina has been shown to result in progressive neurodegeneration resembling retinitis pigmentosa in mouse models. A ketogenic diet would increase cellular levels of acetyl-CoA, which could feed into the fatty acid synthesis pathway and attenuate the loss of retina FASN. Although this case represents a late stage of disease, after loss of the rod neuronal cells, the validation of this candidate biomarker suggests that the Pde6α$^{D670G}$ mouse is a good model of arRP disease and neuronal cell death, and that the neuroprotective effects by metabolic supplementation in the Pde6α$^{D670G}$ mouse model may be translatable to human patients presenting with neural retinal degeneration.

DISCUSSION

We have previously shown that liquid biopsies of human vitreous can capture intracellular events in the neural retinal network that can guide diagnosis and treatment, importantly by highlighting critical pathways/metabolism that are affected during the progression of neuronal cell death and retinal remodeling. Here, we examined the retina and vitreous proteomes from a preclinical model of arRP, the Pde6α$^{D670G}$ mouse. We collected data from both the retinas and vitreous at early-, mid-, and late-stages of neurodegeneration. As expected, we found that rod phototransduction proteins were down-regulated in the retina and up-regulated within the vitreous at the onset of rod dystrophy, before loss of the photoreceptor cell nuclei is detectable by histological analysis. At this same timepoint, the onset of neuronal cell death, the Pde6α$^{D670G}$ mice under-express proteins critical for oxidative phosphorylation and aerobic metabolism, likely depressing protein turnover and leading to the retinal cell death of the rod photoreceptors. We then tested the hypothesis that restoring these metabolic pathways discovered in our proteomics screen would slow or reverse this disease progression.

We found that targeting oxidative phosphorylation by oral supplementation with vitamins B$_2$ and/or B$_3$ provided a mild electrophysiological rescue effect in some, but not all, neuronal cells of treated mice compared to their respective control littermates. Targeting the TCA cycle by acetyl-CoA production via the ketogenic diet led to a more significant rescue of inner retina visual function by one month of age. Furthermore, significant photoreceptor cell survival was detectable by histological analysis after treatment with the ketogenic diet. As the ketogenic diet could not be provided until weaning age, the effect was limited based on beginning the dietary treatment after approximately half of the neuronal photoreceptor cells have already been lost. Dark-raising the Pde6α$^{D670G}$ mice delayed photoreceptor cell death and increased the rescue effect of the ketogenic diet, further suggesting that earlier restoration of the TCA cycle metabolites may lead to prolonged visual rescue in the Pde6α$^{D670G}$ mouse model and neuroprotection of the photoreceptor cells and inner retinal network.

The loss of the TCA cycle proteins within the retina, and their subsequent upregulation within the vitreous at the onset of neuronal cell death, suggested a reduction in the ability of alpha-ketoglutarate to be aminated to glutamate, which in turn transaminates alpha-ketoacids to synthesize necessary amino acids. Since photoreceptors cannot synthesize new protein when alpha-ketoglutarate is low and glutamate uptake and depletion is blocked (leading to apoptosis), we tested the hypothesis that dietary alpha-ketoglutarate can delay disease progression by restoring the TCA cycle and glutamate levels within the retina. We found that oral supplementation with alpha-ketoglutarate alone provided significant visual rescue of the rods, cones, and inner retina visual responses through at least one month of age. Additionally, significant rescue of the ONL and the inner/outer segments of the photoreceptors were detectable on histological analysis at one month of age. Thus, oral supplementation with a single metabolite, alpha-ketoglutarate, provided a significant neuroprotective effect on the rod photoreceptors and neural retinal network for at least one month of age in our arRP preclinical mouse model.

Further studies are needed to test whether or not this rescue effect may be due to the metabolites acting either directly on the retinal cells, or indirectly via other organs in the body. Additionally, combination therapy with our treatment groups (alpha-ketoglutarate, the ketogenic diet, and/or vitamins B$_2$ and B$_3$) may have a synergistic effect in rescuing the neuronal cell loss and more closely reproduce a strategy to use in human arRP patients. Oral delivery of key components of the TCA cycle can affect other tissues and have undesirable side effects, for instance, mice provided alpha-ketoglutarate were found to be smaller in size and weight than controls on untreated water ad libitum. In humans, some of these side effects could be avoided by intraocular injection rather than systemic therapy (e.g. cell-permeating alpha-ketoglutarate derivatives[83-85]).

We validated the vitreous proteome of the Pde6α$^{D670G}$ mice with our human arRP patients and found overlapping proteins. Comparison of the human vitreous proteomes with the late-stage neurodegenerative Pde6α$^{D670G}$ mouse vitreous may provide a larger overlap of proteins as the time of disease would be more closely matched. However, the proteomic dataset in this study provided key pathways for targeting and testing therapeutics, and restoration of metabolites within these critical pathways in the arRP preclinical mouse model showed a safe and efficacious neuroprotective effect. Previous research studies have shown that metabolic rewiring is likely to be both a cause and a consequence of photoreceptor degeneration. The results from these studies lay the groundwork for future experiments to address how does the TCA cycle and aerobic metabolism influence the photoreceptors and their signaling to the inner retinal network, and thus improve upon neuroprotective approaches targeting photoreceptor cell metabolism. Overall, the key metabolic pathways (oxidative phosphorylation and the TCA cycle) detected in our proteomics screen are critical targets for therapeutics for RP, regardless of a patient's genetic mutation, and may be applicable to other human neurodegenerative diseases.

Methods

Study approval—The study protocol was approved by the Institutional Review Board for Human Subjects Research (IRB) at Columbia University and Stanford University, was HIPAA compliant, and adhered to the tenets of the Declaration of Helsinki. All subjects underwent informed consent for study participation. All experiments were performed in accordance with the ARVO Statement for the Use of Animals in Ophthalmic and Visual Research and were all approved by the Animal Care and Use Committee at the University of Iowa, Columbia University and Stanford University.

Mouse lines and husbandry—C57BL/6J-Pde6α$^{nmf363/nmf363}$, with a D670G mutation, herein referred to as Pde6α$^{D670G}$, mice were obtained from the Jackson Laboratory (Bar Harbor, ME, USA). Pde6α$^{D670G}$ are co-isogenic in the C57BL/6J (B6) background; therefore, age-matched B6 mice were used as experimental controls. Mice were bred and maintained at the facilities of Columbia University and Stanford University. Animals were kept on a light-dark cycle (12 hour-12 hour). Food and water were available ad libitum throughout the experiment, whether treated or untreated. Dark-raising was performed under 24 hr dark cycle following approved institutional guidelines. The ketogenic diet was provided by BioServ (Ketogenic Diet, AIN-76A-Modified, High-Fat, Paste; Flemington, NJ) in place of standard chow. The ketogenic diet was stored refrigerated and changed every other day for the mice during the duration of the experiment. Vitamins B$_2$ (Riboflavin, Sigma Aldrich) and B$_3$ (Nicotinamide, Sigma Aldrich) were provided at a concentration of 2.5 g/L in the mouse drinking water. Alpha-ketoglutarate (Alpha-ketoglutaric acid, Sigma Aldrich) was provided at a concentration of 10 g/L in the mouse drinking water. All water bottles were covered in foil to reduce light exposure and changed weekly during the duration of the experiment following approved institutional guidelines.

Human patient imaging—Clinical examination and testing was performed as previously described (32). Autofluorescent (AF) images were obtained using a Topcon TRC 50DX camera (Topcon, Pyramus, NJ, USA). Optical coherence tomography imaging was obtained from the spectral-domain Heidelberg HRA2 Spectralis, version 1.6.1 (Heidelberg Engineering, Inc, Vista, CA, USA). Genetic testing was performed as previously described (4).

Mouse autofluorescence/infrared imaging—AF/IR fundus imaging was obtained with the Spectralis scanning laser confocal ophthalmoscope (OCT-SLO Spectralis 2; Heidelberg Engineering, Heidelberg, Germany). Pupils were dilated using topical 2.5% phenylephrine hydrochloride and 1% tropicamide (Akorn, Inc., Lakeforest, IL, USA). Mice were anesthetized by intraperitoneal injection of 0.1 ml/10 g body weight of anesthesia [1 ml ketamine-100 mg/ml (Ketaset III, Fort Dodge, IA, USA) and 0.1 ml xylazine-20 mg/ml (Lloyd Laboratories, Shenandoah, IA, USA) in 8.9 ml PBS]. Body temperature was maintained at 37° C. using a heating pad during the procedure. AF imaging was obtained at 488-nm absorption and 495-nm emission using a 55° lens. IR imaging was obtained at 790 nm absorption and 830 nm emission using a 55° lens. Images were taken of the central retina, with the optic nerve located in the center of the image.

Electroretinography (ERG)—Mice were dark-adapted overnight, manipulations were conducted under dim red-light illumination, and recordings were made using Espion or Celeris ERG Diagnosys equipment (Diagnosys LLL, Littleton, MA, USA) as previously described. Briefly, adult B6 control mice were tested at the beginning of each session to ensure equal readouts from the electrodes for both eyes before testing the experimental mice. Pupils were dilated using topical 2.5% phenylephrine hydrochloride and 1% tropicamide (Akorn Inc., Lakeforest, IL, USA). Mice were anesthetized by intraperitoneal injection of 0.1 ml/10 g body weight of anesthesia [1 ml ketamine 100 mg/ml (Ketaset III, Fort Dodge, IA, USA) and 0.1 ml xylazine 20 mg/ml (Lloyd Laboratories, Shenandoah, IA, USA) in 8.9 ml PBS]. Body temperature was maintained at 37° C. during the procedure. Both eyes were recorded simultaneously and responses were averaged for each trial. Responses were taken from the Espion/Celeris readout in microvolts.

Histology—Mice were sacrificed and the eyes enucleated as previously described (19). Eyes were embedded in paraffin, sectioned, and stained with hematoxylin and eosin by Excalibur Pathology, Inc. (Norman, OK), before being visualized by light microscopy (Leica DM 5000B, Leica Microsystems, Germany). Quantification of photoreceptor nuclei was conducted on several sections that contained the optic nerve, as follows: the distance between the optic nerve and the ciliary body was divided into four, approximately equal, quadrants. Three columns of nuclei (how many cell nuclei thick) were counted within each single quadrant. These counts were then used to determine the average thickness of the ONL for each individual animal at each time. Sectioning proceeded along the long axis of the segment, so that each section contained upper and lower retina as well as the posterior pole.

Human vitreous sample collection—Pars plana vitrectomy for vitreous biopsy was performed as previously described (22). We used a single-step transconjunctival 23-gauge trocar cannula system (Alcon Laboratories Inc, Fort Worth, TX) as previously described. A light pipe and vitreous cutter were inserted into the mid vitreous and the cutter was activated for 30 seconds without infusion. An undiluted 1.0-cc sample of vitreous was then manually aspirated into a 3-cc syringe. Vitreous samples were immediately centrifuged in the operating room at 15,000 g for 5 minutes at room temperature to remove particulate matter, and samples were then stored at −80° C.

Mouse vitreous and retina sample collection—The vitreous and retina from 12 mouse eyes were eviscerated as described previously (8, 23, 24). Briefly, scleral tissue posterior to the limbus was grasped with 0.22 forceps and a microsurgical blade was used to make a linear incision in the cornea from limbus to limbus. A fine curved needle holder was inserted behind the lens toward the posterior aspect of the globe. The needle holder was partially closed and pulled forward pushing the lens through the corneal incision while leaving the eye wall intact. The vitreous was partially adherent to the lens. The lens-vitreous tissue was then placed into a filtered centrifugation tube containing 20 microliters of protease inhibitor cocktail (Roche) dissolved in PBS. The fine curved needle holder was placed as far posterior to the globe as possible, near the optic nerve. The needle holder was partially closed, and pulled forward, pushing the retina forward through the corneal incision. The vitreous appeared as a translucent gel adherent to the retina. The retina-vitreous tissue was placed into the filtered centrifuge tube containing the lens-vitreous tissue. The filtered centrifuge tube was spun at 14,000×g for 12 minutes and the eluent (vitreous) was collected.

Protein extraction and digestion—The received fluid samples were diluted in 2% SDS, 100 mM Tris-HCl (pH 7.6), 100 mM DTT to approximately 0.5 mL volume and heated at 95° C. for 10 min. Each sample was then briefly vortexed and sonicated for 10 seconds using a probe-tip sonicator (Omni International). The samples were then returned to incubate at 95° C. for an additional 10 min. Samples were then transferred to a 30 K Amicon MWCO device (Millipore) and centrifuged at 16,100×g for 30 min. Then 400 μl of 8 M urea, 100 mM Tris-HCl (pH 7.6) was added to each device and centrifuged as before and the filtrate discarded. This step was repeated. Then 400 μl of 8M urea, 100 mM Tris-HCl (pH 7.6), 15 mM iodoacetamide was added to each device and incubated in the dark for 30 minutes. The samples were then centrifuged as before, and the filtrate discarded. Then 400 μl of 8 M urea, 100 mM Tris-HCl (pH 7.6) was added to each device and centrifuged as before and the filtrate discarded. This step was repeated. Then 400 μl of 2 M urea, 100 mM Tris-HCl (pH 7.6) was added to each device along with 2.5 μg trypsin. The devices incubated overnight on a heat block at 37° C. The devices were then centrifuged, and the filtrate collected. Then 400 μl 0.5 M NaCl was added to each device and centrifuged as before. The filtrate was added to the previously collected filtrate.

Peptide desalting and fractionation—Digested peptides were desalted using C18 stop-and-go extraction (STAGE) tips. Briefly, for each sample a C18 STAGE tip was activated with methanol, then conditioned with 75% acetonitrile, 0.5% acetic acid followed by 0.5% acetic acid. Samples were loaded onto the tips and desalted with 0.5% acetic acid. Peptides were eluted with 75% acetonitrile, 0.5% acetic acid and lyophilized in a SpeedVac (Thermo Savant) to dryness, approximately 2 hours. Peptides were fractionated using SAX STAGE tips. Briefly, for each sample a SAX STAGE tip was activated with methanol, then conditioned with Britton-Robinson buffer (BRB), pH 3.0 followed by BRB (pH 11.5). Peptides were loaded onto the tips and the flow-through collected followed by and five additional fractions by subsequent application of BRB at pH 8.0, 6.0, 5.0, 4.0 and 3.0. Each fraction was desalted using a C18 STAGE tip and lyophilized as described above.

Liquid chromatography-tandem mass spectrometry (LC-MS/MS)—Each SAX fraction was analyzed by LC-MS/MS. LC was performed on an Agilent 1100 Nano-flow system. Mobile phase A was 94.5% MilliQ water, 5% acetonitrile, 0.5% acetic acid. Mobile phase B was 80% acetonitrile, 19.5% MilliQ water, 0.5% acetic acid. The 150 min LC gradient ran from 5% A to 35% B over 105 minutes, with the remaining time used for sample loading and column regeneration. Samples were loaded to a 2 cm×100 μm I.D. trap-column positioned on an actuated valve (Rheodyne). The column was 13 cm×100 μm I.D. fused silica with a pulled tip emitter. Both trap and analytical columns were packed with 3.5 μm C18 (Zorbax SB, Agilent). The LC was interfaced to a dual pressure linear ion trap mass spectrometer (LTQ Velos, Thermo Fisher) via nano-electrospray ionization. An electrospray voltage of 1.5 kV was applied to a pre-column tee. The mass spectrometer was programmed to acquire, by data-dependent acquisition, tandem mass spectra from the top 15 ions in the full scan from 400-1400 m/z. Dynamic exclusion was set to 30 s.

Data processing and library searching—Mass spectrometer MS data files were converted to mzXML format and then to mgf format using msconvert in ProteoWizard and mzXML_to_mgf v4.4, rev 1, respectively. Peak list data were searched using two algorithms: OMSSA v2.1.9 and X!Tandem TPP v4.4, rev 1. The UniProt mouse protein sequence library was used in a target-decoy format (derived from UniProt as of Oct. 22, 2012). The mgf files were searched using OMSSA with precursor settings of +/−2.0 Da and fragment tolerance of +/−0.8 Da. In X!Tandem, precursor settings were set to −1 Da and +3 Da and the fragment tolerance to 0.8 Da. The number of missed cleavages was set to 1; the fixed modifications were Carbamidomethyl (C); the variable modifications were Oxidation (M). XML output files were parsed using TPP v4.4, rev 1 in the programs PeptideProphet, iProphet, and ProteinProphet. Proteins were required to have 2 or more unique peptides with E-value scores of 0.01 or less. Relative quantitation was performed by spectral counting. Data were normalized based on total spectral counts (hits) per sample (Table 2).

Statistical and bioinformatics analysis—Results were also saved in Excel as .txt format and were uploaded into the Partek Genomics Suite 6.5 software package as described previously (5-9). The data was normalized to log base 2 and compared using 1-way ANOVA analysis. All proteins with non-significant (p>0.05) changes were eliminated from the table. The significant values were mapped using the 'cluster based on significant genes' visualization function with the standardization option chosen. PANTHER Pathway Analysis was utilized to determine the most significant molecular pathways affected by the proteins present in each group (25). Gene ontology (GO) analysis was also performed in PANTHER. Pie charts were created for the visualization of GO distributions within the list of proteins under the Batch ID search menu. Pie charts were created for each GO term category including biological process, molecular function, and cellular component. Differences in experimental groups were determined by the Student's t-test as appropriate, or by one-way ANOVA followed by Tukey's post-hoc multiple comparison's test. p values <0.05 were considered significant. For ERG and histological analysis of mouse eyes, differences were determined by the Student's t-test as appropriate, or by one-way ANOVA followed by Tukey's post-hoc multiple comparison's test. p values<0.05 were considered significant.

TABLE 1

Vitreous biopsies from RP patients and unaffected controls: RP, retinitis pigmentosa; ERM, epiretinal membrane; IMH, idiopathic macular hole.

| Patient | Sex | Age* | Eye | Surgical Indication | Diagnosis |
|---|---|---|---|---|---|
| | | | | Retinitis Pigmentosa Samples | |
| 1 | M | 38 | OD | Vitrectomy, membrane peel | RP/ERM |
| 2 | M | 41 | OS | Vitrectomy, membrane peel | RP/ERM |
| | | | | Control Samples | |
| 3 | M | 64 | OS | Vitrectomy | IMH |
| 4 | M | 69 | OD | Vitrectomy | IMH |
| 5 | F | 63 | OD | Vitrectomy | Vitreous Opacities |
| 6 | M | 81 | OD | Vitrectomy, membrane peel | ERM |
| 7 | F | 65 | OD | Vitrectomy, membrane peel | ERM |

*At the time of surgery

TABLE 2

Multidimensional liquid chromatography and mass spectrometry analysis.

| Genotype | Tissue | Age * | Protein Groups | Distinguishable Proteins | Distinct Peptides | SC (Weighted) | Protein Group FDR | Distinguishable Proteins FDR | Peptide FDR | PSM FDR |
|---|---|---|---|---|---|---|---|---|---|---|
| WT | Retina | 90 | 902 | 1057 | 3090 | 40771.62 | 0.039130435 | 0.033488372 | 0.011583012 | 0.016829768 |
| WT | Retina | 90 | 880 | 1034 | 3041 | 40744.37 | 0.029115342 | 0.024832856 | 0.009165303 | 0.016985708 |
| WT | Retina | 90 | 862 | 1008 | 2967 | 40520.45 | 0.038680319 | 0.033170732 | 0.011394102 | 0.01377402 |
| WT | Vitreous | 90 | 153 | 211 | 624 | 22066.45 | 0.167664671 | 0.124444444 | 0.043887147 | 0.003708254 |
| WT | Vitreous | 90 | 150 | 203 | 615 | 22244.06 | 0.181818182 | 0.137614679 | 0.047619048 | 0.003678699 |
| WT | Vitreous | 90 | 147 | 193 | 608 | 20931.69 | 0.139240506 | 0.107843137 | 0.035541195 | 0.003148151 |
| Pde6aD670G | Retina | 15 | 929 | 1072 | 2617 | 31083.11 | 0.012834225 | 0.011131725 | 0.004574914 | 0.010560639 |
| Pde6aD670G | Retina | 15 | 1014 | 1159 | 2874 | 31705.91 | 0.015655577 | 0.013710368 | 0.006243496 | 0.011851421 |
| Pde6aD670G | Retina | 15 | 1026 | 1173 | 2841 | 30972.73 | 0.017391304 | 0.015228426 | 0.007015082 | 0.009767153 |
| Pde6aD670G | Vitreous | 15 | 304 | 387 | 1116 | 15019.48 | 0.045016077 | 0.035532995 | 0.012466607 | 0.003587552 |
| Pde6aD670G | Vitreous | 15 | 296 | 375 | 1090 | 13692.92 | 0.052631579 | 0.041775457 | 0.014571949 | 0.003494961 |
| Pde6aD670G | Vitreous | 15 | 256 | 330 | 894 | 10265.62 | 0.030769231 | 0.023952096 | 0.008908686 | 0.003108466 |
| Pde6aD670G | Retina | 30 | 720 | 860 | 2414 | 12404.78 | 0.019257221 | 0.016147636 | 0.005782734 | 0.004181559 |
| Pde6aD670G | Retina | 30 | 769 | 920 | 2706 | 14018.78 | 0.018041237 | 0.015102481 | 0.005160339 | 0.003560295 |
| Pde6aD670G | Retina | 30 | 739 | 890 | 2632 | 13134.77 | 0.024064171 | 0.020022247 | 0.0068156 | 0.004859206 |
| Pde6aD670G | Vitreous | 30 | 94 | 143 | 286 | 1445.65 | 0.06185567 | 0.04109589 | 0.020761246 | 0.043312016 |
| Pde6aD670G | Vitreous | 30 | 74 | 118 | 253 | 1295.54 | 0.052631579 | 0.033333333 | 0.015686275 | 0.04820947 |
| Pde6aD670G | Vitreous | 30 | 70 | 117 | 245 | 1152.71 | 0.082191781 | 0.05 | 0.024193548 | 0.045773961 |

TABLE 2-continued

Multidimensional liquid chromatography and mass spectrometry analysis.

| Genotype | Tissue | Age * | Protein Groups | Distinguishable Proteins | Distinct Peptides | SC (Weighted) | Protein Group FDR | Distinguishable Proteins FDR | Peptide FDR | PSM FDR |
|---|---|---|---|---|---|---|---|---|---|---|
| Pde6aD670G | Retina | 90 | 334 | 429 | 1063 | 23518.55 | 0.096866097 | 0.076233184 | 0.031481481 | 0.016697201 |
| Pde6aD670G | Retina | 90 | 370 | 472 | 1158 | 24741.51 | 0.067885117 | 0.053608247 | 0.022203245 | 0.016435165 |
| Pde6aD670G | Retina | 90 | 447 | 553 | 1531 | 29185.72 | 0.052287582 | 0.042477876 | 0.015554115 | 0.010972265 |
| Pde6aD670G | Vitreous | 90 | 441 | 545 | 1628 | 42609.52 | 0.095032397 | 0.077601411 | 0.026666667 | 0.016248232 |
| Pde6aD670G | Vitreous | 90 | 416 | 526 | 1575 | 41910.27 | 0.109090909 | 0.087272727 | 0.030018762 | 0.012378095 |
| Pde6aD670G | Vitreous | 90 | 362 | 455 | 1337 | 33432.67 | 0.094736842 | 0.076109937 | 0.028023599 | 0.011597592 |

* Age in days.

TABLE 3

Pathway representation of down-regulated proteins in the Pde6a$^{D670G}$ retina.

| Pathway | -log(p- | Ratio | z-score |
|---|---|---|---|
| EIF2 Signaling | 3.46E+01 | 2.90E−01 | −5.657 |
| Regulation of eIF4 and p70S6K Signaling | 1.78E+01 | 2.42E−01 | −0.447 |
| mTOR Signaling | 1.55E+01 | 1.99E−01 | −2.309 |
| Mitochondrial Dysfunction | 1.40E+01 | 2.05E−01 | NaN |
| Sirtuin Signaling Pathway | 1.37E+01 | 1.58E−01 | −0.87 |
| TCA Cycle II (Eukaryotic) | 1.19E+01 | 5.65E−01 | NaN |
| tRNA Charging | 1.17E+01 | 4.10E−01 | NaN |
| Oxidative Phosphorylation | 9.71E+00 | 2.11E−01 | NaN |
| Protein Ubiquitination Pathway | 9.56E+00 | 1.40E−01 | NaN |
| RAN Signaling | 9.51E+00 | 5.88E−01 | NaN |
| Huntington's Disease Signaling | 9.11E+00 | 1.40E−01 | −0.905 |
| Phagosome Maturation | 8.35E+00 | 1.69E−01 | NaN |
| Gluconeogenesis I | 7.23E+00 | 3.85E−01 | NaN |
| Tight Junction Signaling | 6.66E+00 | 1.44E−01 | NaN |
| Phototransduction Pathway | 6.57E+00 | 2.45E−01 | NaN |
| Remodeling of Epithelial Adherens Junctions | 5.94E+00 | 2.03E−01 | −1 |
| Glycogen Degradation III | 5.90E+00 | 4.67E−01 | NaN |
| NRF2-mediated Oxidative Stress Response | 5.51E+00 | 1.24E−01 | −3 |
| Regulation of Actin-based Motility by Rho | 5.19E+00 | 1.67E−01 | −2.496 |
| Glycogen Degradation II | 5.08E+00 | 4.62E−01 | NaN |
| Glycolysis I | 5.05E+00 | 3.08E−01 | NaN |
| Granzyme A Signaling | 4.90E+00 | 3.50E−01 | NaN |
| RhoGDI Signaling | 4.59E+00 | 1.19E−01 | 2.5 |
| GDP-glucose Biosynthesis | 4.51E+00 | 5.00E−01 | NaN |
| Aldosterone Signaling in Epithelial Cells | 4.42E+00 | 1.19E−01 | −2.828 |
| Glucose and Glucose-1-phosphate Degradation | 4.27E+00 | 4.55E−01 | NaN |
| Pentose Phosphate Pathway | 4.27E+00 | 4.55E−01 | NaN |
| Purine Nucleotides De Novo Biosynthesis II | 4.27E+00 | 4.55E−01 | NaN |
| Ephrin B Signaling | 4.21E+00 | 1.64E−01 | −1.134 |
| RAR Activation | 4.13E+00 | 1.11E−01 | NaN |
| Inosine-5'-phosphate Biosynthesis II | 4.10E+00 | 1.00E+00 | NaN |
| Unfolded protein response | 3.98E+00 | 1.82E−01 | NaN |
| Aspartate Degradation II | 3.97E+00 | 5.71E−01 | NaN |
| Protein Kinase A Signaling | 3.87E+00 | 8.50E−02 | −2.785 |
| The Visual Cycle | 3.84E+00 | 3.00E−01 | NaN |
| GABA Receptor Signaling | 3.79E+00 | 1.59E−01 | NaN |
| Colanic Acid Building Blocks Biosynthesis | 3.68E+00 | 3.57E−01 | NaN |
| Pentose Phosphate Pathway (Oxidative Branch) | 3.51E+00 | 7.50E−01 | NaN |
| Clathrin-mediated Endocytosis Signaling | 3.41E+00 | 1.01E−01 | NaN |
| Semaphorin Signaling in Neurons | 3.41E+00 | 1.70E−01 | NaN |
| Tryptophan Degradation X (Mammalian, via Tryptamine) | 3.26E+00 | 2.40E−01 | NaN |
| Epithelial Adherens Junction Signaling | 3.25E+00 | 1.10E−01 | NaN |
| Antioxidant Action of Vitamin C | 3.13E+00 | 1.20E−01 | 3 |
| Synaptic Long-Term Potentiation | 3.11E+00 | 1.15E−01 | −2.138 |
| Gap Junction Signaling | 3.10E+00 | 9.74E−02 | NaN |
| Actin Cytoskeleton Signaling | 3.07E+00 | 9.25E−02 | −2.683 |
| Sumoylation Pathway | 3.07E+00 | 1.25E−01 | 0.333 |
| RhoA Signaling | 3.04E+00 | 1.13E−01 | −2.673 |
| Androgen Signaling | 3.01E+00 | 1.17E−01 | −1.342 |
| Aryl Hydrocarbon Receptor Signaling | 2.95E+00 | 1.06E−01 | −0.816 |

TABLE 4

Down-regulated proteins in the Pde6a$^{D670G}$ retina involved in oxidative phosphorylation.

| Symbol | Protein Name | p- | Fold Change |
|--------|--------------|-----|-------------|
| ATP5A1 | ATP synthase, mitochondrial F1 complex, alpha subunit 1 | 2.06E−13 | −128372 |
| ATP5B | ATP synthase, mitochondrial F1 complex, beta polypeptide | 3.97E−07 | −26.908 |
| ATP5C1 | ATP synthase, mitochondrial F1 complex, gamma polypeptide | 1.80E−02 | −329.308 |
| ATP5F1 | ATP synthase, mitochondrial Fo complex subunit B1 | 2.29E−03 | −6952.05 |
| ATP5H | ATP synthase, mitochondrial Fo complex subunit D | 2.27E−11 | −15810.3 |
| ATP5J2 | ATP synthase, mitochondrial Fo complex subunit F2 | 3.63E−12 | −18504.3 |
| ATP5L | ATP synthase, mitochondrial Fo complex subunit G | 1.02E−09 | −1803.99 |
| ATP5O | ATP synthase, mitochondrial F1 complex, O subunit | 1.88E−04 | −38887.2 |
| COX4I1 | cytochrome c oxidase subunit 4I1 | 1.39E−11 | −9966.55 |
| COX5A | cytochrome c oxidase subunit 5A | 4.42E−10 | −4717.69 |
| COX6B1 | cytochrome c oxidase subunit 6B1 | 1.61E−11 | −8962.81 |
| CYC1 | cytochrome c1 | 4.84E−03 | −1000 |
| CYCS | cytochrome c, somatic | 7.26E−13 | −3914.87 |
| MT-CO2 | cytochrome c oxidase subunit II | 3.11E−13 | −23633.3 |
| MT-ND5 | NADH dehydrogenase, subunit 5 (complex I) | 2.40E−03 | −1247.32 |
| NDUFA1 | NADH: ubiquinone oxidoreductase subunit A1 | 1.01E−03 | −3634.24 |
| NDUFA4 | NDUFA4, mitochondrial complex associated | 5.23E−04 | −14833.7 |
| NDUFA5 | NADH: ubiquinone oxidoreductase subunit A5 | 1.46E−03 | −2289.43 |
| NDUFA9 | NADH: ubiquinone oxidoreductase subunit A9 | 7.51E−04 | −5517.85 |
| NDUFA10 | NADH: ubiquinone oxidoreductase subunit A10 | 2.72E−09 | −6952.05 |
| NDUFA11 | NADH: ubiquinone oxidoreductase subunit A11 | 1.84E−03 | −1817.12 |
| NDUFA13 | NADH: ubiquinone oxidoreductase subunit A13 | 3.72E−04 | −23944.3 |
| NDUFB5 | NADH: ubiquinone oxidoreductase subunit B5 | 2.83E−03 | −1000 |
| NDUFB6 | NADH: ubiquinone oxidoreductase subunit B6 | 7.69E−04 | −8276.77 |
| NDUFB10 | NADH: ubiquinone oxidoreductase subunit B10 | 7.98E−04 | −5277.63 |
| NDUFS1 | NADH: ubiquinone oxidoreductase core subunit S1 | 1.03E−11 | −5517.85 |
| NDUFS2 | NADH: ubiquinone oxidoreductase core subunit S2 | 3.05E−13 | −4578.86 |
| NDUFS3 | NADH: ubiquinone oxidoreductase core subunit S3 | 2.19E−10 | −9252.13 |
| NDUFS4 | NADH: ubiquinone oxidoreductase subunit S4 | 2.22E−02 | −100 |
| NDUFS7 | NADH: ubiquinone oxidoreductase core subunit S7 | 1.48E−09 | −2620.74 |
| NDUFS8 | NADH: ubiquinone oxidoreductase core subunit S8 | 1.40E−14 | −6603.85 |
| NDUFV1 | NADH: ubiquinone oxidoreductase core subunit V1 | 9.64E−04 | −3914.87 |
| SDHA | succinate dehydrogenase complex flavoprotein subunit A | 4.48E−04 | −13276.1 |
| SDHB | succinate dehydrogenase complex iron sulfur subunit B | 9.64E−04 | −3914.87 |
| SDHC | succinate dehydrogenase complex subunit C | 1.35E−07 | −3419.95 |
| UQCR10 | ubiquinol-cytochrome c reductase, complex III subunit X | 5.49E−09 | −6257.32 |
| UQCRB | ubiquinol-cytochrome c reductase binding protein | 3.97E−11 | −2519.84 |
| UQCRC1 | ubiquinol-cytochrome c reductase core protein I | 3.66E−13 | −24449.8 |
| UQCRC2 | ubiquinol-cytochrome c reductase core protein II | 1.12E−10 | −4578.86 |
| UQCRFS1 | ubiquinol-cytochrome c reductase, Rieske iron-sulfur polypeptide | 3.56E−11 | −1000 |

TABLE 5

Down-regulated proteins in the Pde6a$^{D670G}$ retina involved in the tricarboxylic acid (TCA) cycle.

| Symbol | Protein Name | p- | Fold Change |
|--------|--------------|-----|-------------|
| ACO2 | aconitase 2 | 1.27E−14 | −22740.6 |
| CS | citrate synthase | 3.52E−04 | −15323 |
| DLD | dihydrolipoamide dehydrogenase | 6.22E−04 | −7268.48 |
| DLST | dihydrolipoamide S-succinyltransferase | 9.98E−03 | −2289.43 |
| FH | fumarate hydratase | 5.27E−13 | −2620.74 |
| IDH3A | isocitrate dehydrogenase 3 (NAD+) alpha | 1.84E−13 | −33970 |
| IDH3B | isocitrate dehydrogenase 3 (NAD+) beta | 6.53E−11 | −6952.05 |
| IDH3G | isocitrate dehydrogenase 3 (NAD+) gamma | 1.99E−03 | −1587.4 |
| MDH2 | malate dehydrogenase 2 | 1.00E−19 | −133663 |
| OGDH | oxoglutarate dehydrogenase | 8.63E−04 | −12295.9 |
| SDHA | succinate dehydrogenase complex flavoprotein subunit | 4.48E−04 | −13276.1 |
| SDHB | succinate dehydrogenase complex iron sulfur subunit | 9.64E−04 | −3914.87 |
| SDHC | succinate dehydrogenase complex subunit C | 1.35E−07 | −3419.95 |
| SUCLA2 | succinate-CoA ligase ADP-forming beta subunit | 7.74E−04 | −5616.1 |

TABLE 6

Down-regulated proteins in the Pde6a$^{D670G}$ retina involved in the sirtuin signaling pathway.

| Symbol | Protein Name | p- | Fold Change |
|---|---|---|---|
| ACLY | ATP citrate lyase | 4.72E−04 | −1622.88 |
| ATP5A1 | ATP synthase, mitochondrial F1 complex, alpha subunit 1 | 2.06E−13 | −128372 |
| ATP5B | ATP synthase, mitochondrial F1 complex, beta polypeptide | 3.97E−07 | −26.908 |
| ATP5C1 | ATP synthase, mitochondrial F1 complex, gamma polypeptide | 1.80E−02 | −329.308 |
| ATP5F1 | ATP synthase, mitochondrial Fo complex subunit B1 | 2.29E−03 | −6952.05 |
| CYC1 | cytochrome c1 | 4.84E−03 | −1000 |
| G6PD | glucose-6-phosphate dehydrogenase | 7.86E−10 | −1803.99 |
| GABARAPL1 | GABA type A receptor associated protein like 1 | 2.25E−02 | −125.992 |
| GLS | glutaminase | 2.22E−02 | −100 |
| GLUD1 | glutamate dehydrogenase 1 | 1.27E−11 | −9321.7 |
| GOT2 | glutamic-oxaloacetic transaminase 2 | 7.82E−03 | −3346.21 |
| H1F0 | H1 histone family member 0 | 1.27E−11 | −5646.22 |
| HIST1H1C | histone cluster 1 H1 family member c | 3.17E−10 | −70266.7 |
| LDHA | lactate dehydrogenase A | 1.19E−05 | −5.904 |
| LDHB | lactate dehydrogenase B | 9.04E−03 | −3.702 |
| MT-ND5 | NADH dehydrogenase, subunit 5 (complex I) | 2.40E−03 | −1247.32 |
| NDRG1 | N-myc downstream regulated 1 | 9.38E−13 | −4265.78 |
| NDUFA1 | NADH: ubiquinone oxidoreductase subunit A1 | 1.01E−03 | −3634.24 |
| NDUFA4 | NDUFA4, mitochondrial complex associated | 5.23E−04 | −14833.7 |
| NDUFA5 | NADH: ubiquinone oxidoreductase subunit A5 | 1.46E−03 | −2289.43 |
| NDUFA9 | NADH: ubiquinone oxidoreductase subunit A9 | 7.51E−04 | −5517.85 |
| NDUFA10 | NADH: ubiquinone oxidoreductase subunit A10 | 2.72E−09 | −6952.05 |
| NDUFA11 | NADH: ubiquinone oxidoreductase subunit A11 | 1.84E−03 | −1817.12 |
| NDUFA13 | NADH: ubiquinone oxidoreductase subunit A13 | 3.72E−04 | −23944.3 |
| NDUFB5 | NADH: ubiquinone oxidoreductase subunit B5 | 2.83E−03 | −1000 |
| NDUFB6 | NADH: ubiquinone oxidoreductase subunit B6 | 7.69E−04 | −8276.77 |
| NDUFB10 | NADH: ubiquinone oxidoreductase subunit B10 | 7.98E−04 | −5277.63 |
| NDUFS1 | NADH: ubiquinone oxidoreductase core subunit S1 | 1.03E−11 | −5517.85 |
| NDUFS2 | NADH: ubiquinone oxidoreductase core subunit S2 | 3.05E−13 | −4578.86 |
| NDUFS3 | NADH: ubiquinone oxidoreductase core subunit S3 | 2.19E−10 | −9252.13 |
| NDUFS4 | NADH: ubiquinone oxidoreductase subunit S4 | 2.22E−02 | −100 |
| NDUFS7 | NADH: ubiquinone oxidoreductase core subunit S7 | 1.48E−09 | −2620.74 |
| NDUFS8 | NADH: ubiquinone oxidoreductase core subunit S8 | 1.40E−14 | −6603.85 |
| NDUFV1 | NADH: ubiquinone oxidoreductase core subunit V1 | 9.64E−04 | −3914.87 |
| PDHA1 | pyruvate dehydrogenase (lipoamide) alpha 1 | 1.31E−03 | −2620.74 |
| PGAM1 | phosphoglycerate mutase 1 | 1.01E−04 | −3.45 |
| PGK1 | phosphoglycerate kinase 1 | 3.01E−05 | −5.821 |
| PPID | peptidylprolyl isomerase D | 8.88E−04 | −9966.55 |
| SDHA | succinate dehydrogenase complex flavoprotein subunit A | 4.48E−04 | −13276.1 |
| SDHB | succinate dehydrogenase complex iron sulfur subunit B | 9.64E−04 | −3914.87 |
| SDHC | succinate dehydrogenase complex subunit C | 1.35E−07 | −3419.95 |
| SF3A1 | splicing factor 3a subunit 1 | 2.22E−02 | −100 |
| SLC25A4 | solute carrier family 25 member 4 | 1.68E−15 | −195231 |
| SLC2A1 | solute carrier family 2 member 1 | 7.90E−03 | −416.34 |
| SOD1 | superoxide dismutase 1 | 4.76E−04 | −11617.6 |
| SOD2 | superoxide dismutase 2 | 5.93E−10 | −9654.89 |
| TIMM44 | translocase of inner mitochondrial membrane 44 | 0.00E+00 | −1000 |
| TOMM22 | translocase of outer mitochondrial membrane 22 | 1.61E−03 | −2000 |
| TRIM28 | tripartite motif containing 28 | 4.53E−03 | −1247.32 |
| TUBA4A | tubulin alpha 4a | 1.04E−05 | −5.718 |
| UQCRC2 | ubiquinol-cytochrome c reductase core protein II | 1.12E−10 | −4578.86 |
| UQCRFS1 | ubiquinol-cytochrome c reductase, Rieske iron-sulfur | 3.56E−11 | −1000 |
| VDAC1 | voltage dependent anion channel 1 | 6.15E−14 | −69196.4 |
| VDAC2 | voltage dependent anion channel 2 | 3.22E−15 | −18955.6 |

TABLE 7

Proteomic content of human vitreous samples LC-MS/MS analysis: RP, retinitis
pigmentosa; ERM, epiretinal membrane; IMH, idiopathic macular hole.

| Patient | Condition | Peptide Hits | Peptides | Proteins | Clusters | Unique Proteins |
|---|---|---|---|---|---|---|
| 1 | RP/ERM | 68,329 | 1,862 | 3,255 | 841 | 875 |
| 2 | RP/ERM | 75,336 | 1,481 | 733 | 181 | 215 |
| 3 | IMH | 120,442 | 17,112 | 755 | 198 | 235 |
| 4 | IMH | 112,461 | 1,673 | 774 | 180 | 217 |
| 5 | Vitreous Opacities | 61,329 | 1,849 | 1,086 | 268 | 307 |
| 6 | ERM | 114,166 | 1,627 | 738 | 178 | 352 |
| 7 | ERM | 108,540 | 1,717 | 891 | 233 | 286 |

REFERENCES

1. Tsang S H, Tsui I, Chou C L, Zernant J, Haamer E, Iranmanesh R, et al. A novel mutation and phenotypes in phosphodiesterase 6 deficiency. *Am J Ophthalmol.* 2008; 146(5):780-8.
2. Wert K J, Sancho-Pelluz J, and Tsang S H. Mid-stage intervention achieves similar efficacy as conventional early-stage treatment using gene therapy in a pre-clinical model of retinitis pigmentosa. *Hum Mol Genet.* 2014; 23(2):514-23.
3. Cole C J, Kwan A S, Laidlaw D A, and Aylward G W. A new technique of combined retinal and choroidal biopsy. *Br J Ophthalmol.* 2008; 92(10):1357-60.
4. Lim L L, Suhler E B, Rosenbaum J T, and Wilson D J. The role of choroidal and retinal biopsies in the diagnosis and management of atypical presentations of uveitis. *Trans Am Ophthalmol Soc.* 2005; 103:84-91; discussion-2.
5. Velez G, Roybal C N, Colgan D, Tsang S H, Bassuk A G, and Mahajan V B. Precision Medicine: Personalized Proteomics for the Diagnosis and Treatment of Idiopathic Inflammatory Disease. *JAMA ophthalmology.* 2016; 134 (4):444-8.
6. Skeie J M, Roybal C N, and Mahajan V B. Proteomic insight into the molecular function of the vitreous. *PLoS One.* 2015; 10(5):e0127567.
7. Skeie J M, and Mahajan V B. Proteomic landscape of the human choroid-retinal pigment epithelial complex. *JAMA ophthalmology.* 2014; 132(11):1271-81.
8. Skeie J M, and Mahajan V B. Proteomic interactions in the mouse vitreous-retina complex. *PLoS One.* 2013; 8(11):e82140.
9. Mahajan V B, and Skeie J M. Translational vitreous proteomics. Proteomics Clin Appl. 2014; 8(3-4):204-8.
10. Sakamoto K, McCluskey M, Wensel T G, Naggert J K, and Nishina P M. New mouse models for recessive retinitis pigmentosa caused by mutations in the Pde6a gene. *Hum Mol Genet.* 2009; 18(1):178-92.
11. Velez G, Bassuk A G, Colgan D, Tsang S H, and Mahajan V B. Therapeutic Drug Repositioning Using Personalized Proteomics of Liquid Biopsies. *JCI Insight.* 2017; In Press.
12. Velez G, Roybal C N, Binkley E, Bassuk A G, Tsang S H, and Mahajan V B. Proteomic Analysis of Elevated Intraocular Pressure with Retinal Detachment. *Am J Ophthalmol Case Rep.* 2017; 5:107-10.
13. Hartong D T, Berson E L, and Dryja T P. Retinitis pigmentosa. *Lancet.* 2006; 368(9549):1795-809.
14. Hamel C. Retinitis pigmentosa. *Orphanet J Rare Dis.* 2006; 1:40.
15. Schuerch K, Marsiglia M, Lee W, Tsang S H, and Sparrow J R. Multimodal Imaging of Disease-Associated Pigmentary Changes in Retinitis Pigmentosa. *Retina.* 2016; 36 Suppl 1:S147-S58.
16. Sayman Muslubas I, Karacorlu M, Arf S, Hocaoglu M, and Ersoz M G. Features of the Macula and Central Visual Field and Fixation Pattern in Patients with Retinitis Pigmentosa. *Retina.* 2018; 38(2):424-31.
17. Popovic P, Jarc-Vidmar M, and Hawlina M. Abnormal fundus autofluorescence in relation to retinal function in patients with retinitis pigmentosa. *Graefes Arch Clin Exp Ophthalmol.* 2005; 243(10):1018-27.
18. Wakabayashi T, Sawa M, Gomi F, and Tsujikawa M. Correlation of fundus autofluorescence with photoreceptor morphology and functional changes in eyes with retinitis pigmentosa. *Acta Ophthalmol.* 2010; 88(5):e177-83.
19. Li Y, Wu W H, Hsu C W, Nguyen H V, Tsai Y T, Chan L, et al. Gene therapy in patient-specific stem cell lines and a preclinical model of retinitis pigmentosa with membrane frizzled-related protein defects. *Mol Ther.* 2014; 22(9):1688-97.
20. Mahajan V B, Elkins K A, Russell S R, Boldt H C, Gehrs K M, Weingeist T A, et al. Bilateral intravitreal injection of antivascular endothelial growth factor therapy. *Retina.* 2011; 31(1):31-5.
21. Tlucek P S, Folk J C, Orien J A, Stone E M, and Mahajan V B. Inhibition of neovascularization but not fibrosis with the fluocinolone acetonide implant in autosomal dominant neovascular inflammatory vitreoretinopathy. *Arch Ophthalmol.* 2012; 130(11):1395-401.
22. Skeie J M, Brown E N, Martinez H D, Russell S R, Birkholz E S, Folk J C, et al. Proteomic analysis of vitreous biopsy techniques. *Retina.* 2012; 32(10):2141-9.
23. Mahajan V B, Skeie J M, Assefnia A H, Mahajan M, and Tsang S H. Mouse eye enucleation for remote high-throughput phenotyping. *J Vis Exp.* 2011(57).
24. Skeie J M, Tsang S H, and Mahajan V B. Evisceration of mouse vitreous and retina for proteomic analyses. *J Vis Exp.* 2011(50).
25. Fabregat A, Sidiropoulos K, Garapati P, Gillespie M, Hausmann K, Haw R, et al. The Reactome pathway Knowledgebase. *Nucleic Acids Res.* 2016; 44(D1):D481-7.

What is claimed is:

1. A method of diagnosing and treating a subject with retinitis pigmentosa, the method comprising:
   a) obtaining a vitreous sample from the subject;
   b) measuring one or more biomarkers in the vitreous sample, wherein the biomarkers are selected from the group consisting of rhodopsin, guanine nucleotide-binding protein alpha subunit and beta subunit, phosducin, cyclic nucleotide-gated channel beta 1, rhodopsin kinase, recoverin, and S-arrestin;
   c) determining that the subject has increased levels of the one or more biomarkers selected from the group consisting of rhodopsin, guanine nucleotide-binding protein alpha subunit and beta subunit, phosducin, cyclic nucleotide-gated channel beta 1, rhodopsin kinase, recoverin, and S-arrestin in the vitreous sample compared to reference values ranges for levels of the one or more biomarkers in a control sample, wherein the increased levels of the one or more biomarkers indicate the subject has retinitis pigmentosa; and
   d) administering to the subject diagnosed with retinitis pigmentosa a therapeutically effective amount of α-ketoglutarate or a derivative thereof.

2. The method of claim 1, further comprising administering to the subject diagnosed with retinitis pigmentosa a nutritional supplement comprising vitamin A, vitamin B2, vitamin B3, retinyl palmitate, docosahexaenoic acid (DHA), lutein, or a combination thereof.

3. The method of claim 2, wherein the nutritional supplement comprises vitamin B2, vitamin B3, or a combination thereof.

4. The method of claim 1, further comprising putting the subject diagnosed with retinitis pigmentosa on a ketogenic diet.

* * * * *